US012364790B2

(12) United States Patent
Soletti et al.

(10) Patent No.: US 12,364,790 B2
(45) Date of Patent: Jul. 22, 2025

(54) EXTRACELLULAR MATRIX SYSTEMS, DEVICES, AND METHODS OF DEPLOYMENT

(71) Applicant: RENERVA, LLC, Pittsburgh, PA (US)

(72) Inventors: Lorenzo Soletti, Pittsburgh, PA (US); Josh Bowman, Pittsburgh, PA (US); Nicole Cwalina, Roswell, GA (US); Brandon Burger, Pittsburgh, PA (US); J. Christopher Flaherty, Nottingham, NH (US)

(73) Assignee: Renerva, LLC, Pittsburgh, PA (US)

( * ) Notice: Subject to any disclaimer, the term of this patent is extended or adjusted under 35 U.S.C. 154(b) by 538 days.

(21) Appl. No.: 17/788,450

(22) PCT Filed: Dec. 30, 2020

(86) PCT No.: PCT/US2020/067431
§ 371 (c)(1),
(2) Date: Jun. 23, 2022

(87) PCT Pub. No.: WO2021/138399
PCT Pub. Date: Jul. 8, 2021

(65) Prior Publication Data
US 2023/0034585 A1    Feb. 2, 2023

Related U.S. Application Data

(60) Provisional application No. 63/085,797, filed on Sep. 30, 2020, provisional application No. 62/954,813, filed on Dec. 30, 2019.

(51) Int. Cl.
*A61L 27/36*    (2006.01)
*A61K 35/30*    (2015.01)

(52) U.S. Cl.
CPC .......... *A61L 27/3633* (2013.01); *A61K 35/30* (2013.01); *A61L 27/3675* (2013.01); *A61L 2430/32* (2013.01)

(58) Field of Classification Search
None
See application file for complete search history.

(56) References Cited

U.S. PATENT DOCUMENTS

| 5,354,305 | A | 10/1994 | Lewis, Jr. |
|---|---|---|---|
| 7,387,604 | B2 | 6/2008 | Case et al. |
| 8,741,352 | B2 | 6/2014 | Hodde et al. |
| 8,802,436 | B1 | 8/2014 | Kentner et al. |
| 9,277,999 | B2 | 3/2016 | Badylak et al. |
| 9,402,868 | B2 | 8/2016 | Muir |
| 9,622,849 | B2 | 4/2017 | El-Kurdi et al. |
| 9,642,937 | B2 | 5/2017 | Zhao et al. |
| 2006/0116548 | A1 | 6/2006 | Case et al. |
| 2008/0107750 | A1 | 5/2008 | Hodde et al. |
| 2010/0222882 | A1 | 9/2010 | Badylak et al. |
| 2012/0156250 | A1 | 6/2012 | Christman et al. |
| 2012/0330437 | A1 | 12/2012 | El-Kurdi et al. |
| 2013/0337549 | A1 | 12/2013 | Muir |
| 2014/0227362 | A1 | 8/2014 | Kentner et al. |
| 2014/0356331 | A1 | 12/2014 | Badylak et al. |
| 2016/0101215 | A1 | 4/2016 | Zhao et al. |
| 2016/0184479 | A1 | 6/2016 | Fette |
| 2016/0304832 | A1 | 10/2016 | Hariri et al. |
| 2018/0006493 | A1 | 1/2018 | Ludois et al. |
| 2018/0228939 | A1 | 8/2018 | Hiles et al. |
| 2019/0015552 | A1 | 1/2019 | Badylak et al. |
| 2022/0323648 | A1 | 10/2022 | Soletti et al. |

FOREIGN PATENT DOCUMENTS

| WO | 20110032139 | 3/2011 |
|---|---|---|
| WO | 2019094734 | 5/2019 |
| WO | 2021067456 | 4/2021 |

OTHER PUBLICATIONS

Lin Tao et al: Hydrogel derived from porcine decellularized nerve tissue as a promising biomaterial for repairing peripheral nerve defects:, Acta Biomaterialia, vol. 73, Apr. 9, 2015, pp. 326-338, Elsevier, Ltd. DOI: 10.1016/J.ACTBIO.2018.04.001.
Chen Chung-Chia et al: "The Physicochemical Properties of Decellularized Extracellular Matrix-Coated 3D Printed Poly([epsilon]-caprolactone) Nerve Conduits for Promoting Schwann Cells Proliferation and Differentiation", Material, vol. 11 No. 9, Sep. 9, 2018, p. 1665-1680, MDPI, Basel Switzerland, DOI: 10.3390/ma11091665.
Extended European Search Report dated Dec. 19, 2023 issued for corresponding European Application No. 20911269.7.
Extended European Search Report dated Sep. 14, 2023 issued for corresponding European Application No. 20872531.7.
International Search Report dated Jun. 1, 2023 issued in corresponding International Application No. PCT/US22/54351.
Written Opinion of International Searching Authority dated Jun. 1, 2023 issued in corresponding International Application No. PCT/US22/54351.
International Search Report and Written Opinion dated Mar. 15, 2023 issued in corresponding International Application No. PCT/US22/45365.
Renerva LLC. "Stage I: Development of a Peripheral Nerve Matrix Conduit to Enable Nerve Regeneration", NSF Awards, Sep. 13, 2021, pp. 1-3. Retrieved from the internet on Jan. 31, 2023. url: https://www.nsf.gov/awardssearch/showAward?AWD_ID=1913761 &HistoricalAwards=false>; p. 2, middle-bottom.
International Preliminary Report on Patentability dated Apr. 14, 2022 issued in related International Application No. PCT/US2020/053570.

(Continued)

*Primary Examiner* — Michael V Meller
(74) *Attorney, Agent, or Firm* — Katleen Kurnicki

(57) ABSTRACT

Systems, devices, and methods for treating a nerve injury in a patient are provided. The system includes an extracellular matrix, a neutralizing element, and a reconstituting element. The extracellular matrix is configured to promote and/or sustain the growth of tissue and/or associated tissue properties proximate the nerve injury.

16 Claims, 54 Drawing Sheets

(56) References Cited

OTHER PUBLICATIONS

International Search Report and Written Opinion dated Jan. 6, 2021 issued in related International Application No. PCT/US2020/053570.

Soletti et al. "A Bi-Layered Elastomeric Scaffold for Tissue Engineering of Small-Diameter Vascular Grafts," Acta Biomaterialia, Jan. 1, 2010, vol. 6, Issue 1, pp. 110-122.

Takeda et al. "Fabrication of 2D and 3D Constructs From Reconstituted Decellularized Tissue Extracellular Matrices," Journal of Biomedical Nanotechnology, Dec. 1, 2014, vol. 10, Issue 12, pp. 3631-3637.

International Preliminary Report on Patentability dated Jul. 14, 2022 issued in corresponding International Application No. PCT/US2020/067431.

International Search Report and Written Opinion dated Mar. 8, 2021 issued in corresponding International Application No. PCT/US2020/067431.

International Search Report and Written Opinion dated Jun. 1, 2023 issued in corresponding International Application No. PCT/US22/54351.

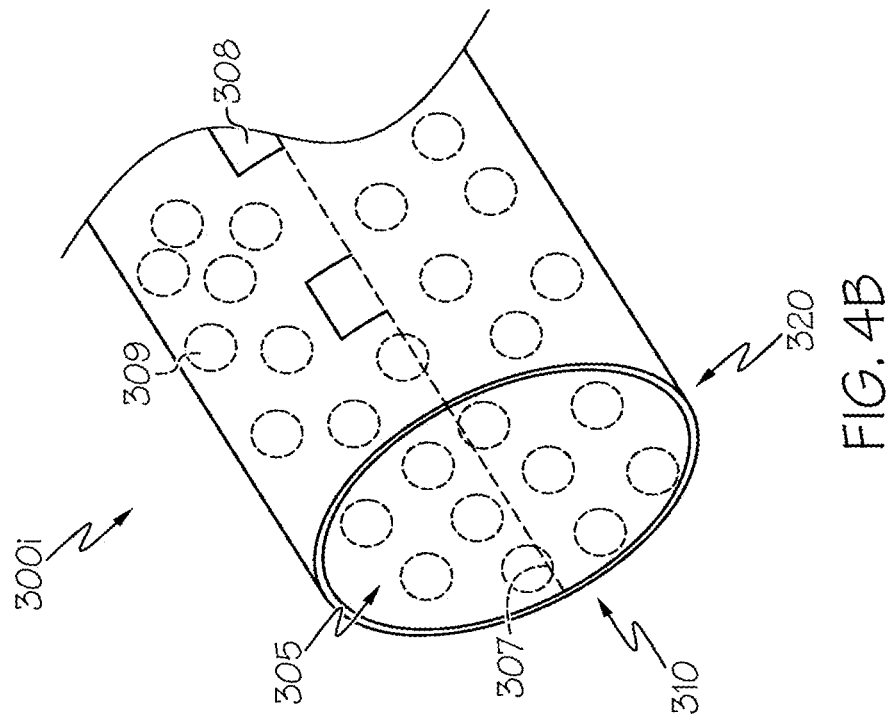
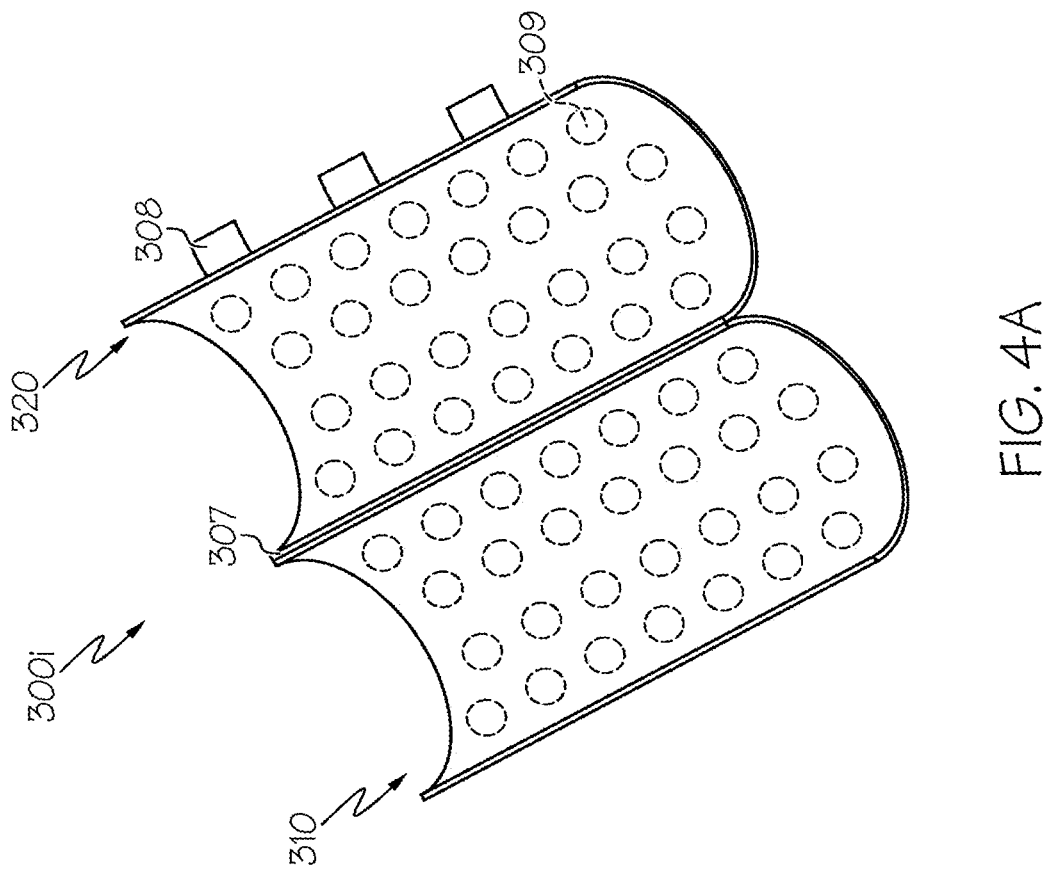
FIG. 4B
FIG. 4A

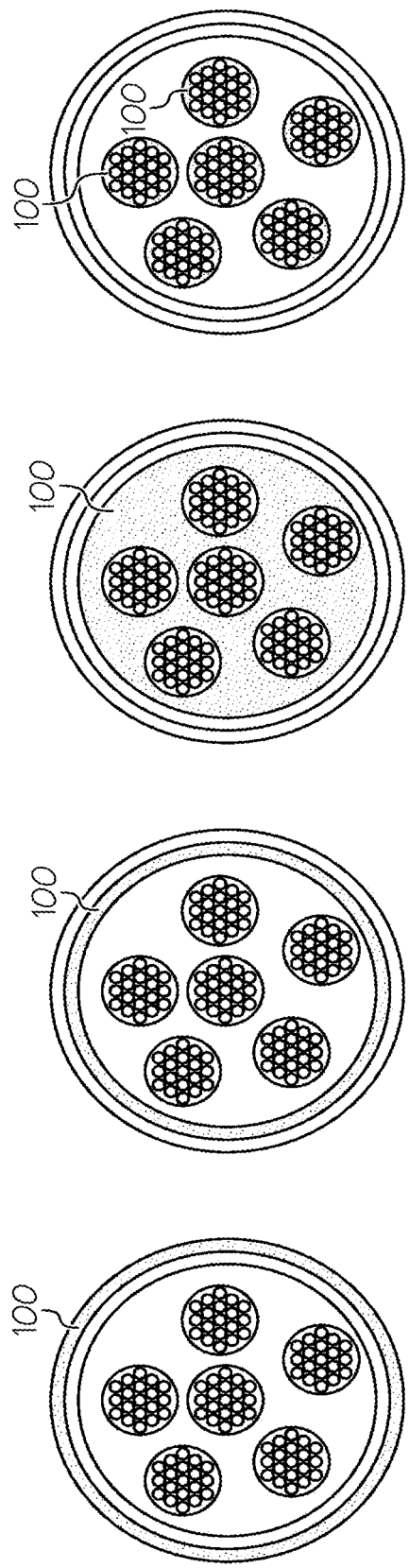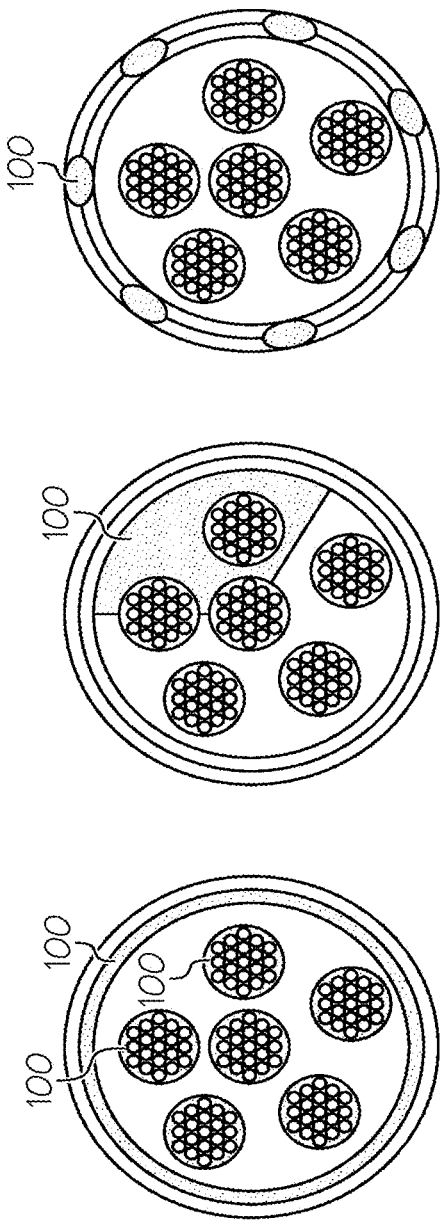

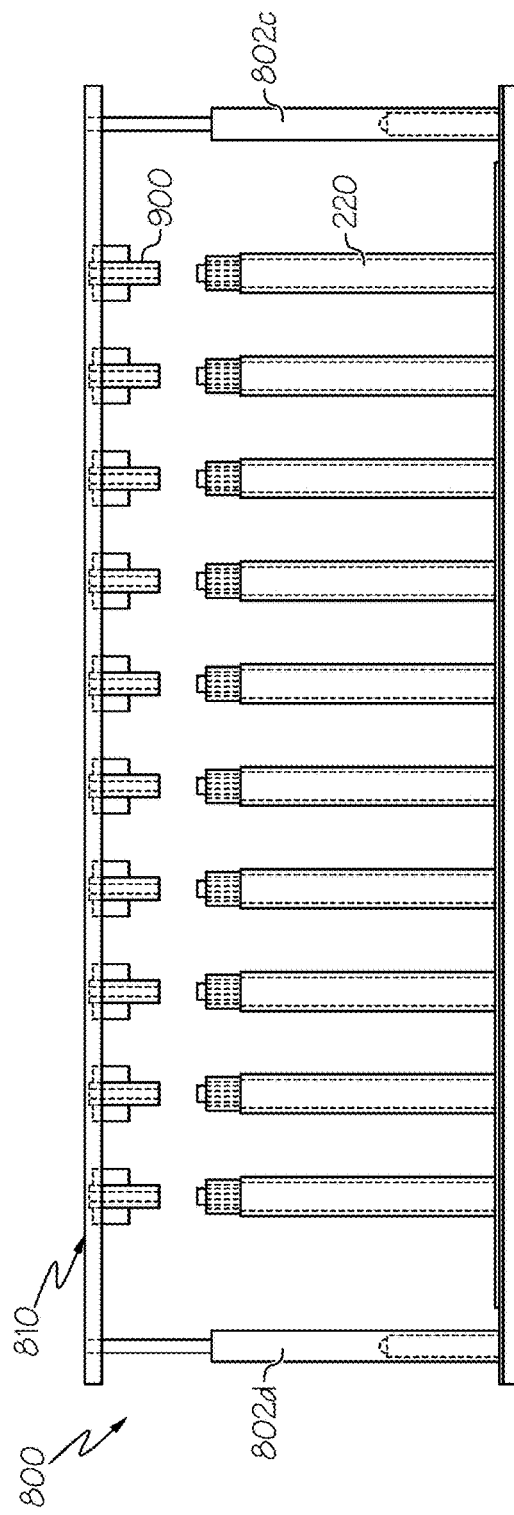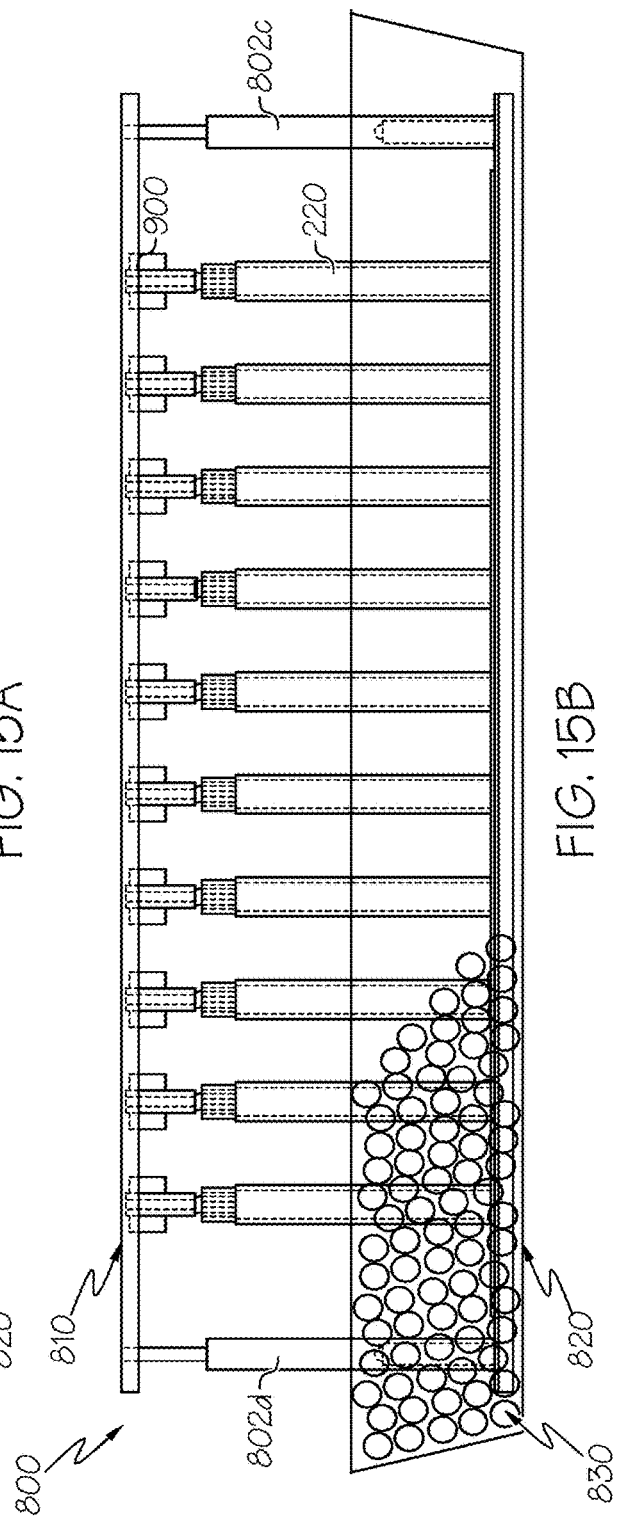

NERVE GAP

NERVE AMPUTATION

NERVE TRANSFER

EXTRACELLULAR MATRIX SYSTEMS, DEVICES, AND METHODS OF DEPLOYMENT

RELATED APPLICATIONS

This application claims the benefit of U.S. Provisional Patent Application Ser. No. 62/954,813, entitled "Extracellular Matrix Systems, Devices and Methods of Deployment", filed Dec. 30, 2019, the content of which is incorporated herein by reference in its entirety for all purposes.

This application claims the benefit of U.S. Provisional Patent Application Ser. No. 63/085,797, entitled "Extracellular Matrix Systems, Devices and Methods of Deployment", filed Sep. 30, 2020, the content of which is incorporated herein by reference in its entirety for all purposes.

This application is related to:
- U.S. Pat. No. 8,361,503, Issued Jan. 29, 2013;
- U.S. Pat. No. 8,691,276, Issued Apr. 8, 2014;
- U.S. Pat. No. 9,737,635, Issued Aug. 22, 2017;
- U.S. Pat. No. 10,004,827, Issued Jun. 26, 2018;
- U.S. Pat. No. 10,179,192, Issued Jan. 15, 2019;
- U.S. Pat. No. 10,213,526, Issued Feb. 26, 2019;
- U.S. Pat. No. 10,729,813, Issued Aug. 4, 2020; and
- U.S. Pat. No. 10,772,989, Issued Sep. 15, 2020;

the content of each of which is incorporated herein by reference in its entirety for all purposes.

This application is related to: U.S. patent application Ser. No. 16/992,442, entitled "Extracellular Matrix-Derived Gels and Related Methods", filed Jun. 4, 2018, published as US2019/0038803; U.S. patent application Ser. No. 16/238,826, entitled "Methods for Preparation of a Terminally Sterilized Hydrogel Derived from Extracellular Matrix", filed Jan. 3, 2019, published as US2019/374683; U.S. patent application Ser. No. 16/288,831, entitled "Extracellular Matrix-Derived Gels and Related Methods", filed Feb. 28, 2019, published as US2019/201581; U.S. patent application Ser. No. 16/911,909, entitled "Extracellular Matrix-Derived Gels and Related Methods", filed Jun. 25, 2020; U.S. patent application Ser. No. 16/992,442, entitled "Injectable Peripheral Nerve Specific Hydrogel", filed Aug. 13, 2020; and International PCT Patent Application Serial Number PCT/US2020/053570, entitled "Extracellular Matrix Devices and Methods of Manufacture", filed Sep. 30, 2020; the content of each of which is incorporated herein by reference in its entirety for all purposes.

FIELD OF THE INVENTIVE CONCEPTS

The present inventive concepts relate generally to improved nerve injury treatment systems, devices, and methods.

BACKGROUND

Peripheral nerve injuries (PNI) caused by laceration, compression, stretch, or iatrogenic injuries, such as those caused by tumor resection, have severe and wide-ranging impacts on the quality of life, productivity, and interpersonal relationships of those affected. For example, PNI in the upper extremities can prevent patients from performing basic daily activities (e.g. getting dressed, working, or feeding themselves), while facial nerve injuries can impede vocalization and are associated with social stigma and withdrawal. Existing FDA-approved nerve products are primarily indicated for use as passive support or to prevent complications (e.g. mechanical instability, neuroma, or donor site morbidity associated with autograft). None of these products has shown clinical improvement in functional outcomes.

Surgeons performing nerve repair often give their patients very poor prognoses and little hope. Nerve regeneration typically requires 3-18 months to complete and terminal functional recovery is often less than 50%.

There is a need for improved nerve injury treatment systems, devices, and methods.

SUMMARY

According to an aspect of the present inventive concepts, a system for treating a patient comprising: an extracellular matrix comprising tissue harvested from a tissue source; a neutralizing element; and a reconstituting element. The system can be configured to provide a therapeutic benefit to the patient.

In some embodiments, the neutralizing element and/or reconstituting element are configured to interact with the extracellular matrix, and the interaction causes a change to the extracellular matrix. The interaction can cause a physical change to the extracellular matrix. The interaction can cause a chemical change to the extracellular matrix. The neutralizing element can be configured to counteract a property of the extracellular matrix, and the property can be selected from the group consisting of: physical; mechanical; chemical; biological; and combinations thereof. The reconstituting element can be configured to modify a property of the extracellular matrix, and the property can be selected from the group consisting of: physical; mechanical; chemical; biological; and combinations thereof.

In some embodiments, the neutralizing element is configured to interact with the reconstituting element, and the interaction causes a change to the reconstituting element. The neutralizing element can be configured to counteract a property of the reconstituting element, and the property can be selected from the group consisting of: physical; mechanical; chemical; biological; and combinations thereof.

In some embodiments, the neutralizing element comprises a solution comprising sodium hydroxide (NaOH), phosphate-buffered saline (PBS), and/or water.

In some embodiments, the reconstituting element is configured to interact with the neutralizing element, and the interaction causes a change to the neutralizing element. The reconstituting element can be configured to change a property of the neutralizing element, and the property can be selected from the group consisting of: physical; mechanical; chemical; biological; shelf-life; and combinations thereof.

In some embodiments, the reconstituting element comprises water.

In some embodiments, the neutralizing element and the reconstituting element comprise a co-solution.

In some embodiments, the extracellular matrix tissue comprises at least one of sensory nerve tissue, motor nerve tissue, or mixed nerve tissue. The extracellular matrix tissue can further comprise autonomic nerve tissue. The extracellular matrix tissue can further comprise spinal cord nerve tissue. The extracellular matrix tissue can further comprise dorsal root ganglia tissue and/or ventral root ganglia tissue. The extracellular matrix tissue can further comprise sciatic nerve tissue.

In some embodiments, the extracellular matrix is constructed and arranged as a scaffold configured to provide structural support at the treatment site. The scaffold can be configured to provide structural support for a process selected from the group consisting of: cell attachment; cell migration; cell alignment; cell proliferation; cell differentiation; cell phenotype; cell selection; cell development; gene expression; protein expression; protein secretion; tissue development; tissue alignment; and combinations thereof.

In some embodiments, the extracellular matrix is configured to exhibit pharmacological and/or biological properties. The pharmacological and/or biological properties can be configured to promote a process selected from the group consisting of: immunomodulatory action; revascularization; cell chemotaxis; cell development; gene expression; protein expression; protein secretion; nerve tissue deposition; and combinations of these.

In some embodiments, the system can further comprise one or more vials configured to store at least one of the extracellular matrix, neutralizing element, or reconstituting element.

In some embodiments, the system can further comprise one or more fluid delivery devices configured to receive and/or expel at least one of the extracellular matrix, neutralizing element, or reconstituting element. The one or more fluid delivery devices can comprise a syringe.

In some embodiments, the system can further comprise an implant configured to provide one, two, or more channels between two or more anatomical elements. The implant can comprise a conduit. The implant can comprise an artificial and/or natural conduit. The implant can be configured to receive a volume of the extracellular matrix. The implant can comprise the extracellular matrix.

In some embodiments, the system can further comprise a support assembly for manufacturing an implant. The implant can comprise a conduit. The implant can comprise the extracellular matrix.

According to another aspect of the present inventive concepts, a method for manufacturing a conduit comprising: inserting an extracellular matrix into a support assembly; lyophilizing the extracellular matrix within the support assembly; and selectively removing the lyophilized extracellular matrix within the support assembly to create one or more lumens therethrough.

According to another aspect of the present inventive concepts, a method for treating a patient comprising: deploying a device comprising an extracellular matrix at a deposit site in the patient. The device can be configured to provide a therapeutic benefit at a treatment site.

In some embodiments, the device is deployed into at least a portion of a nerve. The device can be deployed intra-mesoneurium and/or peri-mesoneurium. The device can be deployed intra-epineurium. The device can be deployed sub-epineurium. The device can be deployed sub-endoneurium. The device can be deployed intra-epineurium and sub-endoneurium. The device can be deployed sub-epineurium at one, two, or more discrete locations. The device can be deployed intra-mesoneurium, peri-mesoneurium, and/or intra-epineurium at one, two, or more discrete locations. The device can be deployed intra-mesoneurium, peri-mesoneurium, and/or intra-epineurium at one, two, or more discrete locations along a length and/or circumference of the nerve. The device can be deployed along a length of an epineural window.

In some embodiments, the device is deployed to surround at least a portion of a nerve.

In some embodiments, the device is deployed into at least a portion of a nerve, and the device is deployed to surround at least a portion of the nerve.

According to another aspect of the present inventive concepts, a system for treating a patient comprising a nerve graft-conduit combination comprising tissue derived from a tissue source. The system can be configured to provide a therapeutic benefit to the patient.

According to another aspect of the present inventive concepts, a method for treating a patient comprising: deploying a device comprising a nerve graft-conduit combination at a deposit site in the patient. The device can be configured to provide a therapeutic benefit at a treatment site.

The technology described herein, along with the attributes and attendant advantages thereof, will best be appreciated and understood in view of the following detailed description taken in conjunction with the accompanying drawings in which representative embodiments are described by way of example.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIGS. 4A and B illustrate a perspective view and end view of a support assembly for manufacturing a conduit comprising an extracellular matrix, respectively, consistent with the present inventive concepts.

FIGS. 13A-J illustrate cross-sectional and/or side views of a nerve comprising an extracellular matrix, consistent with the present inventive concepts.

FIGS. 15, 15A, and 15B illustrate an exploded view of a syringe holding apparatus, a side view of the syringe holding apparatus in an open configuration, and a side view of the syringe holding apparatus in a closed configuration, respectively, consistent with the present inventive concepts.

DETAILED DESCRIPTION OF THE DRAWINGS

Figure 1:
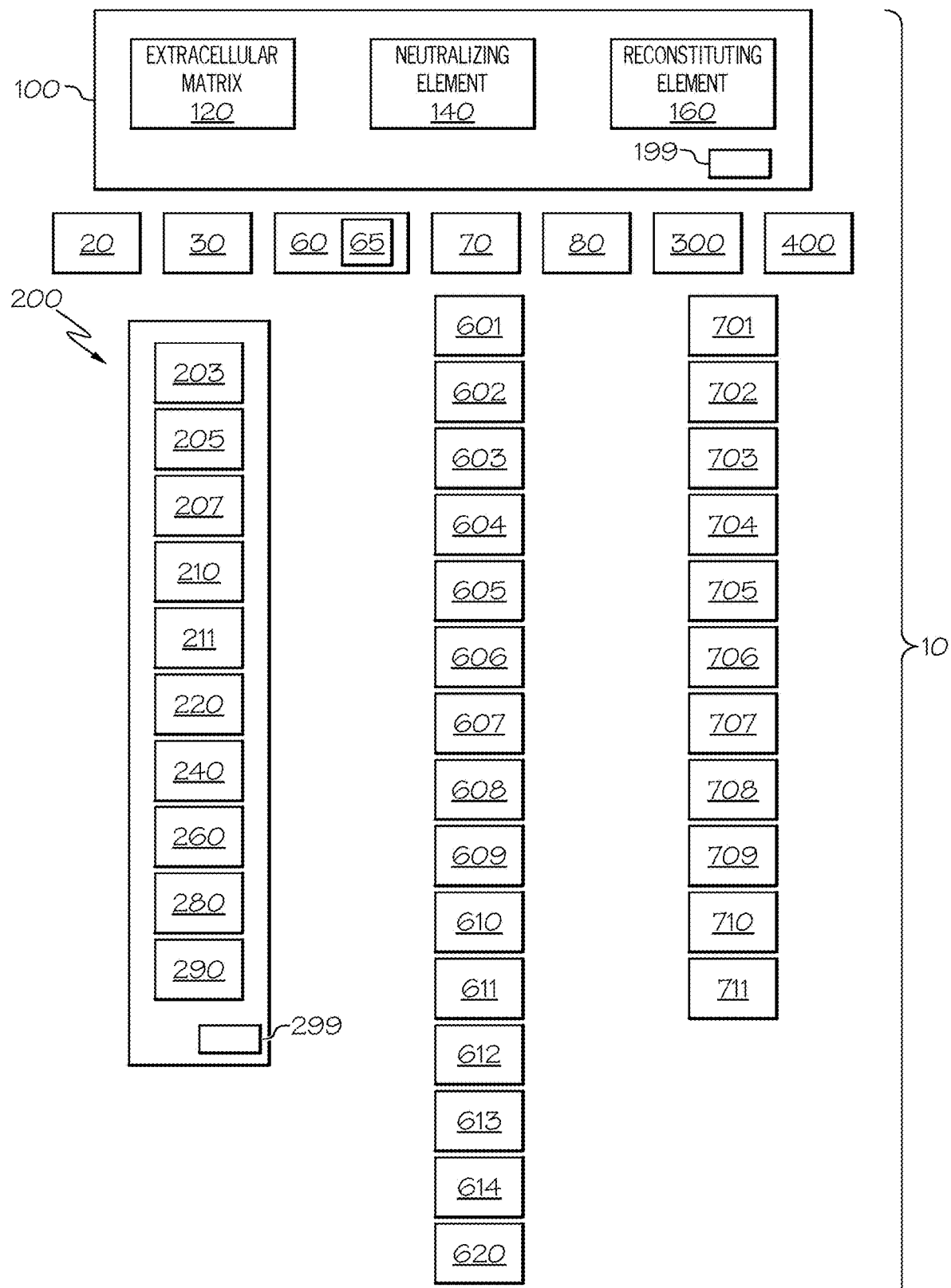
FIG. 1 illustrates a schematic view of a system for producing and deploying a medical device comprising an extracellular matrix, consistent with the present inventive concepts.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third, etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer, or section. Thus, a first limitation, element, component, region, layer, or section discussed below could be termed a second limitation, element, component, region, layer, or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element);

positioned on an external and/or internal surface of the second element; and combinations of one or more of these.

As used herein, the term "proximate", when used to describe proximity of a first component or location to a second component or location, is to be taken to include one or more locations near to the second component or location, as well as locations in, on and/or within the second component or location. For example, a component positioned proximate an anatomical site (e.g. a target tissue location), shall include components positioned near to the anatomical site, as well as components positioned in, on and/or within the anatomical site.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence. Correspondingly, the terms "prevent", "preventing", and "prevention" shall include the acts of "reduce", "reducing", and "reduction", respectively.

The term "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

The term "one or more", where used herein can mean one, two, three, four, five, six, seven, eight, nine, ten, or more, up to any number.

The terms "and combinations thereof" and "and combinations of these" can each be used herein after a list of items that are to be included singly or collectively. For example, a component, process, and/or other item selected from the group consisting of: A; B; C; and combinations thereof, shall include a set of one or more components that comprise: one, two, three or more of item A; one, two, three or more of item B; and/or one, two, three, or more of item C.

In this specification, unless explicitly stated otherwise, "and" can mean "or", and "or" can mean "and". For example, if a feature is described as having A, B, or C, the feature can have A, B, and C, or any combination of A, B, and C. Similarly, if a feature is described as having A, B, and C, the feature can have only one or two of A, B, or C.

As used herein, when a quantifiable parameter is described as having a value "between" a first value X and a second value Y, it shall include the parameter having a value of: at least X, no more than Y, and/or at least X and no more than Y. For example, a length of between 1 and 10 shall include a length of at least 1 (including values greater than 10), a length of less than 10 (including values less than 1), and/or values greater than 1 and less than 10.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

As used herein, the term "threshold" refers to a maximum level, a minimum level, and/or range of values correlating to a desired or undesired state. In some embodiments, a system parameter is maintained above a minimum threshold, below a maximum threshold, within a threshold range of values, and/or outside a threshold range of values, such as to cause a desired effect (e.g. efficacious therapy) and/or to prevent or otherwise reduce (hereinafter "prevent") an undesired event (e.g. a device and/or clinical adverse event). In some embodiments, a system parameter is maintained above a first threshold (e.g. above a first temperature threshold to cause a desired therapeutic effect to tissue) and below a second threshold (e.g. below a second temperature threshold to prevent undesired tissue damage). In some embodiments, a threshold value is determined to include a safety margin, such as to account for patient variability, system variability, tolerances, and the like. As used herein, "exceeding a threshold" relates to a parameter going above a maximum threshold, below a minimum threshold, within a range of threshold values and/or outside of a range of threshold values.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

As used herein, the term "functional element" is to be taken to include one or more elements constructed and arranged to perform a function. A functional element can comprise a sensor and/or a transducer. In some embodiments, a functional element is configured to generate and/or deliver energy and/or otherwise treat tissue (e.g. a functional element configured as a treatment element). Alternatively or additionally, a functional element (e.g. a functional element comprising a sensor) can be configured to record one or more parameters, such as a patient physiologic parameter; a patient anatomical parameter (e.g. a tissue geometry parameter); a patient environment parameter; and/or a system parameter. In some embodiments, a sensor or other functional element is configured to perform a diagnostic function (e.g. to gather data used to perform a diagnosis). In some embodiments, a functional element is configured to perform a therapeutic function (e.g. to deliver therapeutic energy and/or a therapeutic agent). In some embodiments, a functional element comprises one or more elements constructed and arranged to perform a function selected from the group consisting of: deliver energy; extract energy (e.g. to cool a component); deliver a drug or other agent; manipulate a system component or patient tissue; record or otherwise sense a parameter such as a patient physiologic parameter or a system parameter; and combinations of one or more of these. A functional element can comprise a fluid and/or a fluid delivery system. A functional element can comprise a reservoir, such as an expandable balloon or other fluid-maintaining reservoir. A "functional assembly" can comprise an assembly constructed and arranged to perform a function, such as a diagnostic and/or therapeutic function. A functional assembly can comprise an expandable assembly. A functional assembly can comprise one or more functional elements.

As used herein, the term "fluid" can refer to a liquid, gas, gel, or any flowable material, such as a material which can be propelled through a lumen and/or opening.

It is appreciated that certain features of the present inventive concepts, which are, for clarity, described in the context of separate embodiments, may also be provided in combination in a single embodiment. Conversely, various features of the present inventive concepts which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the present inventive concepts have been simplified to focus on elements that are relevant for a clear understanding of the present inventive concepts, while eliminating, for purposes of clarity, other elements that those of ordinary skill in the art will appreciate may also comprise a portion of the present inventive concepts. However, because such elements are well known in the art, and because they do not necessarily facilitate a better understanding of the present inventive concepts, a description of such elements is not provided herein.

Terms defined in the present disclosure are only used for describing specific embodiments of the present disclosure and are not intended to limit the scope of the present disclosure. Terms provided in singular forms are intended to include plural forms as well, unless the context clearly indicates otherwise. All of the terms used herein, including technical or scientific terms, have the same meanings as those generally understood by an ordinary person skilled in the related art, unless otherwise defined herein. Terms defined in a generally used dictionary should be interpreted as having meanings that are the same as or similar to the contextual meanings of the relevant technology and should not be interpreted as having ideal or exaggerated meanings, unless expressly so defined herein. In some cases, terms defined in the present disclosure should not be interpreted to exclude the embodiments of the present disclosure.

Provided herein are improved nerve injury treatment systems, devices, and methods.

Referring now to FIG. 1, a schematic view of a system for producing and deploying a medical device comprising an extracellular matrix is illustrated, consistent with the present inventive concepts. System 10 comprises medical device 100 shown, as well as various components used to manufacture, package, sterilize, and/or deploy device 100. Device 100 is configured to be deployed (e.g. injected, inserted, delivered, implanted, and the like) at one, two, or more "deposit sites", such as to provide a therapeutic benefit at one, two, or more "treatment sites". Each treatment site can comprise a location that is proximate to and/or remote from the associated deposit site. In some embodiments, a treatment site comprises a location that is relatively the same location as the associated deposit site. Device 100 can be deployed at the deposit site to promote, and/or otherwise support, tissue growth of a patient (e.g. support tissue growth and/or regeneration at locations proximate and/or remote from the deposit site). In some embodiments, device 100 is remodeled over time into native tissue of the patient. As used herein, the deposit site can comprise one, two, or more locations on and/or within the patient.

Figure 3A:
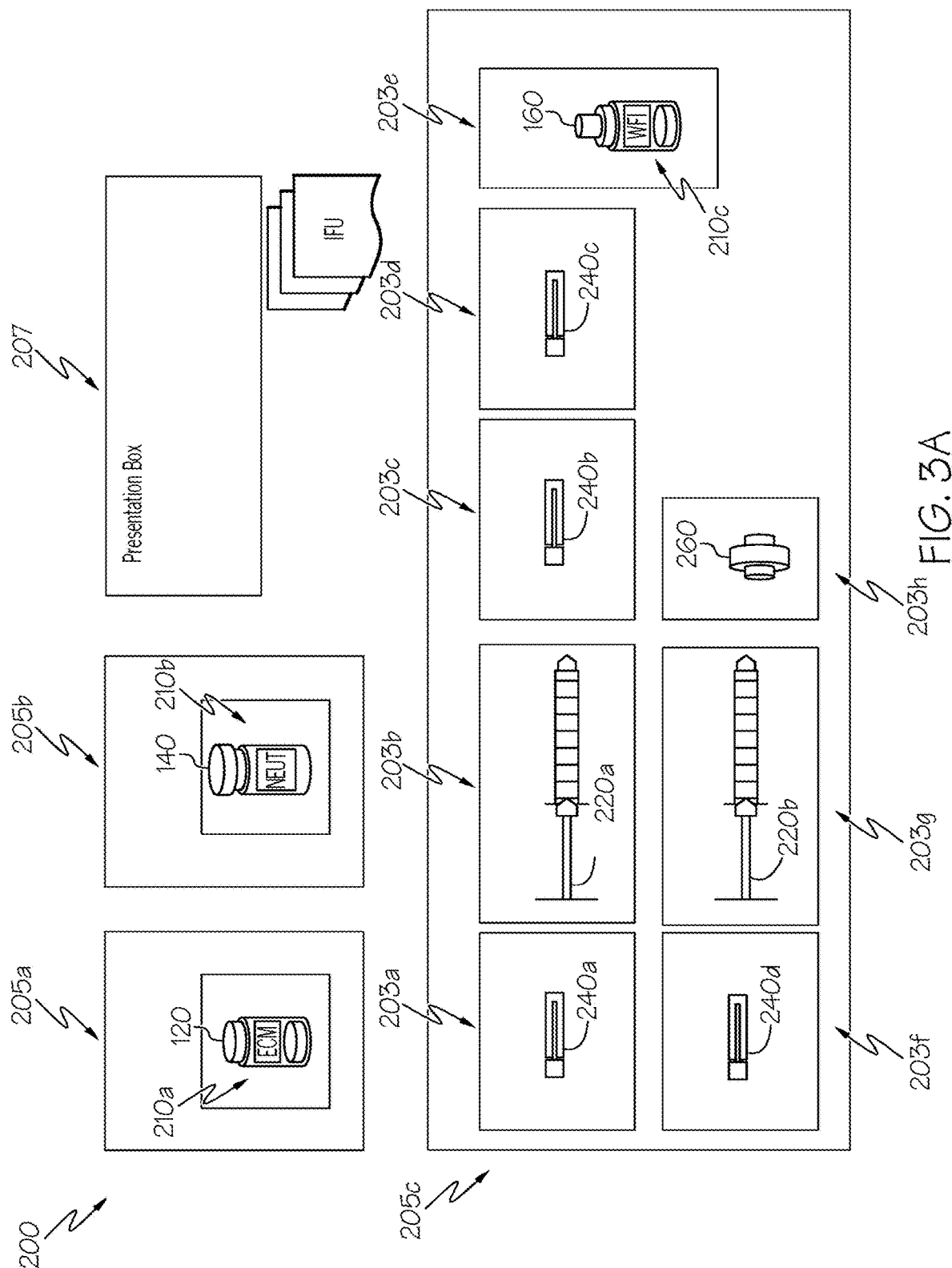
FIGS. 3A-P illustrate various deployment systems for a medical device comprising an extracellular matrix, consistent with the present inventive concepts.
Figure 3B:
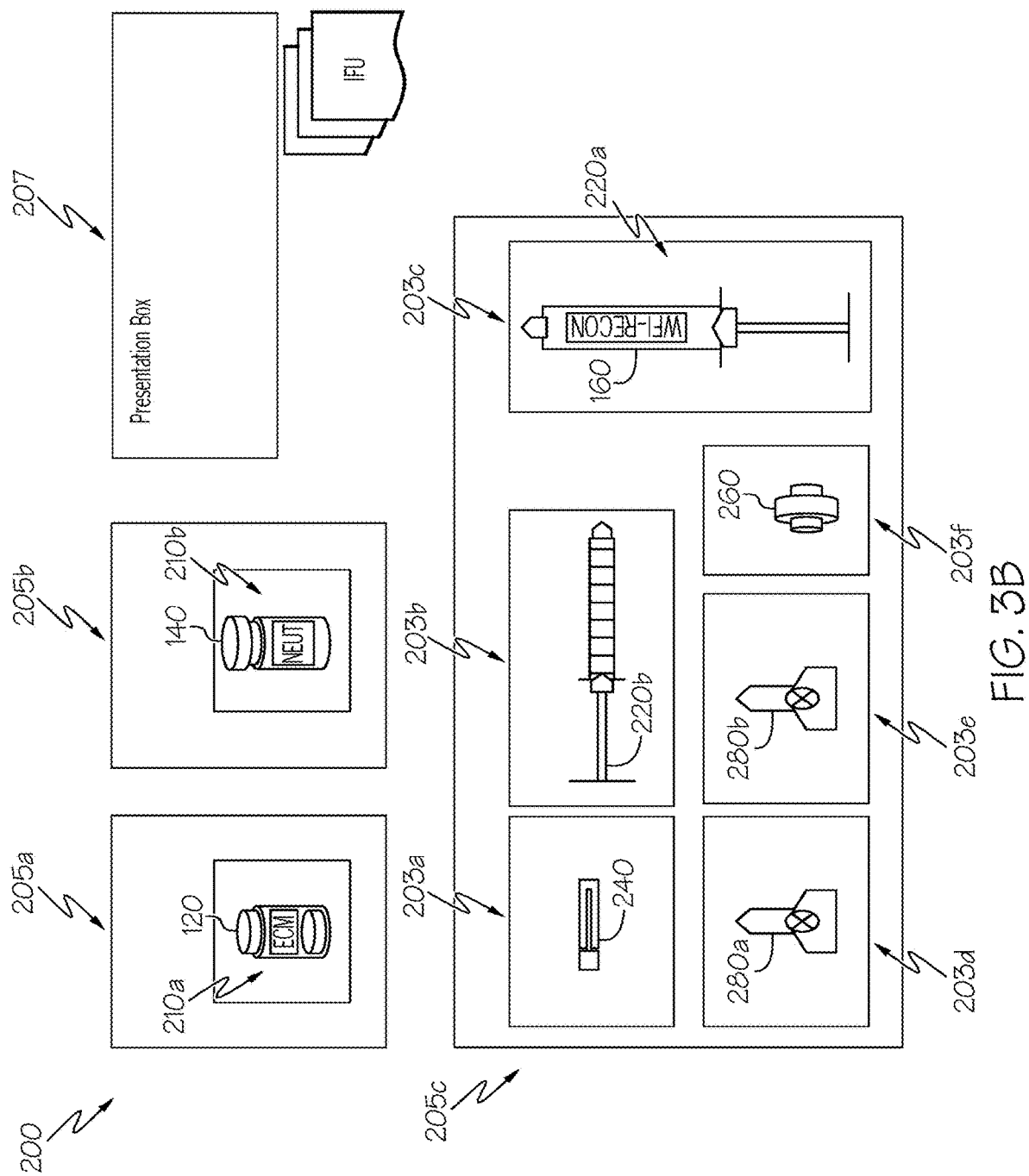
Figure 3C:
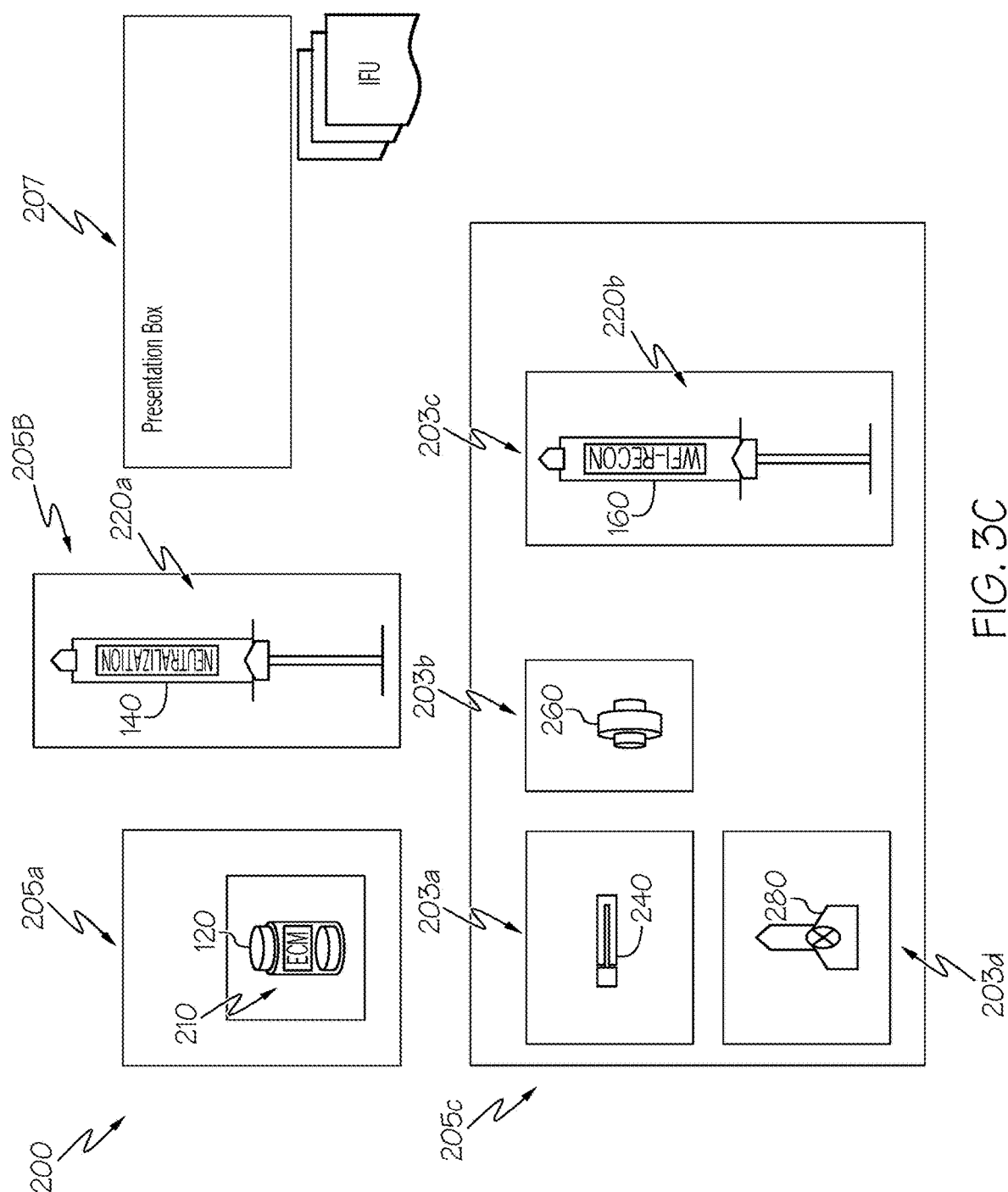
Figure 3D:
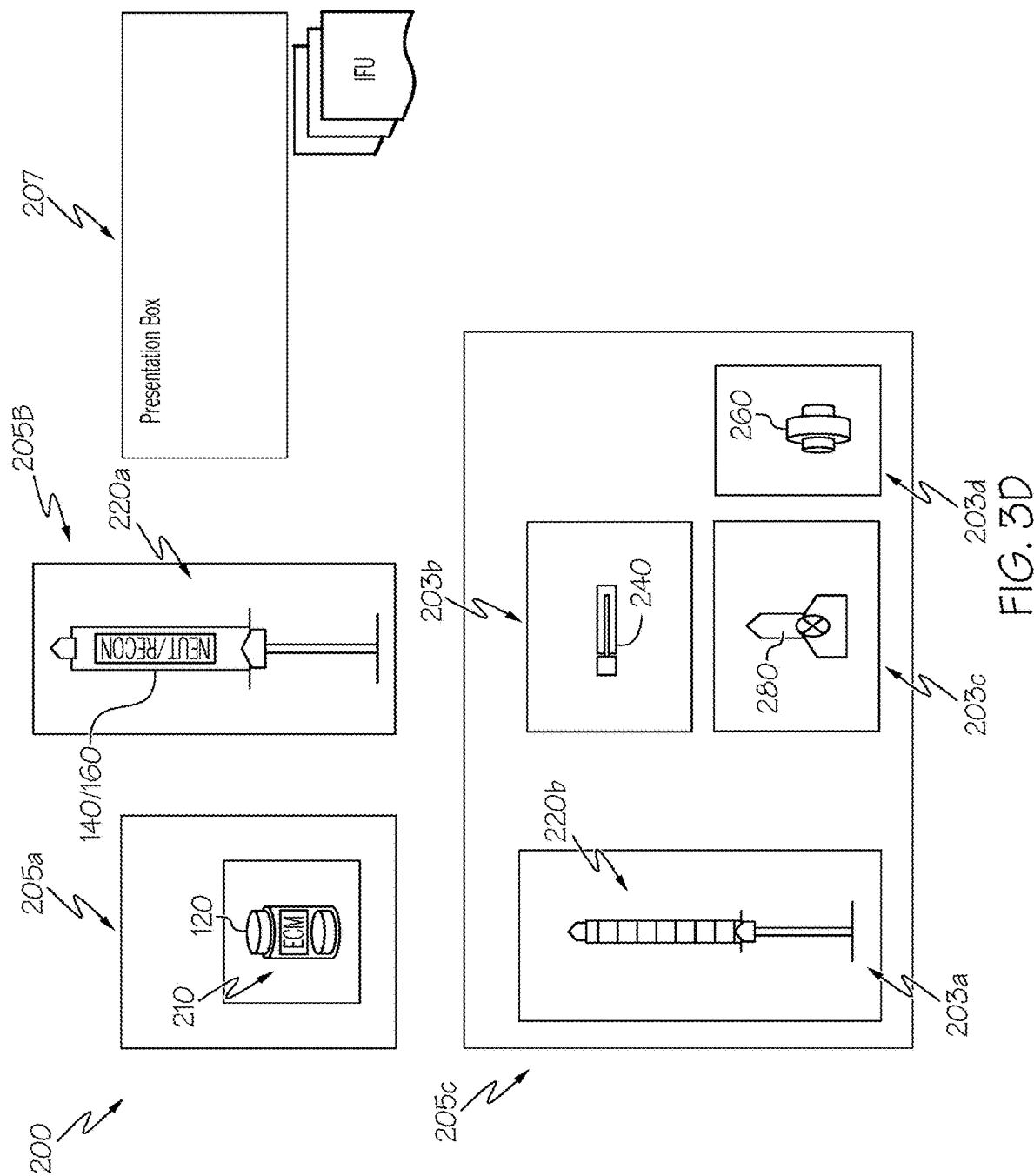
Figure 3E:
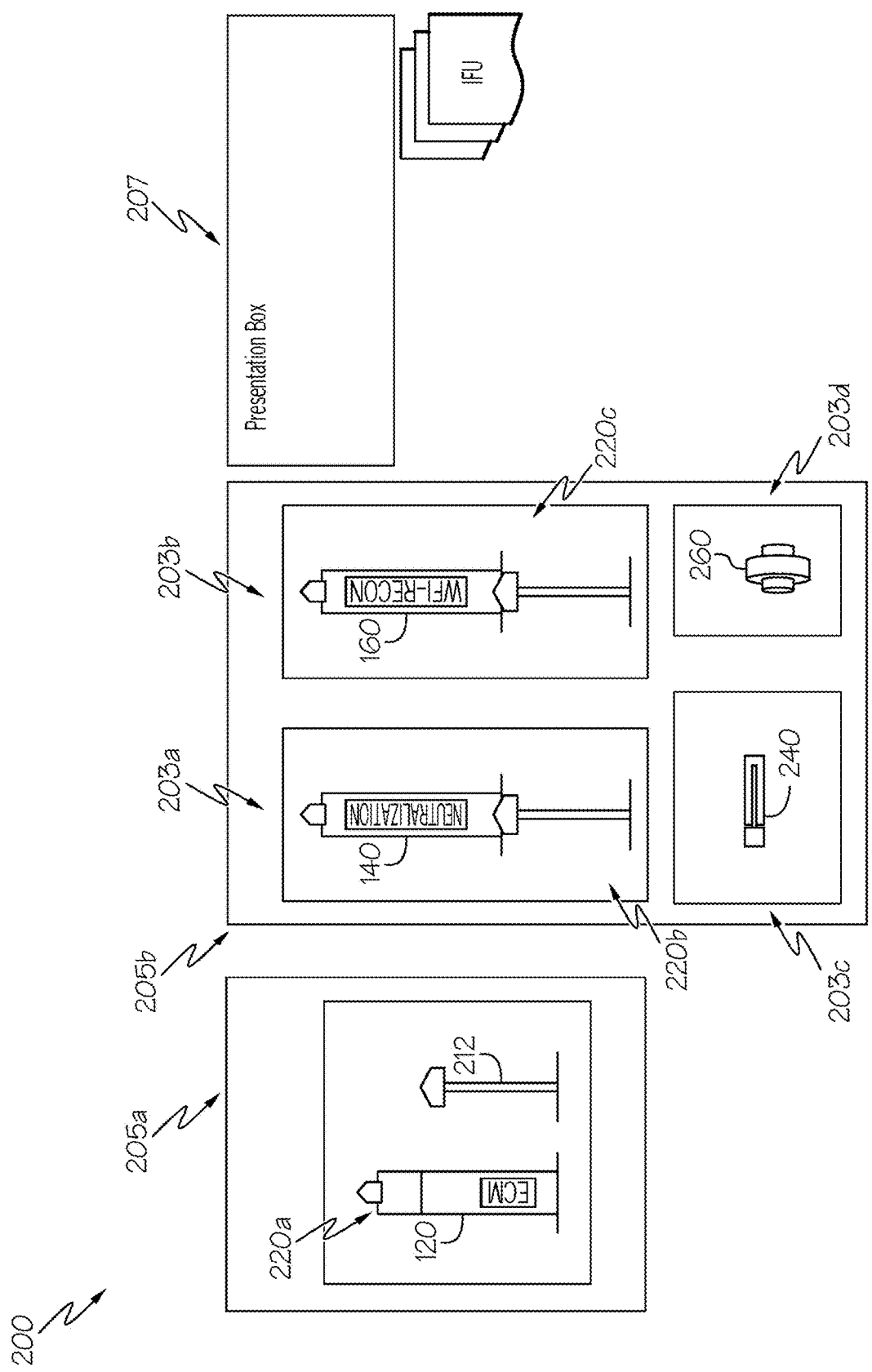
Figure 3F:
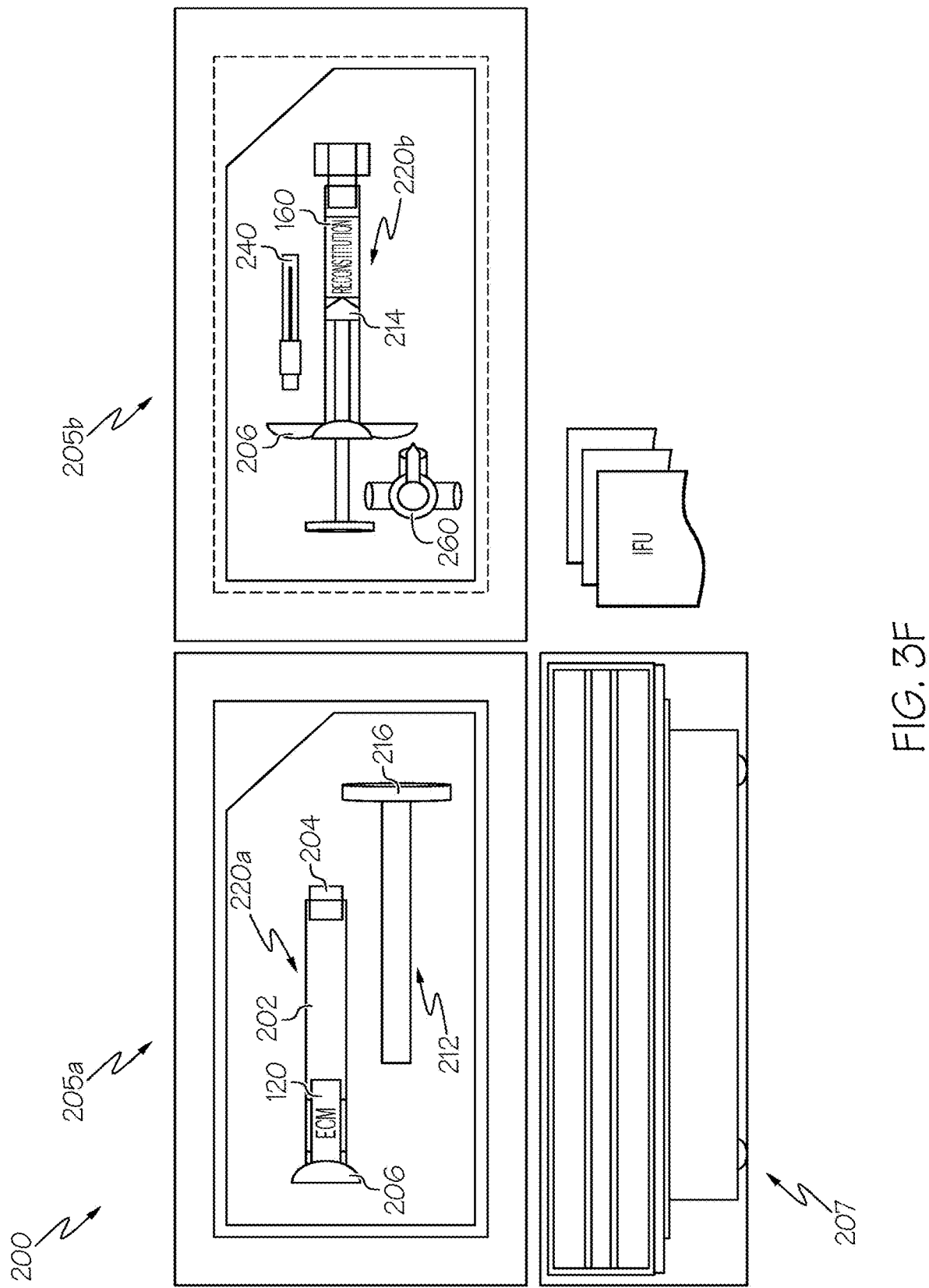
Figure 3G:
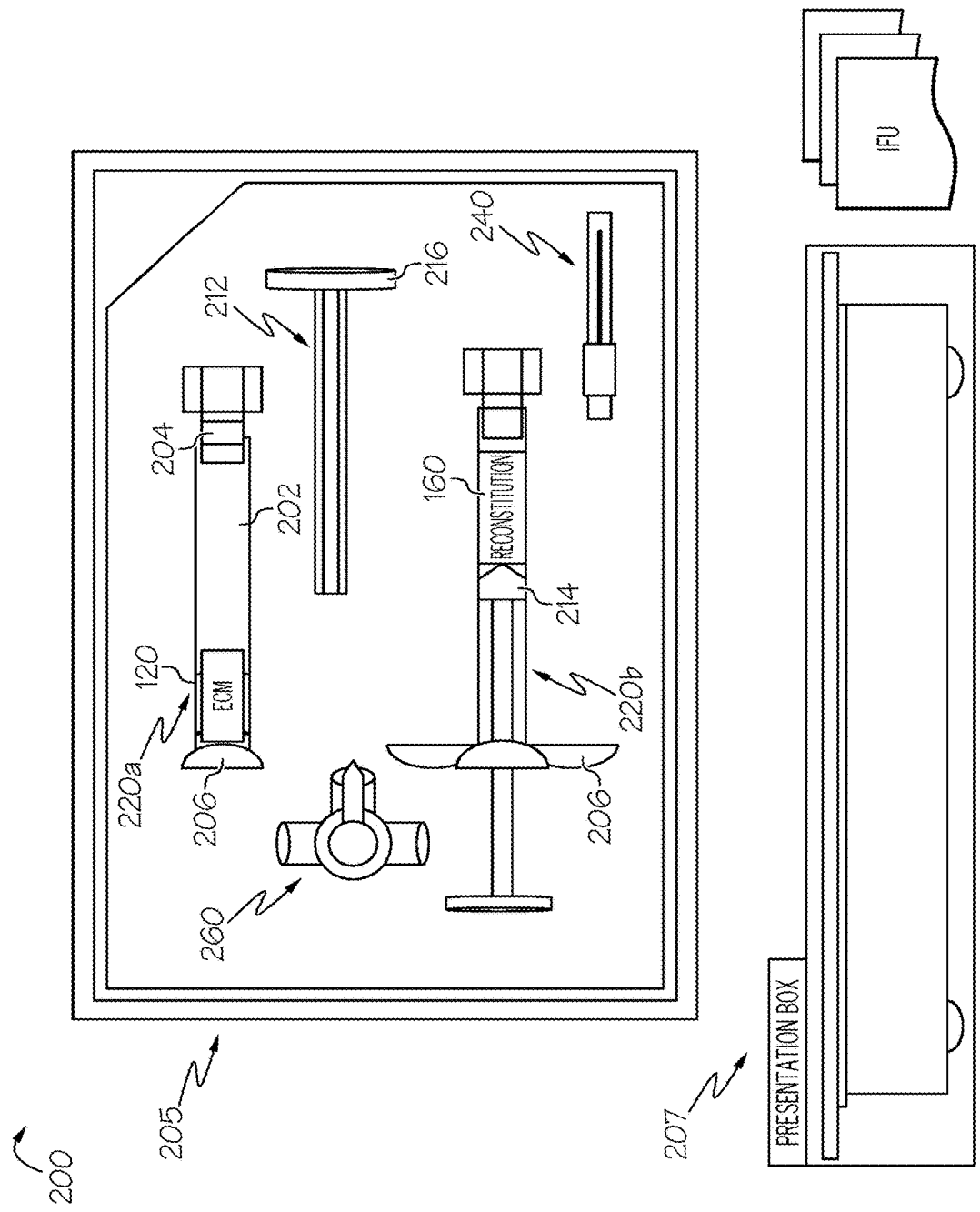
Figure 3H:
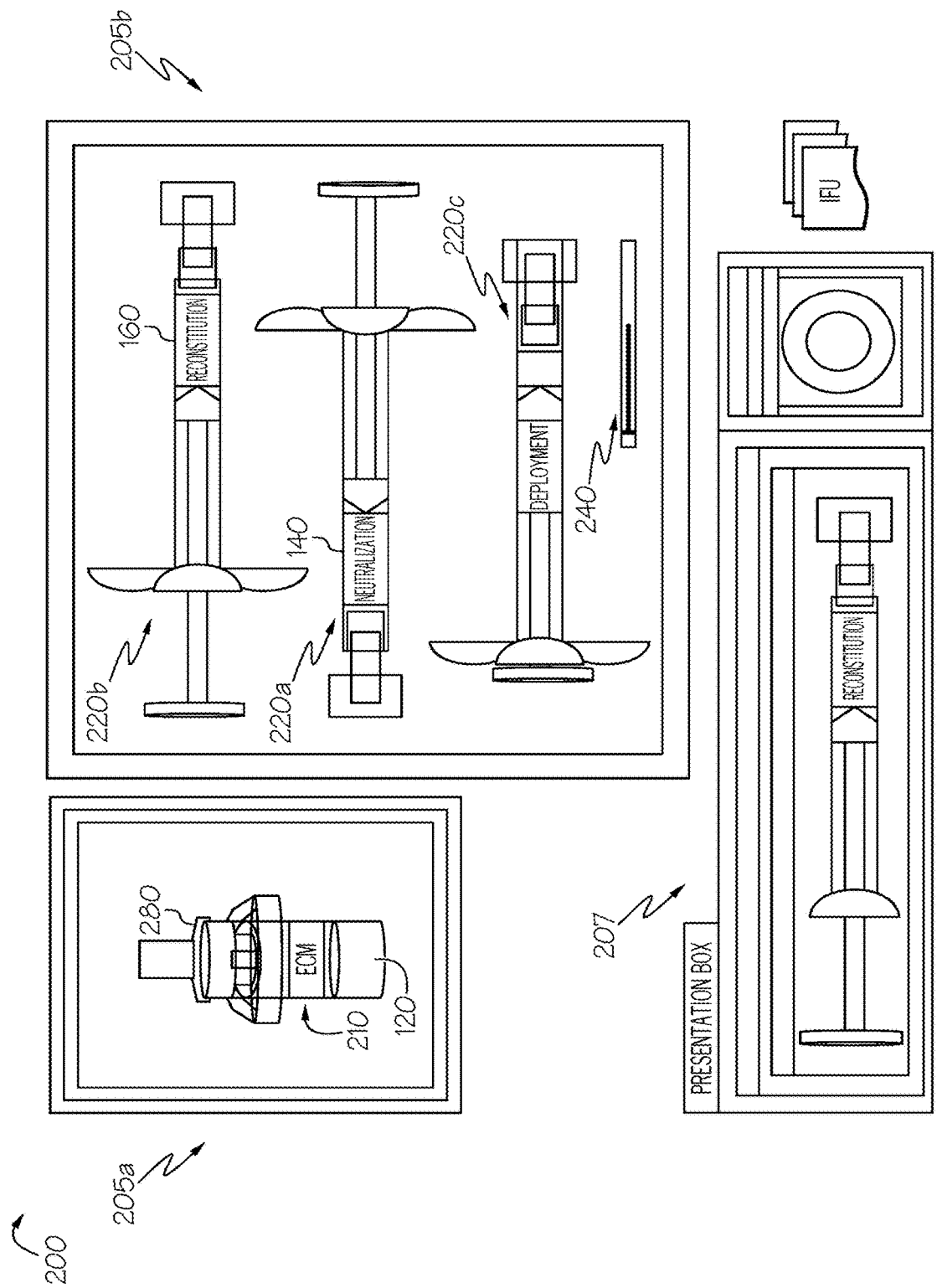
Figure 3I:
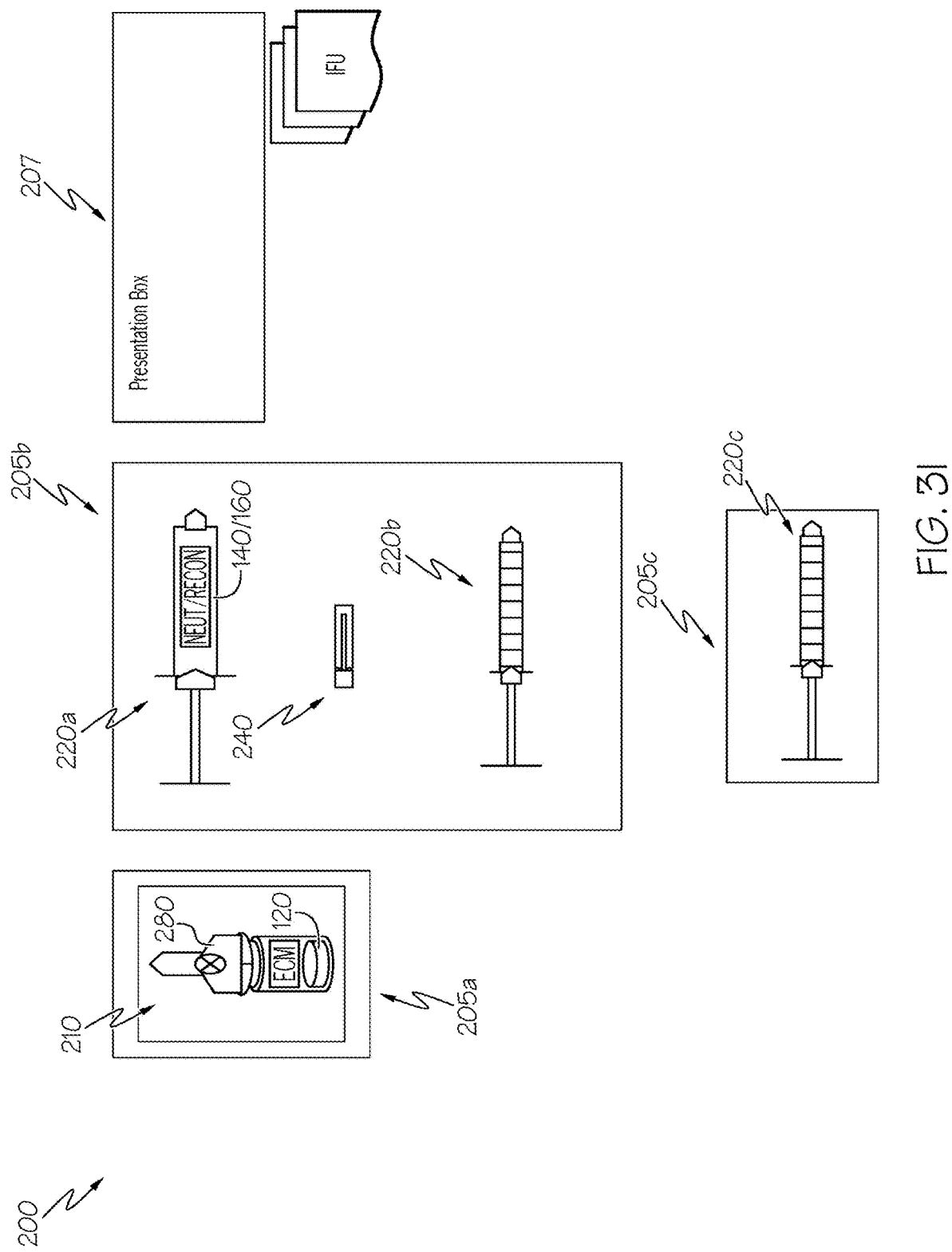
Figure 3J:
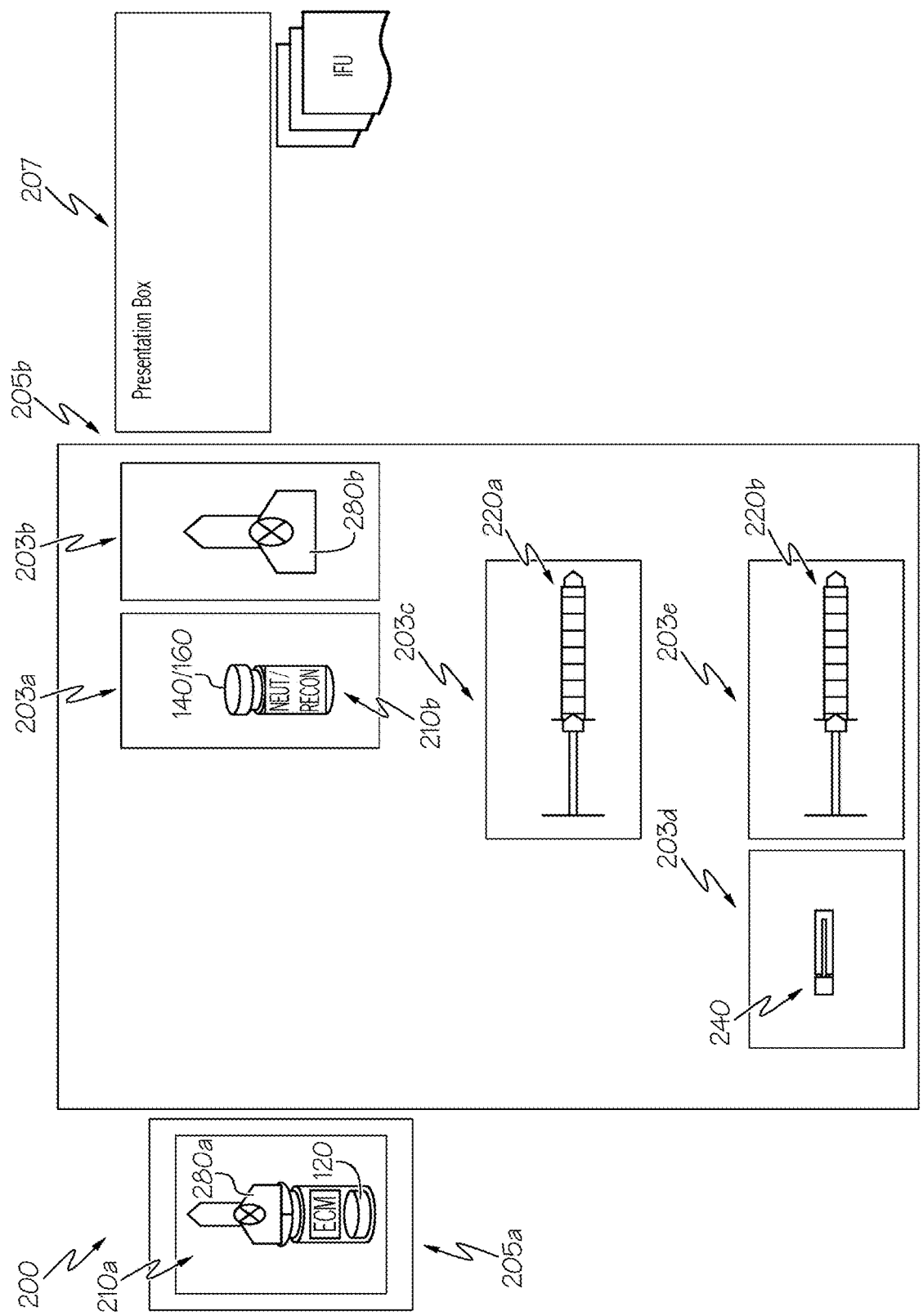
Figure 3K:
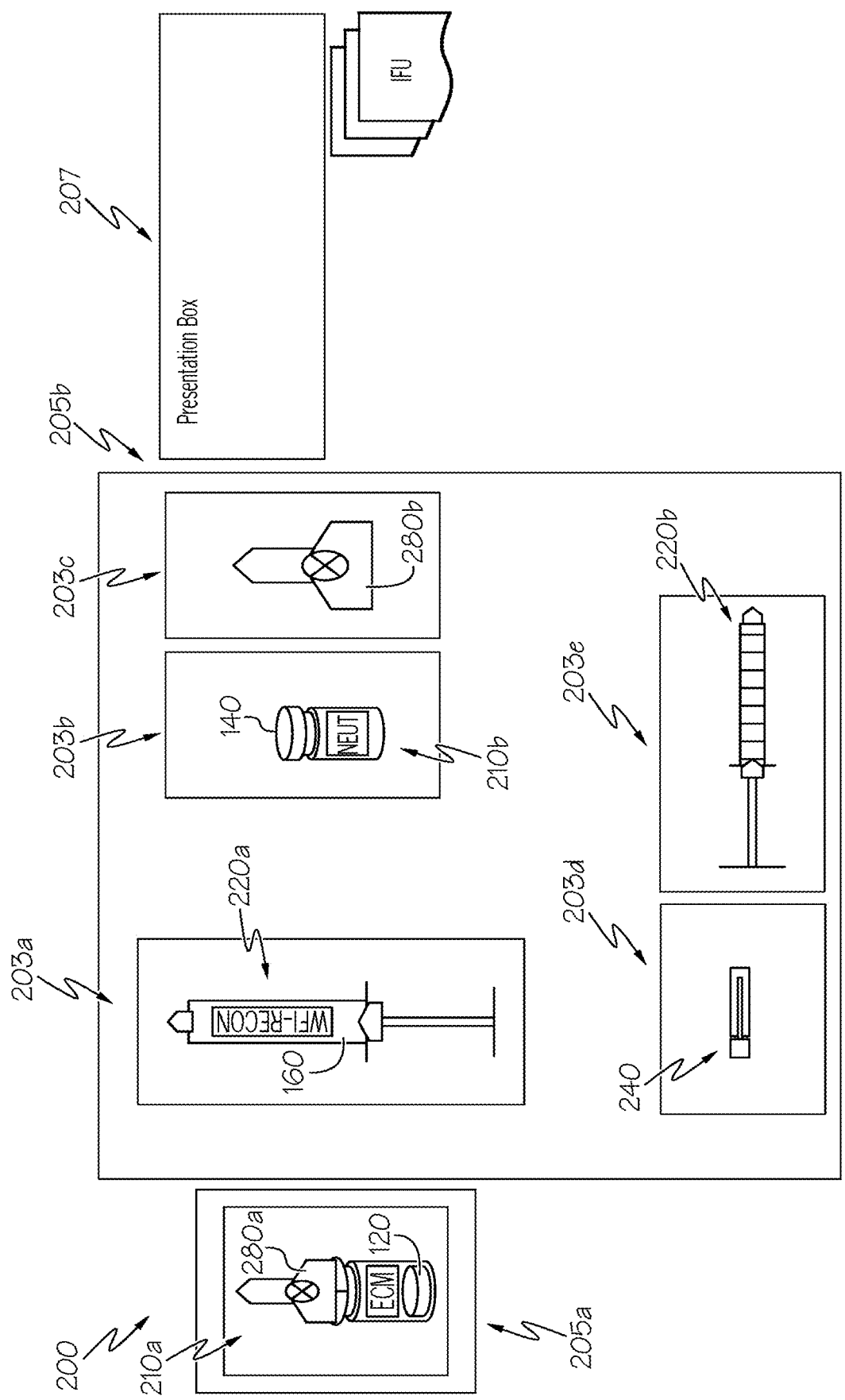
Figure 3L:
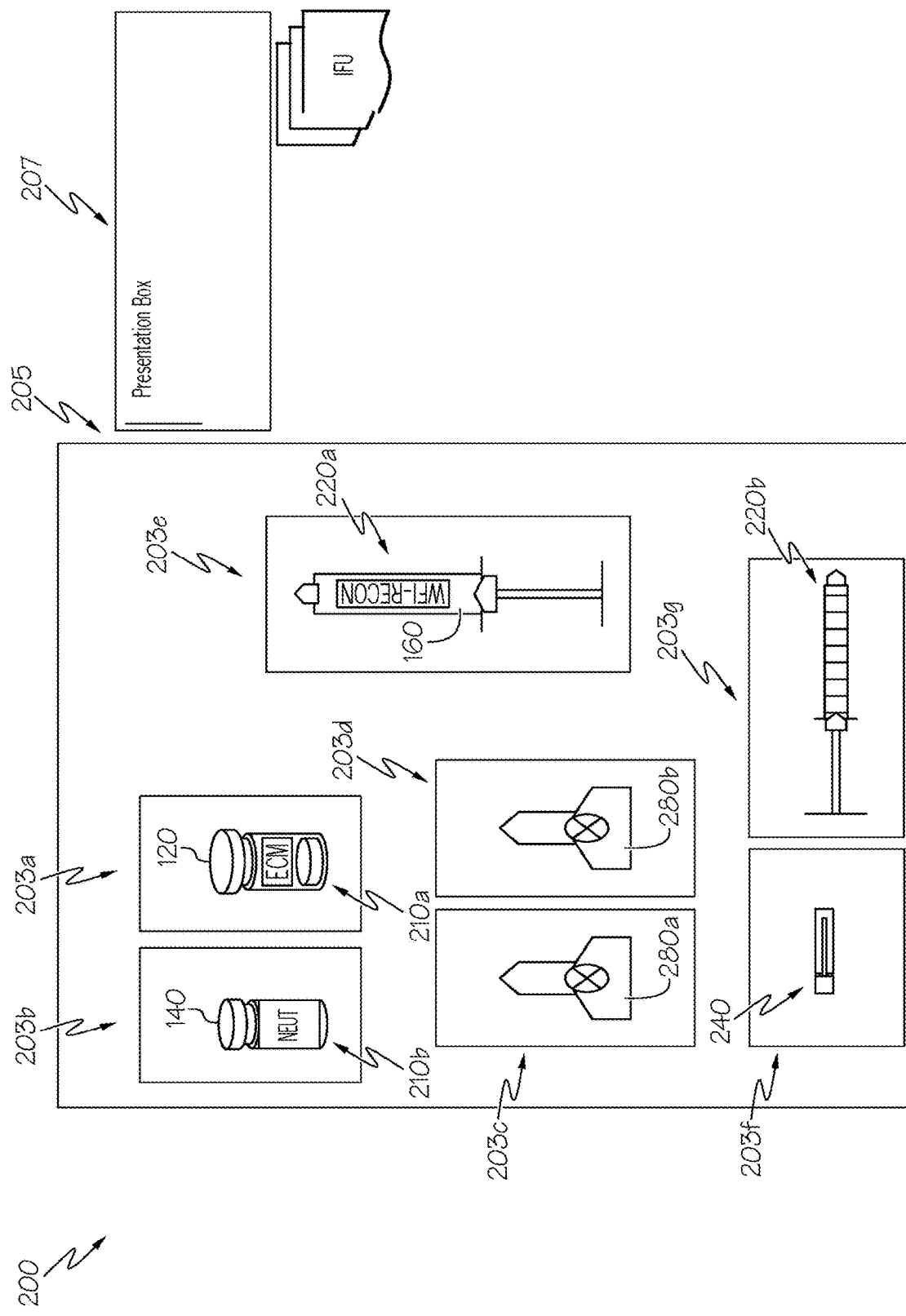
Figure 3M:
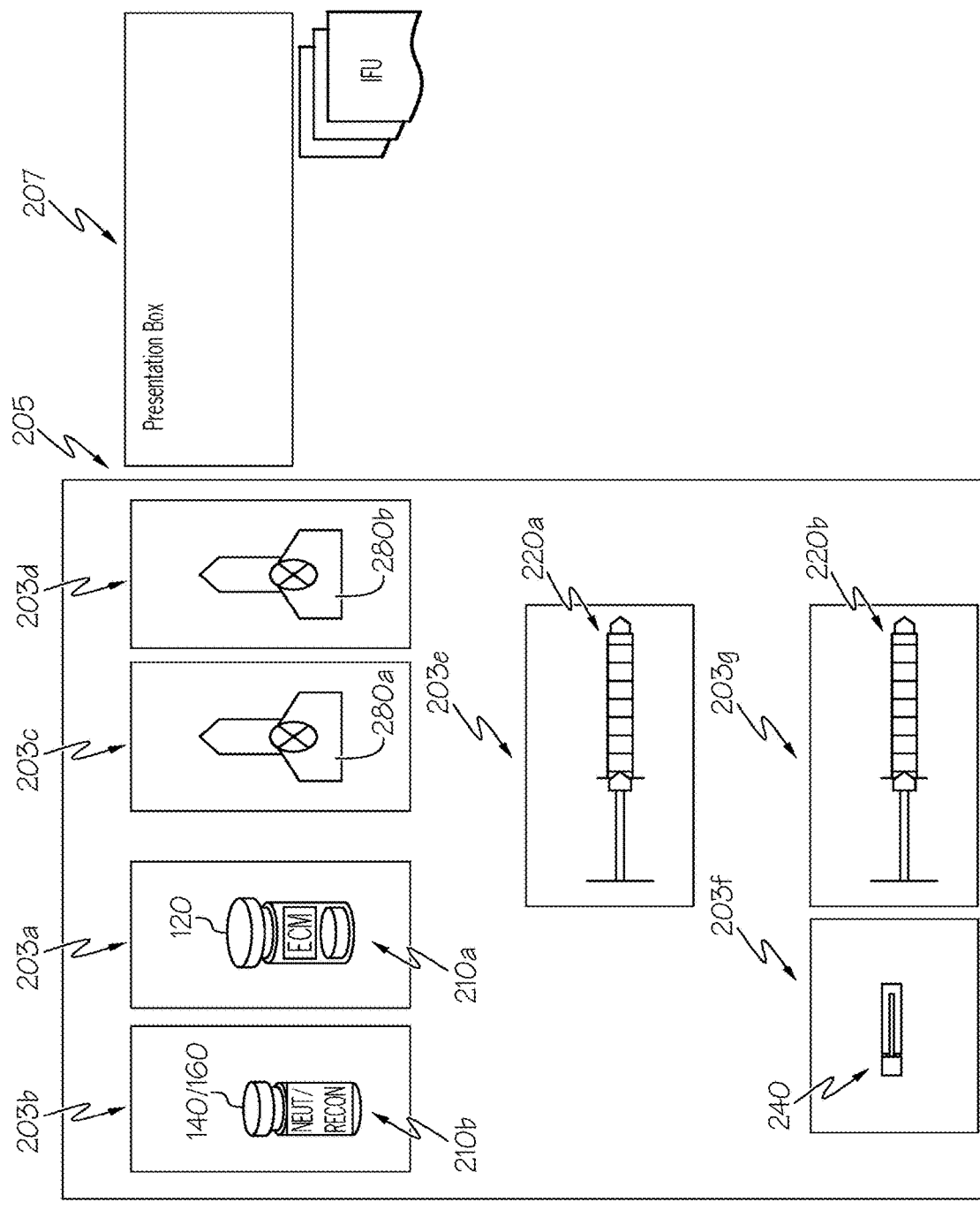
Figure 3N:
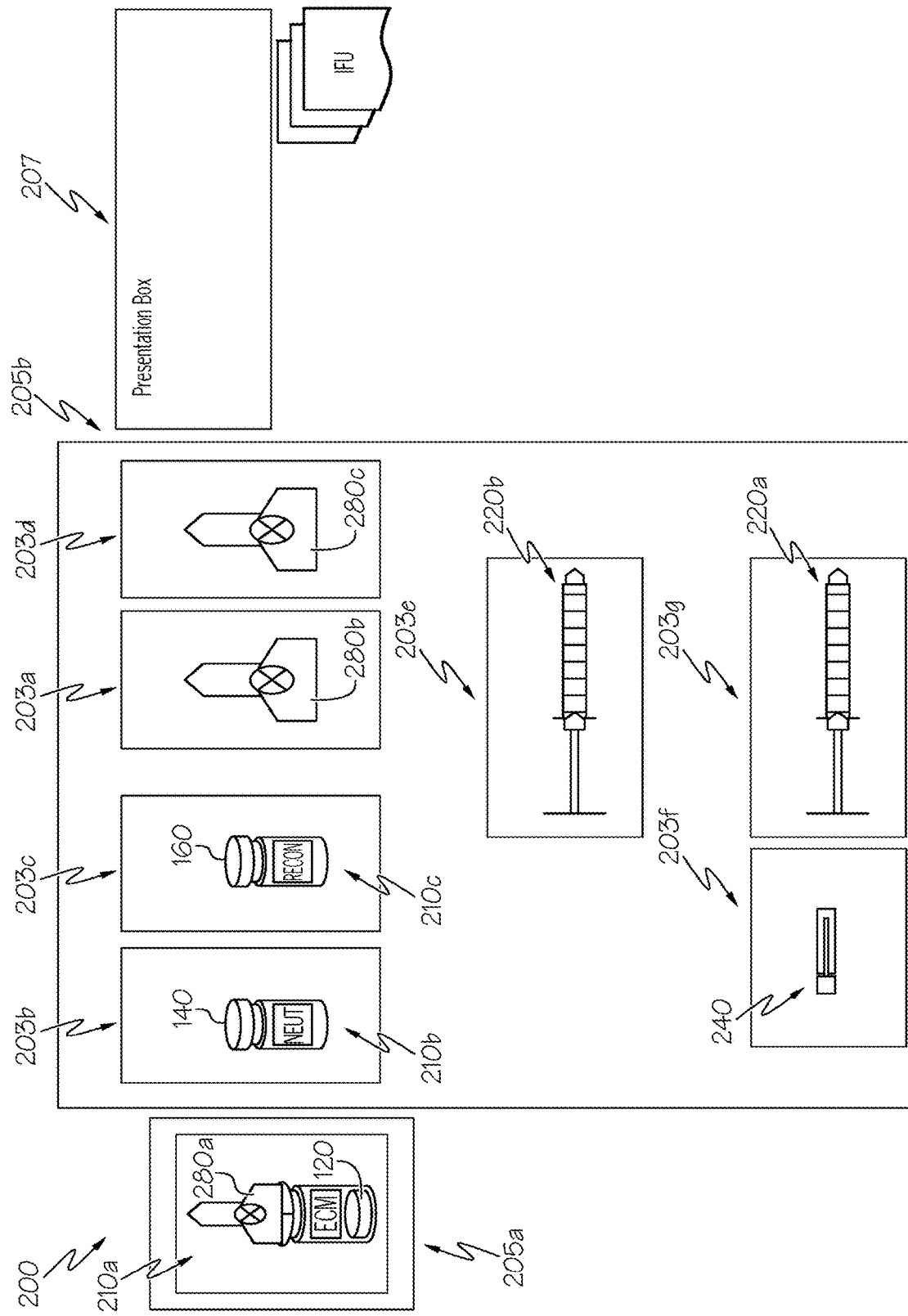
Figure 3P:
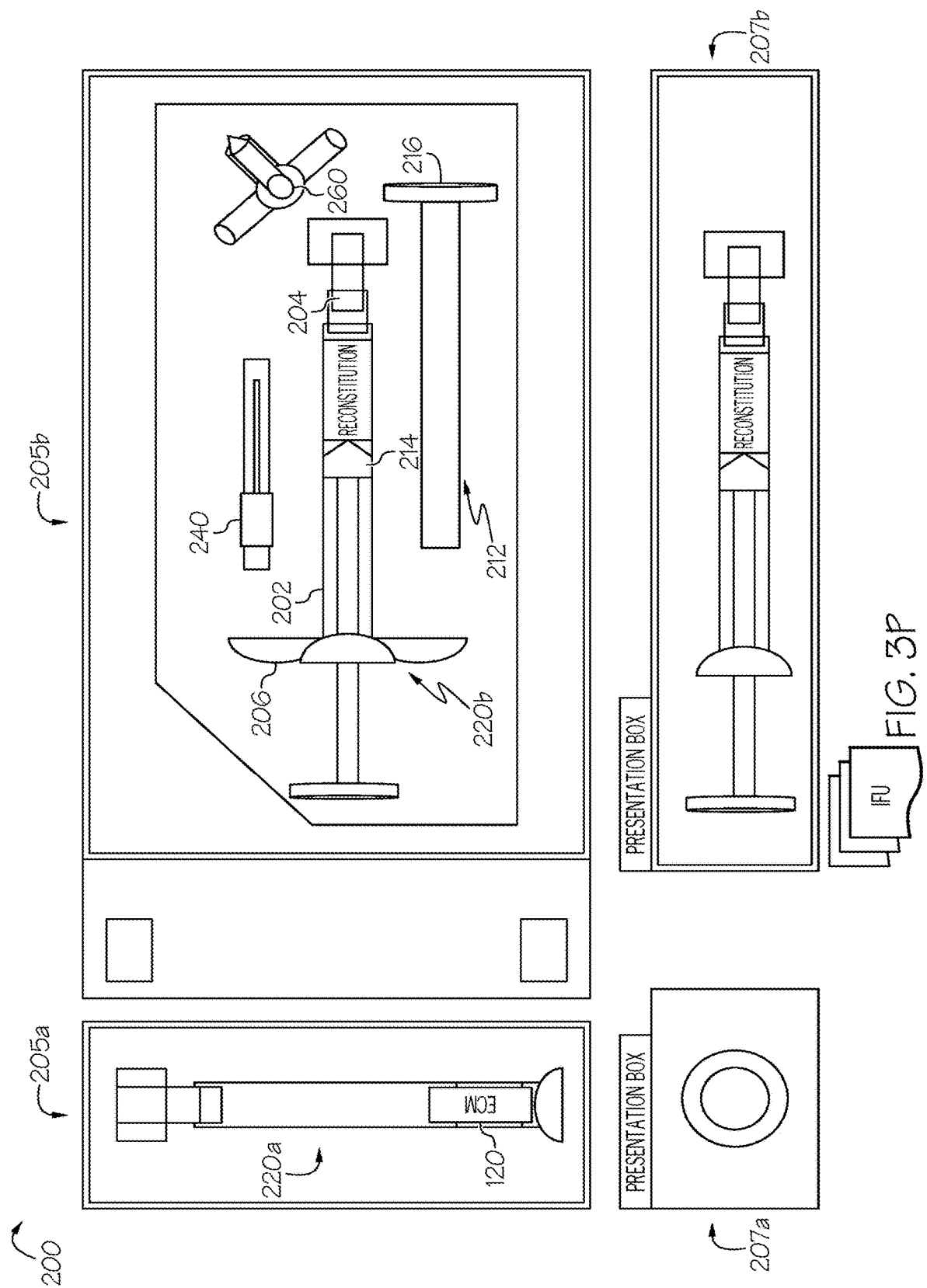

One, two, or more components of system 10 can be shipped, or otherwise provided, to a hospital, doctor's office, and/or other clinical setting in a deployment assembly 200, as described herein in reference to FIGS. 3A-P. Deployment assembly 200 can comprise one or more functional elements, functional element 299 shown, also as described herein in reference to FIGS. 3A-P.

Device 100 comprises a decellularized extracellular matrix, ECM 120 shown. ECM 120 can comprise structural and non-structural biomolecules, including, but not limited to, collagens, elastins, laminins, glycosaminoglycans, proteoglycans, antimicrobials, chemoattractant, cytokines, matrix bound vesicles, and growth factors. ECM 120 can be configured to promote and/or sustain the growth of tissue and/or associated tissue properties (e.g. structural proteins, growth factors, etc.) proximate to and/or remote from the deposit site. ECM 120 can be derived, or otherwise produced, from one, two, or more raw material 65 as described herein. In some embodiments, ECM 120 is derived from a raw material as described in applicant's co-pending International PCT Patent Application Serial Number PCT/US2020/053570, entitled "Extracellular Matrix Devices and Methods of Manufacture", filed Sep. 30, 2020. ECM 120 can comprise a concentration of native protein between 2 mg/mL and 50 mg/mL, such as a concentration between 5 mg/mL and 20 mg/mL, such as a concentration of approximately 10 mg/mL. The protein concentration can be configured to improve a parameter of ECM 120, such as to improve solubility, reconstitution, solution viscosity, solution injectability, solution mixability, gelation kinetics, working time, and gel mechanical/structural properties, such as storage modulus, stiffness, suture retention strength, microstructure, porosity, pore size distribution, liquid or gas permeability, cell penetration, cell phenotype, gene expression, protein expression, degradation rate, and/or durability.

Device 100 can further comprise a neutralizing element 140 and/or a reconstituting element 160, each configured to interact (e.g. physically, chemically interact) with ECM 120. In some embodiments, neutralizing element 140 and/or reconstituting element 160 interact with ECM 120 to cause a physical, mechanical, and/or chemical change to ECM 120 and/or other component of system 10. Neutralizing element 140 can be configured to counteract, or otherwise offset, a property (e.g. physical, mechanical, chemical property) of ECM 120, reconstituting element 160, and/or other component of system 10. Neutralizing element 140 can comprise an element selected from the group consisting of: water; buffer solutions, such as phosphate buffer solution (PBS), buffer amino acids (e.g. proline and histidine), or Tris buffers; base solutions, such as sodium hydroxide (NaOH); and combinations of these. Neutralizing element 140 can be configured to extend its ability to function as a neutralizing element over time (i.e. neutralizing element 140 shelf life). In some embodiments, the alteration of the buffer concentration of neutralizing element 140 prevents the natural pH drift over time of the solution due to the interaction with environmental $CO_2$. In some embodiments, ECM 120 comprises a fluid and neutralizing element 140 comprises a concentration of PBS that is configured to modify (e.g. increase, decrease) the mechanical strength of ECM 120, modify (e.g. increase, decrease) a gelation time of ECM 120, modify (e.g. increase, decrease) a gelation kinetics of ECM 120; and/or modify (e.g. increase, decrease) a gelation temperature of ECM 120. In some embodiments, neutralizing element 140 comprises a buffer solution in water with the components and ranges of concentration shown herebelow in Table 1:

TABLE 1

Buffer Solutions

| Buffer/<br>Neutralizing<br>Component | Range Conc (g/L) | Preferred Conc (g/L)<br>7.5-15 mg/mL |
|---|---|---|
| NaOH | 0.1-3.0 g/L | 0.5-1.01 |
| KCl | 0.01-1.0 g/L | 0.22 |
| $NaH_2PO_4$ | 0.1-1.5 g/L | 0.60 |
| NaCl | 0.3-9.0 g/L | 3.51 |
| $Na_2HPO_4$ | 0.1-10.0 g/L | 2.84 |

Reconstituting element 160 can be configured to change, or otherwise modify, a property (e.g. physical, chemical, mechanical, biological, and/or shelf-life property) of ECM 120, neutralizing element 140, and/or other component of system 10. For example, neutralizing element 140 comprising PBS can affect physical, chemical, mechanical, and/or biological properties of ECM 120. Reconstituting element 160 can comprise water. In some embodiments, reconstituting element 160 and neutralizing element 140 are combined to comprise a single reconstituting and neutralizing solution.

Raw material 65 can comprise sensory, motor, and/or mixed nerve tissue. In some embodiments, raw material 65 comprises autonomic nerve tissue. In some embodiments, raw material 65 comprises spinal cord nerve tissue. In some embodiments, raw material 65 comprises ventral and/or dorsal root ganglion. In some embodiments, raw material 65 comprises sciatic nerve tissue, such as bilateral sciatic nerves. Tissue harvested from multiple (e.g. two or more) nerve types can be pooled to provide a larger quantity and/or heterogenous raw material 65.

Raw material 65 can comprise tissue harvested from a tissue source 60 selected from the group consisting of: a mammal, such as pig, human, cow, horse, and the like; an amphibian, such as salamander (e.g. an axolotl) and the like; a chondrichthyan, such as shark and the like; reptile, such as chelonians, crocodiles, snakes, and the like; a cephalopod, such as squid and the like; marine invertebrate animals, such as starfish, tunicate, geoduck, and the like; and combinations of these. For example, raw material 65 can comprise sciatic nerve tissue, such as sciatic nerve tissue harvested from a tissue source 60 comprising a pig (e.g. a male pig), such as a pig with a weight between 1 lbs and 400 lbs, such as a weight between 50 lbs and 300 lbs, such as a weight of approximately 250 lbs.

Raw material 65 can comprise tissue harvested from one, two, or more similar and/or dissimilar tissue sources 60. Tissue harvested from multiple (e.g. two or more) tissue sources 60 can be pooled to provide a larger quantity of homogeneous raw material 65. Raw material 65 can comprise tissue harvested from a uniform sex, such as tissue harvested from all male tissue sources 60 or all female tissue sources 60. Tissue harvested from a uniform sex can increase tissue consistency. Raw material 65 can comprise tissue harvested from both male and female tissue sources 60. Raw material 65 can comprise tissue harvested from an adult and/or juvenile tissue source 60, such as tissue harvested from all adult tissue sources, all juvenile tissue sources, or both adult and juvenile tissue sources. Raw material 65 can comprise tissue harvested from a genetically uniform tissue source 60 (e.g. tissue from a single genetic strain of animals). Alternatively or additionally, raw material 65 can comprise tissue harvested from a genetically modified tissue source 60. For example, raw material 65 can comprise tissue harvested from an α1,3-galactosyltransferase knockout pig.

Raw material 65 can comprise tissue harvested from one, two, or more tissue sources 60 that provide an increased potency and/or altered mechanical, physical, and/or chemical characteristics of raw material 65. Raw material 65 can comprise an increased potency and/or altered characteristic of an element selected from the group consisting of: nerve tissue type; adult tissue; juvenile tissue; tissue from genetically-modified animals or tissue transfected with genetic material; tissue from mechanically conditioned animals or mechanically conditioned tissue; tissue from chemically conditioned animals or chemically conditioned tissue; tissue from pharmacologically conditioned animals or pharmacologically conditioned tissue; tissue from physically conditioned animals or physically conditioned tissue; tissue from psychologically conditioned animals; and combinations of these.

Raw material 65 can comprise tissue harvested from one, two, or more tissue sources 60 that is subsequently subjected to a conditioning and/or other tissue regimen. The tissue regimen can be configured to modify the mechanical, physical, and/or chemical characteristics of raw material 65. In some embodiments, raw material 65 is cross-linked to alter its degradation rate and/or orient its microstructure.

Raw material 65 can comprise tissue harvested from one, two, or more tissue sources 60 comprising an animal that adhered to a pre-determined diet, exercise, chemical, pharmacological, physical, psychological stimulation, and/or other regimen. The pre-determined regimen can be configured to modify the anatomical and/or physiological characteristics of tissue source 60. In some embodiments, the animal adhered to a physical stimuli regimen, such as exercise, electrical stimulation, mechanical conditioning (e.g. stretch, compression), physical conditioning (e.g. thermal, light exposure), and radiation. In some embodiments, the applicable animal adhered to a psychological conditioning regimen, such as different levels of daily stress or lack thereof, amount of space per animal, level of socialization, different sleep/light cycles, and level of induced sexual or reproductive activity.

Device 100 can be constructed and arranged to be used in a therapeutic, diagnostic, and/or other clinical applications in one or more medical fields, such as dentistry (e.g. endodontics, orthodontics), dermatology, ophthalmology, obstetrics, gynecology, cardiology and cardiac electrophysiology, gastroenterology, orthopedic, oncology, neurology, neurosurgery, endocrinology, lymphology, surgery (e.g. plastic aesthetic, plastic reconstruction, otolaryngology, and oral and maxillofacial surgery), and the like. In some embodiments, device 100 is constructed and arranged as a bulking agent for administration during a surgical procedure (e.g. a plastic reconstruction, aesthetic procedure). In some embodiments, device 100 is constructed and arranged as an embolic, clotting, and/or obstructive agent for administration during a surgical, minimally invasive, and/or percutaneous procedure.

Device 100 can be constructed and arranged for treatment of male and female sexual dysfunction or for sexual enhancement applications, such as male erectile dysfunction, retarded or premature ejaculation, lack of sensation, penile enlargement, and female genital cosmetic, reconstructive, and enhancement surgery.

Device 100 can be constructed and arranged for a therapeutic and/or clinical application in a veterinary field, such as large animal surgery, small animal surgery, farm animal surgery, competitive animal conditioning, farm animal conditioning, and military and training animal conditioning.

Device 100 can be constructed and arranged for a cosmetic application, such as a tissue bulking agent, restoration of facial animation or improvement of facial expressivity. Device 100 can comprise a topical formulation configured for the treatment of skin conditions.

Device 100 can be constructed and arranged for a food supplement application, such as to improve skin health, improve hair health, improve nail health, relieve joint pain and increase motility, prevent bone loss, improve heart health, increase muscle mass, and increase physical performance.

Device 100, comprising ECM 120, can comprise a configuration selected from the group consisting of: a fluid and/or semi-fluid (either or both, "fluid" herein), such as a hydrogel, cream, ointment, or the like; a spongy material; a compressed material, such as a film; a solid material, such as a wrap, conduit, graft, suture, or the like; an aerosolized material, such as a spray; a flowable particulate, such as a micronized and flowable particulate; a powder; a fibrous material; and combinations of these. In some embodiments, device 100 is configured to deliver one, two, or more therapeutic agents (e.g. agent 70 described herein) to the patient (e.g. pharmaceutical drugs, stem cell therapies, etc.), such as when device 100 further comprises a plurality of microspheres comprising a therapeutic agent.

Device 100 can comprise a mechanical strength and/or degradation rate/durability that is modified via at least one of chemical cross-linking or physical cross-linking.

Device 100 can comprise a degradation rate in vivo of between 24 hours and 6 months, such as a degradation rate in vivo of between 2 weeks and 2 months, such as a degradation rate in vivo of approximately 4 weeks.

In some embodiments, device 100 comprises a fluid comprising a dynamic viscosity between 20 cP and 200 cP. Device 100 can comprise a lower viscosity for injectable applications, such as a viscosity of between 1 cP and 100 cP. Device 100 can comprise a greater viscosity for topical applications, such as a viscosity of between 1000 cP and 45,000 cP.

In some embodiments, device 100 comprises a fluid having an osmolarity of between 100 and 365 mOsmol/L, such as an osmolarity of between 200 and 280 mOsmol/L. The osmolarity can be adjusted to modify (e.g. increase, decrease) the mechanical properties, gelation kinetics, working time, and/or responsiveness to temperature of device 100.

In some embodiments, device 100 comprises a fluid that transitions to a gel. Device 100 can be configured to transition from a fluid to a gel via self-assembly, fibrillogenesis, chemical cross-linking, physical cross-linking, and combinations of these. Device 100 can transition to a gel prior to its deployment at the deposit site, such that device 100 transitions to a gel ex vivo. In some embodiments, device 100 is configured to transition to a gel at a time between 0.5 minutes and 2 hours prior to deployment of device 100 at the deposit site. Device 100 can transition to a gel during and/or after its deployment at the deposit site, such as transition to a gel in situ. In some embodiments, device 100 is configured to transition to a gel at a time between 0.5 minutes and 10 minutes within the time of deployment of device 100 at the deposit site. Device 100 can comprise a volume that decreases as it transitions from a fluid to a gel. For example, device 100 can contract over a period of time as it transitions from a fluid to a gel. In some embodiments, device 100 further comprises a plurality of expansion elements configured to compensate for the decrease in volume. The expansion elements can be configured to maintain a relatively constant volume of device 100, such that the expansion elements correspondingly expand as device 100 contracts.

In some embodiments, device 100 comprises a semi-fluid and/or solid that is molded, or otherwise manipulated, into a geometric shape prior to, during, and/or after deployment at the deposit site.

In some embodiments, device 100 is constructed and arranged as a coating configured to at least partially cover one, two, or more surfaces of the deposit site. Device 100 can be configured to coat a surface of the deposit site via an atomization process, such as an atomization process performed using tool 80. Device 100 can be configured to coat a surface of the deposit site via a brushing process, such as a brushing process performed using tool 80. Device 100 can be configured to coat a surface of the deposit site via a dipping process, such as a dipping process performed using tool 80.

In some embodiments, device 100 is constructed and arranged as a "nerve cap" configured to be at least partially placed over one, two, or more nerve endings. In some embodiments, the nerve cap comprises a cylindrical device open at one end and closed or open at the opposite end, and into which a nerve end can be inserted and secured. For example, device 100 can be placed over a nerve ending following an amputation. As another example, device 100 can be configured to embed a severed nerve directly into a muscle body to promote reinnervation of the muscle.

In some embodiments, device 100 is constructed and arranged as a nerve connector configured to align and/or connect two or more nerves (e.g. end-to-end; end-to-side, side-to-side nerve connections, etc.) at a treatment site. For example, device 100 can connect two or more nerve stumps and promote nerve regrowth between the nerve stumps.

Figure 2:
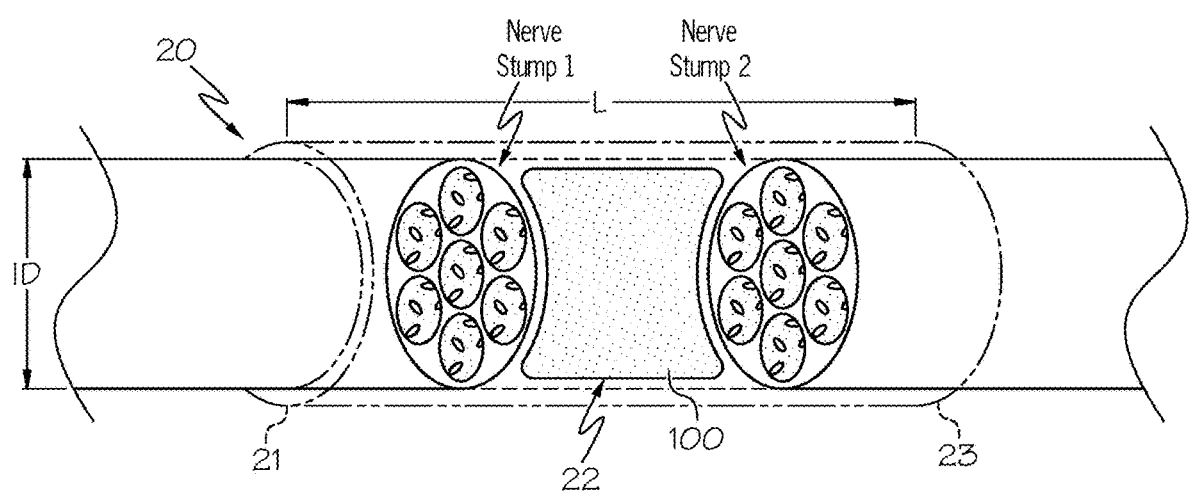
FIG. 2 illustrates a perspective view of a medical device comprising a conduit, consistent with the present inventive concepts.

In some embodiments, device 100 is constructed and arranged as a nerve conduit, graft (e.g. allograft, autograft, xenograft), or a combination of a graft and a conduit (e.g. graft-conduit) such as described herein in reference to FIGS. 2, 4A and B, 22, and 24, and can be configured to at least partially replace and/or supplement one, two, or more nerves at a treatment site. Device 100 can comprise one or more internal longitudinal tunnels, these can be intertwining tunnels constructed and arranged to mimic the natural plexus structure of a peripheral nerve.

In some embodiments, device 100 is constructed and arranged to fill the lumen of a conduit, graft, or graft-conduit combination (e.g. implant 20 described herein). Such conduit, graft, or graft-conduit combination can comprise polymeric materials, such as polycaprolactone, PLLA, PGA, silicone, polyurethane, PET, or PTFE. In some embodiments, such conduit or graft can comprise naturally derived materials such as collagen, elastin, GAG, keratin, chitosan, and/or combinations of synthetic and naturally derived materials. In some embodiments, device 100 is comprised of a segment of decellularized nerve, with or without modification to create one or more internal longitudinally oriented tunnels.

In some embodiments, device 100 is constructed and arranged as a suture material, such as a nerve suture material. ECM 120 can be extruded or drawn using textile manufacturing techniques to fabricate a biodegradable mono- or multi-stranded filament configured to connect or repair nerve tissues. Device 100 can be constructed and arranged as a suture material comprising a straight strength and a knot strength, such that the knot strength is between 70% and 80% of the straight strength. Device 100 can be constructed and arranged as a suture comprising a size between 6-0 and 10-0. Device 100 can be constructed and arranged as a suture comprising a tensile strength greater than 0.5N, such as greater than 1N, such as greater than 2N.

In some embodiments, device 100 is constructed and arranged as an electrode coating. Device 100 can be configured to reduce inflammation, scarring, and/or facilitate nerve growth and/or integration at the tissue-electrode interface of an implantable device. Growth and/or integration of nerve tissue at the tissue-electrode interface can reduce impedance and improve conductivity, such as to improve signal to noise reductions. Reduction of inflammation and/or scarring can prolong the useful life of the electrode, lead, or sensor. In some embodiments, device 100 is configured to enhance the performance of a nerve stimulation device.

In some embodiments, device 100 is constructed and arranged as a scaffold configured to provide structural support for cell attachment, cell migration, cell alignment, cell proliferation, cell differentiation, cell phenotype, cell selection, cell development, gene expression, protein expression, protein secretion, tissue alignment, and/or tissue development at a treatment site.

Device 100 can be incorporated into (e.g. embedded in, combined with, used in conjunction with, and the like) an existing medical device and/or material. In some embodiments, device 100 is incorporated into a patch and/or film. In some embodiments, device 100 is incorporated into suture material. In some embodiments, device 100 is incorporated into an adhesive, such as fibrin glue.

Device 100 (e.g. ECM 120) can be incorporated into a nerve conduit, such as implant 20 as described herein in reference to FIG. 2. In some embodiments, device 100 is incorporated into the nerve conduit prior to implantation into a patient, such as during a manufacturing process of the nerve conduit and/or ECM 120. For example, ECM 120 comprising neutralizing element 140 can be injected into the lumen of the nerve conduit. Alternatively or additionally, the nerve conduit can be submerged in a bath of ECM 120 comprising neutralizing element 140. Alternatively or additionally, the nerve conduit can be spray coated with ECM 120 comprising neutralizing element 140. Subsequently, the nerve conduit comprising ECM 120 and neutralizing element 140 can be dehydrated via vacuum drying or lyophilization. Prior to implantation, the dehydrated nerve conduit can be rehydrated upon immersion into a saline solution. As another example, ECM 120 comprising a lyophilized cake can be press-fit into the nerve conduit, such as when ECM 120 comprises a micronized lyophilized cake. As another example, device 100 can be injected via a needle into the lumen of the nerve conduit and allowed to gel at a temperature of approximately 37° C. prior to implantation into the patient. As another example, the nerve conduit can be impregnated with device 100 via a vacuum source. The nerve conduit can be held within a channel and the vacuum source can be applied at one end of the conduit while device 100 is injected at an opposite end. Device 100 can be configured to permeate (e.g. transmural permeation) through the nerve conduit. As another example, the nerve conduit can be impregnated with device 100 via submersion into a bath comprising device 100. As another example, the nerve conduit can be impregnated with device 100 via a spray coating comprising device 100. As another example, the nerve conduit can be inserted into a container comprising device 100 and centrifuged or otherwise agitated within the container. As another example, the nerve conduit can be impregnated with device 100 via immersion into a fluid flow comprising device 100. As another example, the nerve conduit can be printed with device 100.

In some embodiments, device 100 is incorporated into a conduit or into a nerve via percutaneous or minimally invasive methods. For example, device 100 can be injected via a needle under ultrasound or fluoroscopy guidance into the implanted nerve conduit, such as injected into the lumen of the nerve or conduit via an end and/or through a side wall of the nerve or conduit.

Device 100 can be delivered, injected, implanted, and/or otherwise deployed ("deployed" herein) proximate a treatment site. Device 100 can be deployed into, onto, and/or at the deposit site, such as a focal area of a treatment site.

Device 100 can be deployed to extend to, or otherwise cover, one, two, or more locations beyond the deposit site (e.g. into locations of the treatment site or other locations). Device 100 can be deployed to extend longitudinally beyond the deposit site. In some embodiments, device 100 extends proximally from the deposit site, such as between 2 mm and 20 mm proximally from the deposit site, such as between 2 mm and 5 mm, such as between 5 mm and 10 mm, such as between 10 mm and 20 mm. In some embodiments, device 100 extends distally from the deposit site, such as between 2 mm and 20 mm distally from the deposit site, such as between 2 mm and 5 mm, such as between 5 mm and 10 mm, such as between 10 mm and 20 mm.

Device 100 can be deployed at one, two, or more deposit sites positioned about the circumference of a nerve within and/or externally to the nerve. Two or more deposit sites can comprise a uniform spacing about the circumference of the nerve. The two or more deposit sites can comprise a non-uniform spacing about the circumference of the nerve. For example, device 100 can be deployed at a first deposit site representing 0°, at a second deposit site that is 120° relative to the first deposit site, and at a third deposit site that is 240° relative to the first deposit site (and 120° relative to the second deposit site).

Device 100 can be deployed at one, two, or more deposit sites about the circumference of a nerve and can be further deployed at one, two, or more locations beyond the deposit sites, as described herein. In some embodiments, deployment of device 100 at the deposit sites and locations beyond the deposit sites comprise a matrix of device 100 along the external surface of the nerve.

In some embodiments, the deposit site comprises a location (e.g. one, two, three, or more locations) within the central nervous system, such as a site located within and/or surrounding the brain and/or spinal cord. In some embodiments, the deposit site comprises a location within the peripheral nervous system, such as a site located outside the brain and spinal cord, including any location along and/or around the peripheral nervous system spanning from the dorsal and/or ventral root ganglia to motor, sensory, or autonomic endings (e.g. end-muscle plate, Pacinian corpuscle, Ruffini endings). In some embodiments, the deposit site comprises a location within, and/or around, and/or proximate an uninjured nerve. In some embodiments, the deposit site comprises a location within, and/or around, and/or proximate a diseased nerve. In some embodiments, the deposit site comprises a location within, and/or around, and/or proximate a nerve injury, such as an intra-nerve and/or peri-nerve injury location. In some embodiments, the deposit site comprises a location within, and/or around, and/or proximate a partial or full nerve transection, such as a transected and repaired nerve (e.g. epineural and/or fascicular repair, such as neurorrhaphy). For example, device 100 can be deployed to provide an interface between two or more nerves, nerve stumps, or nerve epineural windows. The two or more nerve stumps can be coapted together, such as via a suture or fibrin glue configured to eliminate or otherwise reduce a gap length between the nerve stumps. Alternatively, the two or more nerve stumps are not coapted together and a calculated gap length is maintained between the nerve stumps. The calculated gap length can be configured to promote nerve cone sprouting and alignment from a proximal nerve stump having a greater degree of freedom to properly align toward a distal nerve stump. In some embodiments, the deposit site comprises a location within, around, and/or proximate a nerve injury repaired with a nerve transfer technique, such as an end-to-end transfer, side-to-side transfer, end-to-side transfer, or supercharged end-to-side transfer. In some embodiments, the deposit site comprises a location within, around, and/or proximate a nerve crush injury, such as an acutely crushed nerve. In some embodiments, the deposit site comprises a location within, around, and/or proximate a nerve stretch injury, such as an acutely stretched nerve. In some embodiments, the deposit site comprises a location within, around, and/or proximate a compression nerve injury, such as chronic compression with or without prior surgical release. In some embodiments, the deposit site comprises a location within, around, and/or proximate a nerve gap injury repaired with a nerve conduit or graft, such as an allograft, autograft, conduit, or guide. In some embodiments, the deposit site comprises a location within, around, and/or proximate a targeted muscle reinnervation. For example, device 100 can be deployed to promote total muscle reinnervation. In some embodiments, the deposit site comprises a location within, around, and/or proximate a neurotization. For example, device 100 can be deployed to promote direct muscle neurotization, such that device 100 can be deployed within, around, and/or proximate a nerve apposed into and/or onto muscle, such as to promote nerve sprouting into the muscle. For example, device 100 can be deployed to promote combined muscle neurotization, such that device 100 can be deployed within, around, and/or proximate a nerve apposed into and/or onto muscle via a nerve conduit, such as to promote nerve sprouting into the muscle. In some embodiments, the deposit site comprises a location within, around, and/or proximate a nerve end surgically connected to muscle and configured to reactivate the muscle, such as proximate an end-to-end nerve transfer or Oberlin procedure. In some embodiments, the deposit site comprises a location within, around, and/or proximate a nerve attached to isolated patches of muscles, such as directly via direct neurotization or via existing innervation (e.g. regenerative peripheral nerve interface). In some embodiments, the deposit site comprises a location within, around, and/or proximate a nerve end surgically connected to muscle and configured to create an electrical activation map on the muscle surface, such as proximate a total muscle reinnervation. For example, the electrical activation map can be detected by skin electrodes configured to control electronic prostheses. In some embodiments, the deposit site comprises a location within, around, and/or proximate a nerve biopsy. In some embodiments, the deposit site comprises a location within, around, and/or proximate an iatrogenic (e.g. medically, surgically induced) nerve injury. In some embodiments, the deposit site comprises a location within, around, and/or proximate a brachial plexus injury. For example, device 100 can be deployed during an Oberlin or Leechavengvongs procedure. In some embodiments, the deposit site comprises a location within, around, and/or proximate a peripheral nerve injury in which there is no nerve gap. In some embodiments, the deposit site comprises a location within and/or proximate a peripheral nerve injury in which a gap closure is achieved with or without flexion of an extremity. In some embodiments, the deposit site comprises a location within, around, and/or proximate a tissue burn, such as a superficial burn, a partial thickness burn, and/or a full thickness burn. In some embodiments, the deposit site comprises a location within, around, and/or proximate a truncated nerve following an amputation. For example, device 100 can be deployed at the site of one or more nerves affected by an amputation. In some embodiments, the deposit site comprises a location that contributes to a symptom attributed to a migraine. For example, device 100 can be deployed to treat, or otherwise alleviate, migraine symptoms. In some embodiments, the deposit site comprises a location within, around, and/or proximate muscle tissue. In some embodiments, the deposit site comprises a location within, around, and/or proximate denervated muscle tissue. For example, device 100 can be deployed to promote neuromuscular junction formation. In some embodiments, the deposit site comprises a location within, around, and/or proximate a nerve end surgically connected to a sensory receptor, such that device 100 can be deployed to promote nerve sprouting into the receptor and/or reestablish sensation. In some embodiments, the deposit site comprises distributed locations via topical applications onto a surgically created cavity, onto a mucosal surface or cavity, into an organ, and/or onto the skin or injured skin surface.

In some embodiments, device 100 is deployed into a deposit site comprising muscle tissue. In some embodiments, device 100 is deployed into a deposit site comprising tendon, ligament, or cartilage tissue. In some embodiments, device 100 is deployed into a deposit site comprising organ tissue. In some embodiments, device 100 is deployed into a deposit site comprising vascular wall tissue. In some embodiments, device 100 is deployed into a deposit site comprising lymphatic tissue. In some embodiments, device 100 is deployed into a deposit site comprising neural tissue. In some embodiments, device 100 is deployed into and/or through skin tissue (e.g. epidermis, dermis, subcutaneous) proximate the deposit site. In some embodiments, device 100 is deployed topically onto the skin, organ, and/or surgical cavity. In some embodiments, device 100 is deployed into or onto the deposit site percutaneously and/or minimally invasively.

In some embodiments, device 100 is deployed into a deposit site comprising oral tissue (e.g. oral mucosa, teeth, tooth pulp, cranial nerve, tongue). In some embodiments, device 100 is deployed into the tooth root following a root canal or pulpectomy procedure. In some embodiments, device 100 is deployed into and/or around the cranial nerves. In some embodiments, device 100 is deployed into the oral mucosa. In some embodiments, device 100 is deployed into the tongue or lips.

In some embodiments, device 100 is deployed into a deposit site comprising heart nervous system including both the heart conduction system (e.g. sino-atrial node, atrio-ventricular node, Purkinje fibers, etc.) and the heart nervous system tissue from the lower cervical to the upper thoracic ganglia (e.g. cardiac plexus, parasympathetic and sympathetic nerve fibers, vagal cardiac nerve, vagus nerve, etc.).

In some embodiments, the treatment site comprises at least a portion of a nerve and device 100 is deployed at a deposit site comprising at least a portion of a neural location selected from the group consisting of: intra-mesoneurium; peri-mesoneurium; intra-epineurium; peri-epineurium; sub-epineurium; intra-fascicular, sub-endoneurium; and combinations of these. For illustrative purposes, and as described herein, FIGS. 13A-J comprise cross-sectional and/or side views of one, two, or more nerves comprising device 100.

In some embodiments, device 100 is deployed at a deposit site distal to and/or proximal to the treatment site, such as at an ectopic site. Device 100 can be deployed into muscle tissue and/or organ tissue distal to the treatment site, such as to promote nerve growth (e.g. neurotization) towards the treatment site, such as to restore sensation and/or motor control. Device 100 can be deployed into a deposit site comprising muscle tissue and/or skin tissue (e.g. epidermis, dermis, subcutaneous) distal to the treatment site, such as to recruit, or otherwise promote the growth of, muscle fibers.

Device 100 can be deployed contemporaneously (e.g. concurrently) with one, two, or more additional treatments provided to the patient (e.g. one or more treatments deployed at the deposit site, the treatment site, and/or another patient location). In some embodiments, device 100 is deployed contemporaneously with an electrical stimulation. In some embodiments, device 100 is deployed contemporaneously with a pharmacological treatment. In some embodiments, device 100 is deployed contemporaneously with a cellular treatment. In some embodiments, device 100 is deployed contemporaneously with a structural element (e.g. sutures, conduit, wrap, glue). In some embodiments, device 100 is deployed contemporaneously with physical, occupational therapy and/or electrical, magnetic, and laser stimulation.

Device 100 can comprise one or more functional elements, functional element 199 shown. Functional element 199 can comprise a sensor and/or a transducer. In some embodiments, functional element 199 comprises a biofeedback element. For example, device 100 can further comprise a biofeedback mechanism (e.g. functional element 199) configured to provide an indication of a biological, mechanical, chemical, or electric signal at the deposit site.

In some embodiments, device 100 further comprises one or more pharmacological or other agents, agent 70 shown. Agent 70 can be included in (e.g. integrated into) device 100, or it can be provided separately. Agent 70 can comprise an antimicrobial agent. Agent 70 can comprise a color additive. Agent 70 can comprise an adhesive. In some embodiments, combination of device 100 with an adhesive is configured to reinforce a suture site and/or as a primary means of structural reconstruction of a nerve. Agent 70 can comprise an immunosuppressing agent configured to promote, or otherwise support, nerve regeneration, such as FK506. Agent 70 can comprise a chemical agent configured to modify, or otherwise effect, an immune response at the deposit site, such as when agent 70 comprises an immunomodulator (e.g. immunosuppressant). Agent 70 can comprise an antimicrobial agent configured to kill, or otherwise stop or slow down, the growth of microorganisms at the deposit site, such as when agent 70 comprises one, two, or more agents selected from the group consisting: disinfectant; antiseptic; antibiotic; and combinations of these. Agent 70 can comprise a visual additive, such as a visual additive configured to provide visibility to device 100, such as a dye configured to be visualized via an imaging device 30. Agent 70 can comprise a lubricating substance configured to minimize friction at the deposit site. Agent 70 can comprise a conductive agent configured to increase electrical conductivity at the deposit site. Agent 70 can comprise one or more anti-adhesive agents configured to prevent an adhesion at the deposit site, such as to prevent fibrotic adhesions. Agent 70 can comprise an anesthetic and/or pain reliever agent configured to induce an insensitivity at the deposit site (e.g. insensitivity to pain and/or sensation). Agent 70 can comprise a hemostatic agent configured to promote hemostasis at the deposit site. Agent 70 can comprise an antidote configured to counteract a poison and/or toxin at the deposit site, such as an antidote configured to counteract a nerve agent. Agent 70 can comprise an anti-inflammatory agent configured to reduce inflammation at the deposit site. Agent 70 can comprise a chemoattractant configured to attract motile cells to the deposit site, such as a motile cell selected from the group consisting of: Schwann cells; macrophages; endothelial cells; progenitor cells; and combinations of these. Agent 70 can comprise an agent configured to promote the production of angiogenic factors at the deposit site, such as an angiogenic factor selected from the group consisting of: angiogenin; growth factors, such as fibroblast growth factors, transforming growth factors; lipids; and combinations of these. Agent 70 can comprise an agent configured to promote cell migration, development, and/or maturation at the deposit site, such as a nerve growth factor.

In some embodiments, device 100 is configured to exhibit cell adhesion properties configured to interact and/or attach to neighboring cells at the deposit site, such as one, two, or more cell adhesion properties associated with cell-adhesion molecules selected from the group consisting of: integrins; immunoglobulins; cadherins; selectins; and combinations of these. In some embodiments, device 100 is configured to exhibit cell signaling properties configured to communicate and/or coordinate cell actions at the deposit site, such as one, two, or more properties associated with cell signals selected from the group consisting of: intracrine signals; autocrine signals; juxtracrine signals; paracrine signals; endocrine signals; and combinations of these. In some embodiments, device 100 is configured to exhibit pharmacological and/or biological properties configured to support the local microenvironment at the deposit site, such as to promote immunomodulatory action, revascularization, cell chemotaxis, cell development, and/or nerve tissue deposition.

Device 100 can be configured to respond to electrical, mechanical, physical, and/or chemical factors, such as factors internal and/or external to device 100. For example, device 100 can be configured to respond to temperature, sound waves, electromagnetic waves, and/or light (e.g. coherent light, such as laser). In some embodiments, device 100 is configured to undergo a physical change upon the application of an ultraviolet light internally and/or externally to ECM 120, such as when device 100 transitions from a fluid to a semi-fluid and/or solid. In some embodiments, device 100 is configured to release an agent (e.g. agent 70, such as a chemical, pharmaceutical, and/or other agent) upon the application of an external vibration to device 100.

System 10 Components

System 10 can further comprise one or more implants, implant 20 shown. Implant 20 can comprise a conduit as described herein in reference to FIG. 2.

System 10 can further comprise one or more imaging devices, device 30 shown, which can be configured to visualize an object (e.g. device 100). Device 30 can comprise an imaging device selected from the group consisting of: microscope, such as a surgical microscope; loupes; magnifying lens; device that provides virtual and/or augmented reality visualization; device that provides stereo visualization; device that provides infrared near-infrared visualization; device that provides thermal imaging; medical imaging device, such as an X-ray, a fluoroscope, an MRI, a CT scanner, OCT, an ultrasound, an endoscope; device that images using UV light; device that images using polarized light; device that images using fluorescent light; and combinations of these.

System 10 can further comprise one or more tools, tool 80 shown, which can be configured to coat a surface (e.g. a surface of a deposit site), such as an atomization tool, a brush or brushing tool, and/or a dipping tool, as described herein. Tool 80 can comprise a tattoo machine configured to deliver ECM 120 at a defined depth of a surface. Tool 80 can comprise a jet injector configured to deliver ECM 120 via high pressure at a defined depth of a surface. Tool 80 can comprise a bobbin including a coiled strand or ribbon embedded with ECM 120 configured to wind and/or canvas around a surface. Tool 80 can comprise an adhesive or adhesive strip configured to affix ECM 120 to a surface.

System 10 can further comprise one, two, or more sub-containers, container 203 shown which can be configured to store one, two, or more other components of system 10. Container 203 can comprise a configuration selected from the group consisting of: a paper-based box; a paper-based tray; a paper-based pouch; a tray comprising a synthetic material; a pouch comprising a synthetic material; a foil pouch further comprising a synthetic material; seals comprising synthetic or foil material; outer coverings comprising synthetic materials or plastics; and combinations of these. Container 203 can comprise one, two, or more materials configured to withstand conditions associated with sterilization protocols (e.g. Tyvek® or flashspun high-density polyethylene fibers, or foil), such that container 203 can be sterilized. Container 203 can further include a lid, or other moveable cover. Container 203 can be configured to provide a vapor barrier to the contents contained therein.

System 10 can further comprise one, two, or more support containers, container 205 shown, which can be configured to store one, two, or more other components of system 10. Container 205 can comprise a configuration selected from the group consisting of: a paper-based box; a paper-based tray; a paper-based pouch; a tray comprising a synthetic material; a pouch comprising a synthetic material; a foil pouch further comprising a synthetic material; seals comprising synthetic or foil material; outer coverings comprising synthetic materials or plastics; and combinations of these. Container 205 can comprise one, two, or more materials configured to withstand conditions associated with sterilization protocols (e.g. Tyvek® or flashspun high-density polyethylene fibers, or foil), such that container 205 can be sterilized. Container 205 can further include a lid, or other moveable cover. Container 205 can be configured to provide a vapor barrier to the contents contained therein.

System 10 can further comprise one, two, or more presentation containers, container 207 shown which can be configured to store one, two, or more other components of system 10. Container 207 can comprise a configuration selected from the group consisting of: a paper-based box; a paper-based tray; a paper-based pouch; a tray comprising a synthetic material; a pouch comprising a synthetic material; a foil pouch further comprising a synthetic material; seals comprising synthetic or foil material; outer coverings comprising synthetic materials or plastics; and combinations of these. Container 207 can comprise one, two, or more materials configured to withstand conditions associated with sterilization protocols (e.g. Tyvek® or flashspun high-density polyethylene fibers, or foil), such that container 207 can be sterilized. Container 207 can further include a lid, or other moveable cover. Container 207 can be configured to provide a vapor barrier to the contains contained therein.

System 10 can further comprise one or more vials, vial 210 shown, which can be configured to store one, two, or more fluids, powders, cakes, and/or capsules. Vial 210 can be configured to store a volume between 0.5 mL and 50 mL, such as a volume between 2 mL and 5 mL. Vial 210 can comprise a material selected from the group consisting of: glass, such as Type 1 borosilicate; plastic, such as polypropylene, polyethylene; metal, such as steel, aluminum; and combinations of these. Vial 210 can further include a sterility barrier selected from the group consisting of: a rubber stopper; a flip-off cap, such as a plastic cap; a tear-off seal, such as an aluminum seal; a crimp seal, such as a plastic seal; and combinations of these.

System 10 can further comprise one or more vial stoppers, stopper 211 shown, which can be configured to be inserted into an opening of vial 210. Stopper 211 can comprise a configuration selected from the group consisting of: multiple leg, such as two-leg, three-leg, and the like; round bottom; igloo; and straight plug. Stopper 211 can comprise a surface area configured to prevent, or otherwise reduce, the loss of a fluid and/or powder within vial 210. Stopper 211 can comprise a surface area configured to provide a moisture barrier to the fluid and/or powder within vial 210. Stopper 211 can be constructed and arranged as a lyophilization stopper.

System 10 can further comprise one or more fluid delivery devices, syringe 220 shown, which can be configured to draw in, or otherwise receive, and/or expel a fluid. Syringe 220 can comprise a barrel 202 configured to sliding receive a plunger 212. Barrel 202 can comprise a distal end comprising a luer lock 204 and a proximal end comprising a barrel flange 206. Plunger 212 can comprise a distal end comprising a seal 214 and a proximal end comprising a plunger flange 216. In some embodiments, plunger 212 comprises a removable seal 214, such as that seal 214 can be detached from plunger 212 and positioned within barrel 202. Syringe 220 can comprise a material selected from the group consisting of: plastic, such as cyclic olefin copolymer; glass; and combinations of these. Syringe 220 can include a pre-attached (e.g. pre-inserted) plunger 212. Alternatively, syringe 220 may not include a pre-attached plunger 212, such that a separate plunger 212 is provided for subsequent attachment to syringe 220. In some embodiments, syringe 220 comprises a tuberculin syringe that can receive up to 1 mL of fluid.

Syringe 220 can be configured to maintain (e.g. surround) and deploy device 100 to the deposit site, such as device 100 comprising a fluid. An operator, as described herein in reference to FIGS. 10-12, can manipulate syringe 220 to control at least one of the following: angle of deployment; depth of deployment; volume of deployment; flow rate of deployment; positioning of deployment; pattern of deployment (e.g. helix, matrix); or combinations of these. Syringe 220 can be internally coated with a silicone of PTFE lubricant to facilitate the ease of deployment.

System 10 can further comprise one or more fluid delivery elements, needle 240 shown, which can be configured to connect to syringe 220 (e.g. luer lock 204) to deliver a fluid. Needle 240 can comprise a gauge of at least 30G, such as a gauge of at least 27G, or at least 22G. Needle 240 can comprise a straight and/or curved shape. Needle 240 can comprise a length of between 4 mm and 15 mm. Needle 240 can comprise a distal tip with a geometry selected from the group consisting of: point bevel; flat point; blunt; and olive tipped. Needle 240 can comprise a needle cannula. Needle 240 can be connected to syringe 220 via an extension line, such as a catheter.

System 10 can further comprise one or more connectors, connector 260 shown, which can be configured to provide a fluid-tight connection between two or more components of system 10. Connector 260 can comprise a male luer, a female luer, a male-to-female luer, a male-to-male luer, or a female-to-female luer. Connector 260 can further include a stopcock valve configured to facilitate degassing of a fluid that passes through connector 260, such as a one-way, two-way, or three-way stopcock valve. Connector 260 can further include a filter configured to prevent, or otherwise impede, particles or solution from passing through connector 260. In some embodiments, the filter comprises a polypropylene or metal mesh with a pore size of between 0.2 µm and 500 µm.

System 10 can further comprise one or more adaptors, adaptor 280 shown, which can be configured to provide to a fluid-tight connection between vial 210 and another component of system 10 (e.g. syringe 220). Adaptor 280 can comprise a vented or non-vented vial adaptor configured to attach to the top of vial 210. Adaptor 280 can further include a filter. In some embodiments, the filter comprises a pore size of approximately 0.2 µm. For example, adaptor 280 can comprise a vented vial adaptor including a filter configured to prevent, or otherwise reduce, depressurization of vial 210 (e.g. allow fluid ingress as contents within vial 210 are withdrawn).

System 10 can further comprise one or more homogenizing elements, homogenizer 290 shown, which can be configured to stir, mix, and/or otherwise agitate two or more materials (e.g. fluids) into a relatively homogenous mixture. Homogenizer 290 can be constructed and arranged as a component of system 10, such as a component of connector 260. For illustrative purposes, and as described herein, FIGS. 14A-G comprise a connector 260 including different embodiments of homogenizer 290.

System 10 can further comprise one or more support assemblies, assembly 300 shown, which can be configured to receive and/or secure an object (e.g. device 100, device 400, and/or ECM 120). Support assembly 300 can be constructed and arranged as described herein in reference to FIGS. 4A,B and 22.

System 10 can further comprise one or more environmental chambers, chamber 601 shown. Chamber 601 can comprise a temperature-controlled environmental chamber configured to chill and/or freeze an object (e.g. raw material 65) through non-cyclic and/or cyclic refrigeration. In some embodiments, chamber 601 consists of frozen ice or synthetic ice packs within an insulated container. In some embodiments, chamber 601 consists of a refrigerator or deli case with or without an incorporated shaker system.

System 10 can further comprise one or more vessels, vessel 602 shown, which can be configured to store an object (e.g. raw material 65). Vessel 602 can comprise a vented container configured to comprise one or more openings to allow for the passage of air, gas, and/or liquid through vessel 602. In some embodiments, vessel 602 is configured to store a tissue sample during tissue processing, embedding, and/or sectioning.

System 10 can further comprise one or more mixing devices, device 603 shown, which can be configured to stir, mix, and/or otherwise agitate a fluid disposed within a component of mixing device 603. Mixing device 603 can be configured to agitate a fluid at a speed between approximately 50 rpm and 2,000 rpm. In some embodiments, mixing device 603 includes an impeller configured to rotate, thereby agitating a fluid disposed within mixing device 603. In some embodiments, device 603 consists of an ultrasonic mixing device, such as a device configured to provide mechanical shock waves.

System 10 can further comprise one or more heating devices 604, device 604 shown. Heating device 604 can be configured to warm and/or maintain the temperature of an object (e.g. raw material 65). Heating device 604 can comprise a hotplate comprising electric heating elements. In some embodiments, heating device 604 comprises a stirring hotplate comprising a rotating magnetic field configured to rotate a corresponding magnetic bar that is positioned in fluid proximate a surface of heating device 604. In some embodiments, heating device 604 can comprise an incubator with or without an incorporated shaking/mixing system.

System 10 can further comprise one or more laboratory instruments, instrument 605 shown, such as an instrument selected from the group consisting of: pipette, such as a serological pipette, a positive displacement pipette; forceps, such as serrated tip forceps, single tooth forceps; scalpel, such as a stainless-steel scalpel; scraper, such as a stainless-steel scraper; blade, such as a stainless-steel blade; a cutting surface, such as a polymeric cutting board; band, such as silicone band; funnel; temperature probe; a measuring device, such as a ruler or caliper; and combinations of these.

System 10 can further comprise one or more lyophilization devices, device 606 shown, such as a device configured to preserve a product (e.g. ECM 120) via a low temperature dehydration process. In some embodiments, lyophilization device 606 is configured to dehydrate the product residual moisture content of between 0.1% and 10%, such as a residual moisture content between 0.5% and 4%, such as a residual moisture content of less than 4% (e.g. the moisture content as measured via the Karl-Fischer moisture content test). In some embodiments, lyophilization device 606 is configured to dehydrate the product to a residual moisture content of between 0.2% and 2.5%. The low temperature dehydration process executed by lyophilization device 606 can comprise four primary phases: freezing, annealing, primary drying (sublimation), and secondary drying (adsorption). First, the freezing phase can be configured to cool the product within lyophilization device 606 to a temperature below its triple point to ensure later sublimation, thereby preserving the product's physical form. Secondly, the annealing phase stabilizes the molecular crystalline structure to minimize disruptions during drying. During the primary drying phase a lower pressure within lyophilization device 606, increase in temperature within lyophilization device 606, can be configured to promote water sublimation until most of the water was been sublimated. Finally, the secondary drying phase can be configured to maintain or further increase the temperature of the product to promote removal of ionically-bound water molecules (e.g. break the bonds between the product and the water molecules).

System 10 can further comprise one or more lyophilization receptacles, receptacle 607 shown, which can be configured for use with lyophilization device 606 described herein. Receptacle 607 can be configured to receive a product (e.g. ECM 120) and can be placed within lyophilization device 606 for the duration of the dehydration process. Receptacle 607 can comprise a material selected from the group consisting of: aluminum; stainless steel; glass; plastic; and combinations of these. Additionally, receptacle 607 can be depyrogenated, such as to prevent contamination of the product from pathogens on receptacle 607. In some embodiments, receptacle 607 is inserted into a storage element, such as a self-sealing pouch, prior to its placement within lyophilization device 606.

System 10 can further comprise one or more tubes, tube 608 shown, which can be configured to store an object (e.g. ECM 120). Tube 608 can include a top, or other moveable cover.

System 10 can further comprise one or more batch mills, mill 609 shown, which can be configured to grind soft, fibrous, and/or brittle products (e.g. ECM 120). Mill 609 can be configured to receive tube 608, as described herein, and grind the product within tube 608. In some embodiments, the products are first frozen or maintained in a frozen state through the use of liquid nitrogen and/or dry ice (i.e. cryogrinding).

System 10 can further comprise one or more containers, bottle 610 shown, which can be configured to store one, two, or more fluids, powders, capsules, and the like. Bottle 610 can include a top, or other moveable cover. Bottle 610 can comprise a material selected from the group consisting of: glass; plastic, such as polypropylene, polyethylene, cyclic olefin copolymer; metal, such as stainless steel; and combinations of these. In some embodiments, Bottle 610 has a volume of 0.1 L to 5 L, such as 1 L.

System 10 can further comprise one or more material removal and/or displacement devices, material device 611 shown, which can be configured to shape or otherwise alter a surface of a product. Material device 611 can be configured to perform a function selected from the group consisting of: drill; grind; rout; plane; bore; cut; and combinations of these.

System 10 can further comprise one or more tensile tester devices, device 612 shown, which can be configured to determine the tensile or compressive stresses or forces generated by the material (e.g. ECM 120) under displacements or deformations.

System 10 can further comprise one or more alignment assemblies, assembly 613 shown. In some embodiments, alignment assembly 613 comprises a Dremel keyless chuck configured to secure an object therein (e.g. support assembly 300, device 400, etc.).

System 10 can further comprise one or more pin assemblies, assembly 614 shown. In some embodiments, pin assembly 614 comprises a Dremel keyless chuck configured to secure a pin, needles, and/or other sharpened object therein. In some embodiments, the pin comprises an outer diameter of 0.7 mm.

Figure 23:
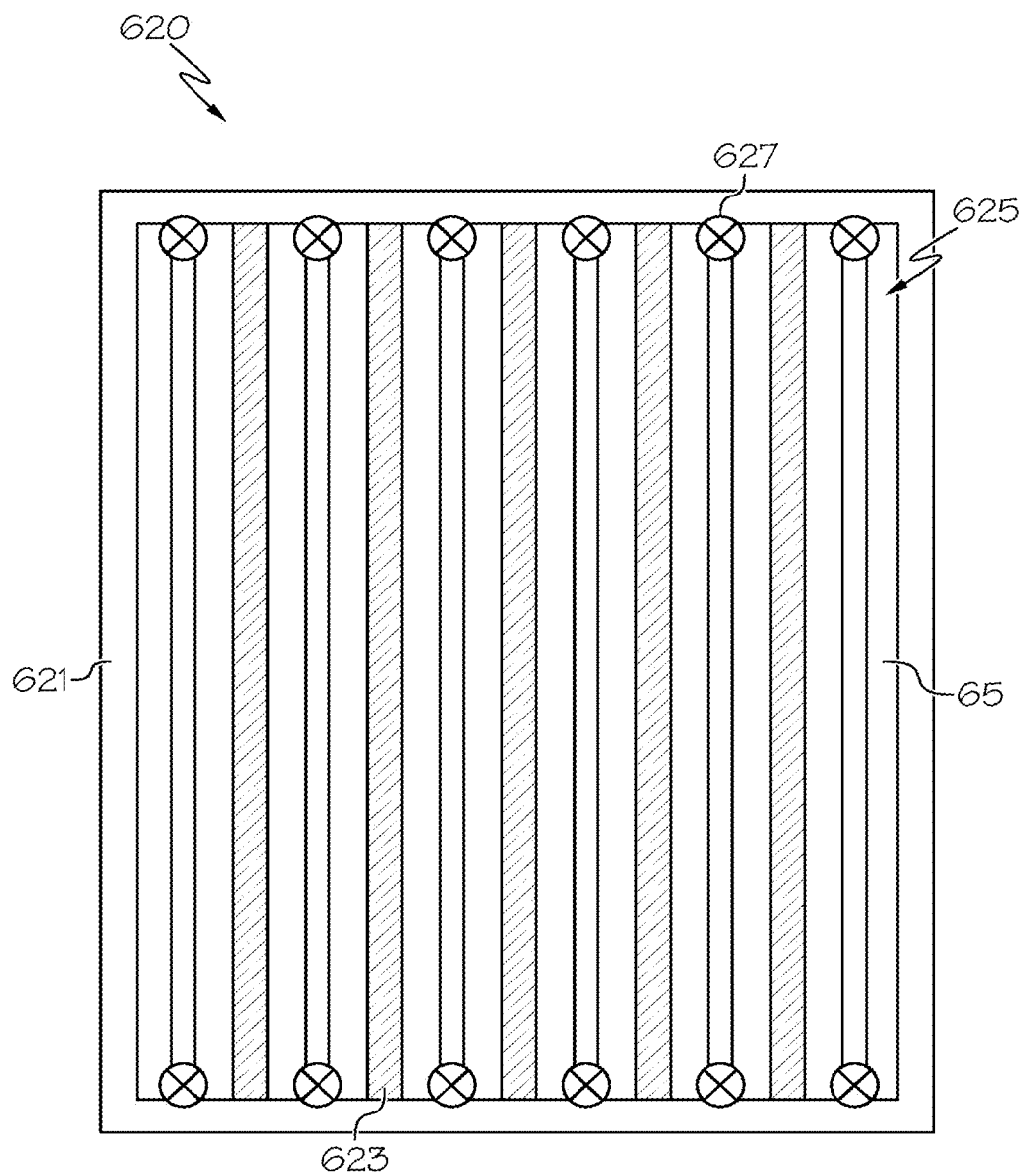
FIG. 23 illustrates a schematic view of a cassette for securing one or more nerve segments, consistent with the present inventive concepts.

System 10 can further comprise one or more nerve cassettes, cassette 620 shown, and as described herein in reference to FIG. 23.

System 10 can further comprise one or more buffer solutions, solution 701 shown, which can be configured to resist changes in pH when an acid and/or alkali is added to it (e.g. maintain a constant pH). In some embodiments, solution 701 comprises phosphate buffered solution or phosphate buffered saline (PBS). In some embodiments, solution 701 has a conductivity of between 1 and 30 mS/cm, such as 14 mS/cm. In some embodiments, solution 701 comprises a buffer solution in water with the components and ranges of concentration shown herebelow in Table 2:

TABLE 2

| Buffer Solutions | | |
|---|---|---|
| Buffer/ Neutralizing Component | Range Conc (g/L) | Preferred Conc (g/L) 7.5-15 mg/mL |
| NaOH | 0.1-3.0 g/L | 0.5-1.01 |
| KCl | 0.01-1.0 g/L | 0.22 |
| NaH$_2$PO$_4$ | 0.1-1.5 g/L | 0.60 |
| NaCl | 0.3-9.0 g/L | 3.51 |
| Na$_2$HPO$_4$ | 0.1-10.0 g/L | 2.84 |

System 10 can further comprise one or more cooling agents, agent 702 shown, which can be configured to reduce, and/or otherwise regulate, the temperature of a product (e.g. raw material 65). Cooling agent 701 can comprise an agent selected from the group consisting of: dry ice; dry ice with ethanol; dry ice with acetone; liquid nitrogen; wet ice; frozen ice packs; and combinations of these.

System 10 can further comprise one or more purified waters, water 703 shown, which can comprise water that has been filtered, or otherwise processed, to remove one, two, or more impurities. In some embodiments, purified water 703 comprises Type I water or water for injection.

System 10 can further comprise one or more dissociation solutions, solution 704 shown, which can be configured to dissociate adherent cells, cell aggregates, and/or tissues into single-cell suspensions. In some embodiments, dissociation solution 704 comprises a co-solution comprising 0.02% trypsin and 0.05% ethylenediaminetetraacetic acid (EDTA). Dissociation solution 704 can comprise a solution that is warmed to a temperature of approximately 35° C.

System 10 can further comprise one or more disinfecting solutions, solution 705 shown, which can be configured to destroy one, two, or more microorganisms (e.g. bacteria, virus, fungi). In some embodiments, disinfecting solution 705 comprises a co-solution comprising 0.1% peracetic acid and 4% ethanol.

System 10 can further comprise one or more detergent solutions, solution 706 shown, which can be configured to lyse and/or permeabilize cells. In some embodiments, detergent solution 706 comprises Triton X-100. In some embodiments, detergent solution 706 comprises a sodium deoxycholate solution.

System 10 can further comprise one or more sucrose solutions, solution 707 shown, which can be configured as an excipient. In some embodiment, sucrose solution 707 comprises a 1M sucrose solution.

System 10 can further comprise one or more sterile waters, water 708 shown, which can comprise water that has been processed to remove one, two, or more contaminants (e.g. bacteria, virus, fungi). In some embodiments, sterile water 708 comprises water for injection (WFI).

System 10 can further comprise one or more digestion solutions, solution 709 shown, which can be configured to break down tissue. In some embodiments, digestion solution 709 comprises a 0.01 N hydrochloric acid (HCl) solution.

System 10 can further comprise one or more digestive enzymes, enzyme 710 shown, which can be configured to break down polymeric macromolecules. In some embodiments, the digestive enzyme comprises pepsin comprising an activity level of between 0.5 U/mg and 5000 U/mg, such as an activity level of approximately 2500 U/mg. Enzyme 710 is then placed into solution 709 such that the final concentration results in an activity level of between 10 U/mL and 2500 U/mL, such as activity levels of 250 U/mL.

System 10 can further comprise one or more excipients, excipient 711 shown, which can be configured to provide at least one of long-term stabilization, bulking, radioprotection, heat protection, cryoprotection, increase in solubility, increase or decrease in viscosity, optimization of thermal properties for lyophilization and/or other enhancement of a product. Excipient 711 can comprise an excipient selected from the group consisting of: sucrose; ascorbic acid, glycerol, sodium ascorbate; sodium azide; vitamin E; EDTA; mannitol; glycine; Dextran; and combinations of these. Excipient 711 can be configured to increase, and/or otherwise improve, the relative solubility of a product (e.g. ECM 120). Excipient 711 can be configured to increase, or otherwise improve, the relative gelation of a product (e.g. ECM 120).

System 10 can further comprise one or more tools, tool 80 shown. Tool 80 can comprise a tool configured to coat a surface (e.g. a surface of a deposit site), such as an atomization tool, a brush or brushing tool, and/or a dipping tool, as described herein. Tool 80 can comprise a tool consisting of a tattoo machine for surface delivery of ECM 120 at a defined depth. Tool 80 can comprise a jet injector to deliver ECM 120 via high pressure at a defined depth. Tool 80 can comprise a bobbin with a coiled strand or ribbon embedded with ECM 120 wound/canvassed around the surface. Tool 80 can comprise an adhesive or adhesive strip used to affix ECM 120 to a surface.

Figure 24:
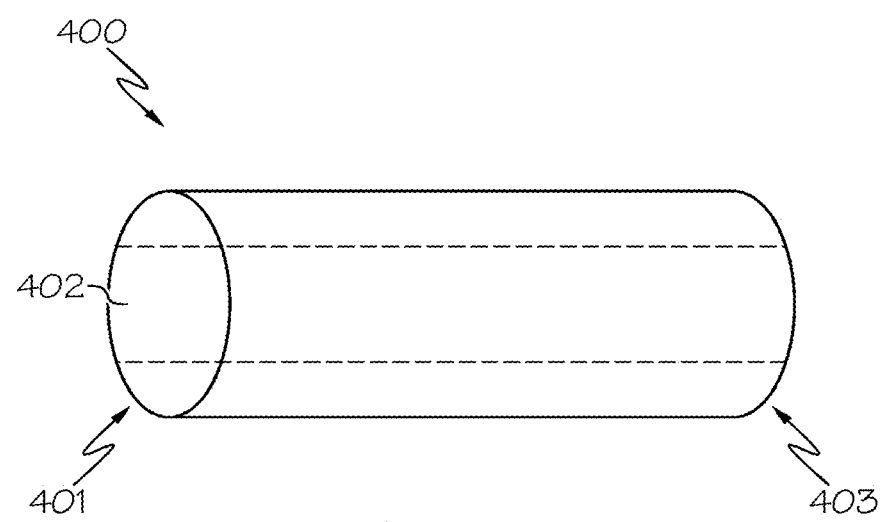
FIG. 24 illustrates a perspective view of a medical device comprising a nerve-graft conduit, consistent with the present inventive concepts.

System 10 can further comprise one or more nerve graft-conduits, device 400 shown, and as described in reference to FIG. 24.

Referring now to FIG. 2, a perspective view of a medical device comprising a graft-conduit combination is illustrated, consistent with the present inventive concepts. Implant 20 comprises a graft-conduit (e.g. artificial, natural) configured to connect, or otherwise provide one, two, or more longitudinal channels, between two or more anatomical elements (e.g. nerve stumps). Implant 20 can comprise at least a first end 21 and at least a second end 23, with a lumen 22 therebetween. First end 21 can be constructed and arranged to receive at least a portion of a first anatomical element (e.g. first nerve stump) and second end 23 can be constructed and arranged to receive at least a portion of a second anatomical element (e.g. second nerve stump).

Lumen 22 can be configured to receive, or otherwise comprise, a therapeutic device (e.g. device 100 of the present inventive concepts), such as to maintain the relative positioning of the therapeutic device between the two or more anatomical elements. Alternatively or additionally, first end 21 and/or second end 23 can be configured to receive, or otherwise comprise, a therapeutic device (e.g. device 100 of the present inventive concepts), such that the therapeutic device contacts at least a portion of the anatomical elements received by first end 21, second end 23.

Implant 20 can comprise an inner diameter ID that approximates the outer diameter of at least one of the anatomical elements (e.g. a nerve stump). Implant 20 can comprise an inner diameter (ID) that is smaller than the outer diameter of at least one of the anatomical elements (e.g. a nerve stump). Implant 20 can comprise an outer diameter (OD) that approximates the outer diameter of at least one of the anatomical elements (e.g. a nerve stump). In some embodiments, implant 20 comprises an ID and/or OD that are consistent along its length. In some embodiments, implant 20 comprises an ID and/or OD that vary along its length, such as an initial $ID_i$ and/or $OD_i$ to adapt to the diameter of a first anatomical element and a final $ID_f$ and/or $OD_f$ to adapt to the diameter of a second anatomical element (not shown). In some embodiments, implant 20 comprises a funnel shape configured to allow for expansion and/or contraction of the ID and/or OD along its length. Implant 20 can comprise a length L that approximates the distance between the two or more anatomical elements. In some embodiments, implant 20 comprises a length L that is greater than the distance between the two or more anatomical elements, such as to overlap at least a portion of at least one of the anatomical elements (as shown). Alternatively or additionally, implant 20 can comprise an initial length $L_I$ that is modified (e.g. trimmed or otherwise reduced) to comprise a final length $L_F$. The length of implant 20 can be modified prior to, during, and/or after the procedure in which implant 20 is implanted in the patient.

Implant 20 can comprise one, two, or more severable portions 24 (not shown) proximate first end 21 and/or second end 23. Severable portions 24 can be removed prior to, during, and/or after the procedure in which implant 20 is implanted in the patient, such as to modify the length of implant 20. In some embodiments, severable portions 24 are configured to be torn away from the remainder of implant 20. In some embodiments, severable portions 24 are configured to be cut away from the remainder of implant 20. For example, implant 20 (e.g. lumen 22) comprises a volume of device 100 that contracts after implantation within the patient. A clinician can remove at least one severable portion 24 comprising a portion of implant 20 that no longer comprises a volume of device 100 (e.g. a portion of implant 20 from which device 100 has contracted away).

Implant 20 can be configured to accept nerves in multiple orientations, such as a T-shaped implant for an end-to-side repair or a Y-shaped implant for connecting one nerve to two other nerves. In some embodiments, implant 20 comprises an angled connector configured to receive one, two, or more tissues.

Implant 20 can comprise one, two, or more materials configured to promote the growth of tissue (e.g. nerve tissue). In some embodiments, at least a portion of implant 20 comprises a material that is permeable to cells and/or nutrients (e.g. tissue cells can infiltrate the material of implant 20). In some embodiments, at least a portion of implant 20 comprises a selective permeability to pre-determined nutrients and/or cell types. In some embodiments, at least a portion of implant 20 comprises a material that supports, or otherwise promotes, tissue growth (e.g. the material comprises an agent 70 comprising growth factors). Alternatively or additionally, implant 20 can comprise one, two, or more materials configured to impede the growth of tissue (e.g. nerve tissue). In some embodiments, at least a portion of implant 20 comprises a material that is impermeable to cells and/or nutrients (e.g. tissue cells cannot infiltrate the material of implant 20). For example, a first portion of implant 20 can comprise a permeable material and a second portion of implant 20 can comprise an impermeable material.

Implant 20 can comprise one, two, or more materials configured to provide suture retention strength, such that implant 20 can receive one or more sutures and withstand the respective tractive force. Implant 20 can comprise a suture retention strength of no less than 0.02N, such as no less than 0.2N, such as no less 0.5N.

Implant 20 can be constructed and arranged to withstand tension, flexion, and/or torsion forces exhibited between the two or more anatomical elements (e.g. two or more nerve stumps), such as to withstand motion attributed to characteristic body and/or surrounding tissue movement.

Implant 20 can be constructed and arranged to prevent, or otherwise resist, the formation of one or more kinks along its length. In some embodiments, implant 20 is configured to resist kink and/or compressive collapse during a bending of a joint, such as a finger or elbow.

Implant 20 can comprise one, two, or more materials configured to degrade at a rate compatible with the rate of tissue regeneration. Nerves can comprise a longitudinal regeneration rate between approximately 1 mm/day and 5 mm/day, and as such, implant 20 can comprise a corresponding degradation rate. For example, implant 20 comprising a length of 2 cm can be configured to degrade no earlier than 20 days after implantation. Alternatively, implant 20 can comprise a degradation rate that is slower than the longitudinal tissue regeneration rate, such as to allow for sufficient nerve volume regeneration and terminal functional recovery to occur. For example, a nerve with a gap injury of 1 cm can be expected to be crossed by growing axons from proximal to distal nerve stump in no less than 10 days (assuming a longitudinal regeneration rate of 1 mm/day). However, robust structural tissue formation between the two nerve stumps likely requires more than 20 days and full functional recovery likely requires more than one month. Therefore, the implant 20 can be configured to degrade at a slower rate than that of the nerve healing and/or regeneration process.

Implant 20 can comprise a degradable, artificial conduit configured to break down in situ over one, two, or more periods of time. In some embodiments, implant 20 comprises a non-degradable artificial conduit, such as a conduit comprising silicone. Lumen 22 can comprise device 100 (e.g. ECM 120) comprising a hydrogel configuration, such as a degradable or non-degradable hydrogel.

Implant 20 can comprise a natural conduit harvested, or otherwise derived, from a tissue source. Implant 20 can further comprise a decellularized, natural conduit. Implant 20 can comprise a decellularized tissue that has been modified to create one, two, or more lumens (e.g. longitudinal tunnels/channels) of a controlled size. Lumen 22 can comprise device 100 (e.g. ECM 120) comprising a hydrogel configuration, such as a degradable or non-degradable hydrogel. In some embodiments, implant 20 comprises a conduit harvested, or otherwise derived, from porcine tissue (e.g. porcine nerve-tissue). In some embodiments, implant 20 comprises a composite of device 100 and one, two, or more other materials, such as a material selected from the group consisting of: polycaprolactone; PLLA; PGA; silicone; polyurethanes; PET; PTFE; decellularized tissue and/or organs; collagen; elastin; GAG; keratin; chitosan; silk; synthetic derived materials; naturally derived materials; and combinations of these.

Implant 20 can comprise a conduit at least partially derived, or otherwise fabricated, from device 100 (e.g. ECM 120). Implant 20 can comprise a conduit fabricated from raw material 65 comprising a decellularized extracellular matrix (e.g. ECM 120), such as a raw material as described in applicant's co-pending International PCT Patent Application Serial Number PCT/US2020/053570, entitled "Extracellular Matrix Devices and Methods of Manufacture", filed Sep. 30, 2020. Raw material 65 can be mechanically, physically, and/or chemically modified to create a conduit with a lumen therethrough, such as described herein in reference to Method 1000 of FIG. 5.

Implant 20 can further comprise one, two, or more cavities, spaces, and/or other reservoirs, reservoirs 25 (not shown). Reservoirs 25 can be configured to contain a volume of device 100 (e.g. ECM 120). Device 100 can be injected into implant 20 such that lumen 22 and reservoir 25 each receive a volume of device 100. As the volume of device 100 contracts within lumen 22 (e.g. contracts over time), the volume of device 100 within reservoir 25 can be pulled into lumen 22 to provide an additional supply of device 100. In some embodiments, reservoir 25 is constructed and arranged as a recess within an inner wall of implant 20. For example, device 100 can comprise a plurality of reservoirs 25 constructed and arranged along a length of implant 20. As another example, device 100 can comprise at least one reservoir 25 constructed and arranged proximate first end 21 and/or second end 23.

As described herein in reference to FIG. 2, implant 20 can be constructed to comprise device 100 (e.g. ECM 120) and/or can be configured to receive a volume of device 100 (e.g. ECM 120).

Referring to FIGS. 3A-P, various deployment assemblies for a medical device are illustrated, consistent with the present inventive concepts. FIGS. 3A-P are described using the various components of system 10 described herein in reference to FIG. 1. Deployment assembly 200 can comprise various components configured for the deployment of device 100 (e.g. ECM 120) to a deposit site of a patient. Deployment assembly 200 can comprise at least one of the following components: vial 210; syringe 220; needle 240; connector 260; vial adaptor 280; homogenizer 290; or combinations of these. In some embodiments, homogenizer 290 is constructed and arranged as a component of connector 260.

Deployment assembly 200 can further comprise one, two, or more support containers 205 within which the other components of deployment assembly 200 are organized. In some embodiments, deployment assembly 200 further comprises one, two, or more presentation containers 207 within which the one, two, or more support containers 205 are organized. Container 205 can further include one, two, or more sub-containers 203. In some embodiments, one, two, or more components of deployment assembly 200 are contained within a distinct sub-container 203. Sub-container 203 can comprise a similar or dissimilar configuration and/or material as containers 205 and/or 207.

One or more components of deployment assembly 200 (e.g. container 207) can include one or more indicators, sensors, transducers, and/or other functional elements 299. Functional element 299 can comprise one or more functional elements positioned on and/or within a container 203, 205, and/or 207, vial 210, syringe 220, needle 240, connector 260, vial adaptor 280, and/or another component of deployment assembly 200. Functional element 299 can be connected to one or more wires, electrical conductors, optical fibers, tubes (e.g. fluid delivery, hydraulic, and/or pneumatic tubes), wave guides, and/or other conduits (not shown) that transport signals (e.g. information), energy, heat, electricity, fluid, light, and/or sound to and/or from functional element 299 from and/or to another component (e.g. another component of deployment assembly 200). In some embodiments, functional element 299 comprises a temperature indicator strip configured to provide a signal (e.g. visual, auditory, tactile, etc.) when one, two, or more components of deployment assembly 200 have been exposed to a temperature above, below, and/or at a threshold. For example, functional element 299 can be configured to indicate when a vial 210 has been exposed to a temperature greater than or equal to 29° C. In some embodiments, functional element 299 comprises a pressure indicator and/or over pressure relief valve to prevent damage to the injected nerve.

As described herein in reference to FIGS. 3A-P, deployment assembly 200 can be configured to deploy at least a portion of device 100 described herein.

Referring now to FIG. 3A, an embodiment of deployment assembly 200 is shown. Deployment assembly 200 of FIG. 3A comprises three support containers 205a-c, one presentation container 207, three vials 210a-c, two syringes 220a, b, four needles 240a-d, and one connector 260. Container 205a can comprise vial 210a comprising ECM 120. Container 205b can comprise vial 210b comprising neutralizing element 140. Container 205c can comprise vial 210c comprising reconstituting element 160. Container 205c can further comprise syringes 220a,b, needles 240a-d, and connector 260. In some embodiments, vial 210c, each syringe 220a,b, each needle 240a-d, and connector 260 are further contained in sub-containers 203a-h. Container 207 can be constructed and arranged to comprise containers 205a-c.

Referring now to FIG. 3B, yet another embodiment of deployment assembly 200 is shown. Deployment assembly 200 of FIG. 3B comprises three support containers 205a-c, one presentation container 207, two vials 210a,b, two syringes 220a,b, one needle 240, one connector 260, and two vial adaptors 280a,b. Container 205a can comprise vial 210a comprising ECM 120. Container 205b can comprise vial 210b comprising neutralizing element 140. Container 205c can comprise syringes 220a,b, needle 240, connector 260, and vial adaptors 280a,b. In some embodiments, syringe 220a comprises reconstituting element 160. In some embodiments, each syringe 220a,b, needle 240, connector 260, and each vial adaptor 280a,b is further contained in sub-containers 203a-f. Container 207 can be constructed and arranged to comprise containers 205a-c.

Referring now to FIG. 3C, yet another embodiment of deployment assembly 200 is shown. Deployment assembly 200 of FIG. 3C comprises three support containers 205a-c, one presentation container 207, one vial 210, two syringes 220a,b, one needle 240, one connector 260, and one vial adaptor 280. Container 205a can comprise vial 210 comprising ECM 120. Container 205b can comprise syringe 220a comprising neutralizing element 140. Container 205c can comprise syringe 220b, needle 240, connector 260, and vial adaptor 280. In some embodiments, syringe 220b comprises reconstituting element 160. In some embodiments, syringe 220b, needle 240, connector 260, and vial adaptor 280 are further contained in sub-containers 203a-d. Container 207 can be constructed and arranged to comprise containers 205a-c.

Referring now to FIG. 3D, yet another embodiment of deployment assembly 200 is shown. Deployment assembly 200 of FIG. 3D comprises three support containers 205a-c, one presentation container 207, one vial 210, two syringes 220a,b, one needle 240, one connector 260, and one vial adaptor 280. Container 205a can comprise vial 210 comprising ECM 120. Container 205b can comprise syringe 220a comprising co-solution of neutralizing element 140 and reconstituting element 160. Container 205c can comprise syringe 220b, needle 240, connector 260, and vial adaptor 280. In some embodiments, syringe 220b, needle 240, connector 260, and vial adaptor 280 are further contained in sub-containers 203a-d. Container 207 can be constructed and arranged to comprise containers 205a-c.

Referring now to FIG. 3E, yet another embodiment of deployment assembly 200 is shown. Deployment assembly 200 of FIG. 3E comprises two support containers 205a,b, one presentation container 207, three syringes 220a-c, one needle 240, and one connector 260. Container 205a can comprise syringe 220a comprising ECM 120. Container 205a can further include a separate plunger 212 configured to be attached to syringe 220a. Container 205b can comprise syringes 220b,c, needle 240, and connector 260. In some embodiments, syringe 220b comprises neutralizing element 140 and syringe 220c comprises reconstituting element 160. In some embodiments, each syringe 220b,c, needle 240, and connector 260 are further contained in sub-containers 203a-d. Container 207 can be constructed and arranged to comprise containers 205a,b.

Referring now to FIG. 3F, yet another embodiment of deployment assembly 200 is shown. Deployment assembly 200 of FIG. 3F comprises two support containers 205a,b, one presentation container 207, two syringes 220a,b, one needle 240, and one connector 260. Container 205a can comprise syringe 220a comprising ECM 120. Container 205a can further include a separate plunger 212 configured to be attached to syringe 220a. Container 205b can comprise syringe 220b, needle 240, and connector 260. In some embodiments, syringe 220b comprises reconstituting element 160. Container 207 can be constructed and arranged to comprise containers 205a,b.

Referring now to FIG. 3G, yet another embodiment of deployment assembly 200 is shown. Deployment assembly 200 of FIG. 3G comprises one support container 205, one presentation container 207, two syringes 220a,b, one needle 240, and one connector 260. Container 205 can comprise syringes 220a,b, needle 240, and connector 260. Container 205 can further include a separate plunger 212 configured to be attached to syringe 220a. In some embodiments, syringe 220a comprises ECM 120 and syringe 220b reconstituting element 160. Container 207 can be constructed and arranged to comprise container 205.

Referring now to FIG. 3H, yet another embodiment of deployment assembly 200 is shown. Deployment assembly 200 of FIG. 3H comprises two support containers 205a,b, one presentation container 207, one vial 210, three syringes 220a-c, one needle 240, and one vial adaptor 280. Container 205a can comprise vial 210 comprising ECM 120 and vial adaptor 280. Container 205b can comprise syringes 220a-c and needle 240. In some embodiments, syringe 220a comprises neutralizing element 140 and syringe 220b comprises reconstituting element 160. Container 207 can be constructed and arranged to comprise containers 205a,b.

Referring now to FIG. 3I, yet another embodiment of deployment assembly 200 is shown. Deployment assembly 200 of FIG. 3I comprises three support containers 205a-c, one presentation container 207, one vial 210, three syringes 220a-c, one needle 240, and one vial adaptor 280. Container 205a can comprise vial 210 comprising ECM 120 and vial adaptor 280. Container 205b can comprise syringes 220a,b and needle 240. In some embodiments, syringe 220a comprises a co-solution of neutralizing element 140 and reconstituting element 160. Container 205c can comprise syringe 220c. Container 207 can be constructed and arranged to comprise containers 205a-c.

Referring now to FIG. 3J, yet another embodiment of deployment assembly 200 is shown. Deployment assembly 200 of FIG. 3J comprises two support containers 205a,b, one presentation container 207, two vials 210a,b, two syringes 220a,b, one needle 240, and two vial adaptors 280a,b. Container 205a can comprise vial 210a comprising ECM 120 and vial adaptor 280a. Container 205b can comprise vial 210b, syringes 220a,b, needle 240, and vial adaptor 280b. In some embodiments, vial 210b comprises a co-solution of neutralizing element 140 and reconstituting element 160. In some embodiments, vial 210b, each syringe 220a,b, needle 240, and vial adaptor 280b are further contained in sub-containers 203a-e. Container 207 can be constructed and arranged to comprise containers 205a,b.

Referring now to FIG. 3K, yet another embodiment of deployment assembly 200 is shown. Deployment assembly 200 of FIG. 3K comprises two support containers 205a,b, one presentation container 207, two vials 210a,b, two syringes 220a,b, one needle 240, and two vial adaptors 280a,b. Container 205a can comprise vial 210a comprising ECM 120 and vial adaptor 280a. Container 205b can comprise vial 210b, syringes 220a,b, needle 240, and vial adaptor 280b. In some embodiments, vial 210b comprises neutralizing element 140 and syringe 220a comprises reconstituting element 160. In some embodiments, vial 210b, each syringe 220a,b, needle 240, and vial adaptor 280 are further contained in sub-containers 203a-e. Container 207 can be constructed and arranged to comprise containers 205a,b.

Referring now to FIG. 3L, yet another embodiment of deployment assembly 200 is shown. Deployment assembly 200 of FIG. 3L comprises one support container 205, one presentation container 207, two vials 210a,b, two syringes 220a,b, one needle 240, and two vial adaptors 280a,b.

Container 205 can comprise vials 210a,b, syringes 220a,b, needle 240, and vial adaptors 280a,b. In some embodiments, vial 210a comprises ECM 120 and vial 210b comprises neutralizing element 140. In some embodiments, syringe 220a comprises reconstituting element 160. In some embodiments, each vial 210a,b, each syringe 220a,b, needle 240, and each vial adaptor 280a,b is further contained in sub-containers 203a-g. Container 207 can be constructed and arranged to comprise container 205.

Referring now to FIG. 3M, yet another embodiment of deployment assembly 200 is shown. Deployment assembly 200 of FIG. 3M comprises one support container 205, one presentation container 207, two vials 210a,b, two syringes 220a,b, one needle 240, and two vial adaptors 280a,b. Container 205 can comprise vials 210a,b, syringes 220a,b, needle 240, and vial adaptors 280a,b. In some embodiments, vial 210a comprises ECM 120 and vial 210b comprises a co-solution of neutralizing element 140 and reconstituting element 160. In some embodiments, each vial 210a,b, each syringe 220a,b, needle 240, and each vial adaptor 280a,b is further contained in sub-containers 203a-g. Container 207 can be constructed and arranged to comprise container 205.

Referring now to FIG. 3N, yet another embodiment of deployment assembly 200 is shown. Deployment assembly 200 of FIG. 3N comprises two support containers 205a,b, one presentation container 207, three vials 210a-c, two syringes 220a,b, one needle 240, and three vial adaptors 280a-c. Container 205a can comprise vial 210a comprising ECM 120 and vial adaptor 280a. Container 205b can comprise vials 210b,c, syringes 220a,b, needle 240, and vial adaptors 280b,c. In some embodiments, vial 210b comprises neutralizing element 140 and vial 210c comprises reconstituting element 160. In some embodiments, each vial 210b,c, each syringe 220a,b, needle 240, and each vial adaptor 280b,c is further contained in sub-containers 203a-g. Container 207 can be constructed and arranged to comprise containers 205a,b.

Referring now to FIG. 3O, yet another embodiment of deployment assembly 200 is shown. Deployment assembly 200 of FIG. 3O comprises two support containers 205a,b, one presentation container 207, two syringes 220a,b, one needle 240, and one connector 260. Container 205a can comprise syringe 220a comprising ECM 120. Container 205b can comprise syringe 220b, needle 240, and connector 260. Container 205b can further include a separate plunger 212 configured to be attached to syringe 220a. In some embodiments, syringe 220b comprises reconstituting element 160. Container 207 can be constructed and arranged to comprise containers 205a,b.

Referring now to FIG. 3P, yet another embodiment of deployment assembly 200 is shown. Deployment assembly 200 of FIG. 3P comprises two support containers 205a,b, two presentation containers 207a,b, two syringes 220a,b, one needle 240, and one connector 260. Container 205a can comprise syringe 220a comprising ECM 120. Container 205b can comprise syringe 220b, needle 240, and connector 260. Container 205b can further include a separate plunger 212 configured to be attached to syringe 220a. In some embodiments, syringe 220b comprises reconstituting element 160. In some embodiments, syringe 220b comprises neutralizing element 140. In some embodiments, syringe 220b comprises a co-solution of neutralizing element 140 and reconstituting element 160. Containers 207 a,b can be constructed and arranged to comprise containers 205a,b, respectively.

Referring now to FIGS. 4A and B, a perspective view and an end view of an embodiment of a support assembly for manufacturing a graft, conduit, or graft-conduit combination comprising an extracellular matrix are illustrated, respectively, consistent with the present inventive concepts. Support assembly 300i can be configured to receive device 100, device 400, and/or ECM 120. Support assembly 300i can comprise a first portion 310 and a second portion 320. Support assembly 300i can be constructed and arranged as a cylindrical tube with a lumen 305 therethrough and each portion 310, 320 can be constructed and arranged as a horizontal cylindrical segment. Portions 310, 320 can be rotatably coupled via a hinge 307, such that when rotated from an open configuration (as shown in FIG. 4A) to a closed configuration (as shown in FIG. 4B), portions 310, 320 cooperate to form lumen 305. Support assembly 300i can further comprise one, two, or more retention elements 308 configured to secure portions 310, 320 in the closed configuration.

Support assembly 300i (e.g. portions 310, 320) can comprise a plurality of pores 309. Each pore 309 can have a diameter of between 0.1 micron and 500 microns. Pores 309 can be distributed uniformly along the longitudinal and/or circumferential directions of support assembly 300i. In some embodiments, pores 309 are configured to allow for the passage of a fluid between support assembly 300i (e.g. device 100, device 400, and/or ECM 120 therein) and an external environment. In some embodiments, a vacuum source is applied to support assembly 300i and pores 309 are configured to apply a uniform vacuum to device 100, device 400, and/or ECM 120 within support assembly 300i. The vacuum source can be configured to maintain uniform contact between an outer surface of device 100, device 400, and/or ECM 120 and an inner surface of support assembly 300i. One or more thermal and/or physical treatments can be applied concurrently with the vacuum source, such as to induce the formation of coaxial layers within raw material 65 as a result of tissue contraction and/or shearing.

Support assembly 300i (e.g. portions 310, 320) can comprise a material selected from the group consisting of: expanded and non-expanded poly fluoro tetraethylene; polysulfones; cellulose acetate; polyamide; polyvinylidene fluoride; polysulfone; polyethersulfone; polyvinyl chloride; polyimide; polyacrylonitrile; polyethylene glycol; polyvinyl alcohol; poly(methacrylic acid); poly(arylene ether ketone); poly(ether imide); and polyaniline nanoparticles; stainless steel, such as 316L stainless steel; aluminum; cobalt alloy; titanium alloy; and combinations of these.

Support assembly 300i can further comprise one, two, or more elements configured to impart structural modifications to device 100, device 400, and/or ECM 120. For example, support assembly 300i can be configured to impart a plurality of channels to device 100, device 400, and/or ECM 120 via ablation and/or sublimation processes using an excimer laser.

As described herein in reference to FIGS. 4A and B, support assembly 300i and the related methods can be configured to manufacture at least a portion of implant 20, device 100, device 400, and/or ECM 120 described herein.

Figure 5:
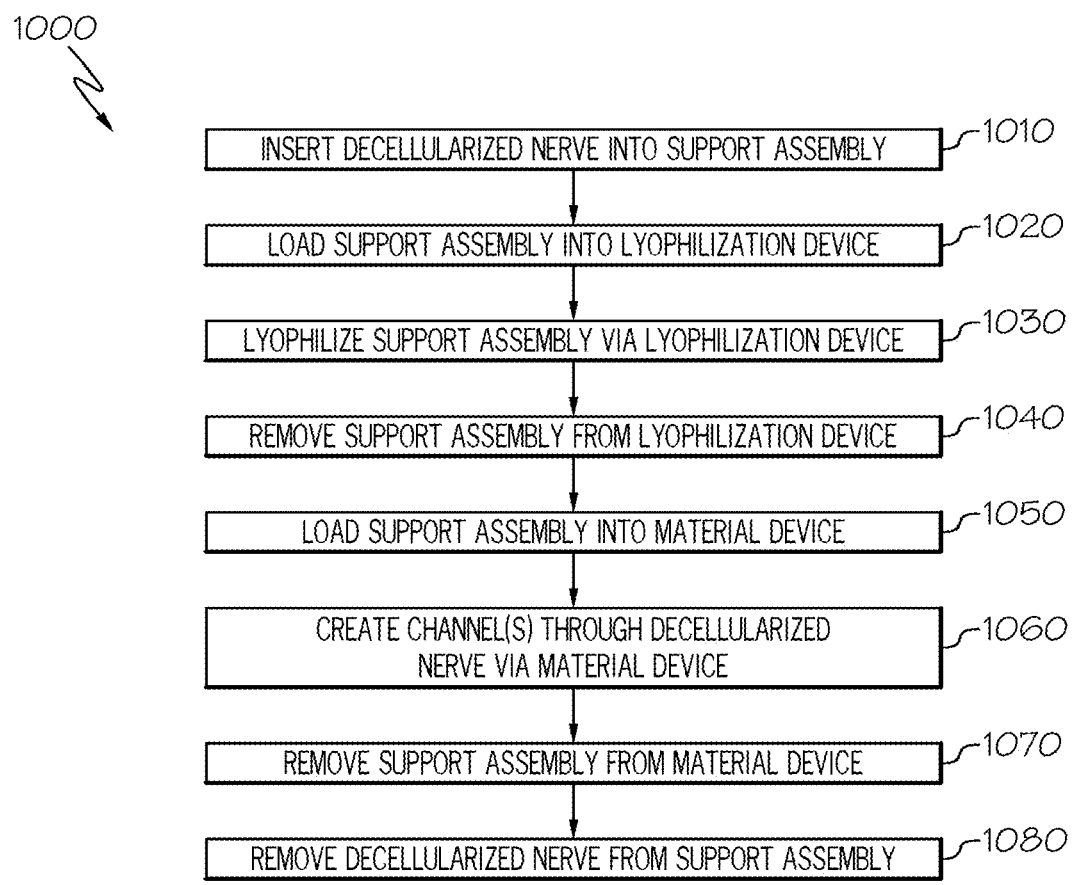
FIG. 5 illustrates a method for manufacturing a conduit comprising an extracellular matrix, consistent with the present inventive concepts.

Referring now to FIG. 5, a method for manufacturing a conduit comprising an extracellular matrix is illustrated, consistent with the present inventive concepts. Method 1000 can be configured to manufacture implant 20 comprising ECM 120 (e.g. raw material 65 harvested from tissue source 60), as described herein. Raw material 65 can be harvested, processed, and decellularized according to the methods as described in applicant's co-pending International PCT Patent Application Serial Number PCT/US2020/053570, entitled "Extracellular Matrix Devices and Methods of Manufacture", filed Sep. 30, 2020, thereby producing ECM 120. In some embodiments, raw material 65 comprises a porcine nerve that is harvested, processed, and decellularized to produce ECM 120.

In STEP 1010, ECM 120 is inserted into lumen 305 of support assembly 300i or 300ii (as shown in FIGS. 4A,B and 22, respectively, and collectively support assembly 300 herein). Using support assembly 300i, ECM 120 can be placed into one of portions 310, 320 and the other portion can be rotated via hinge 307 to adopt the closed configuration, such that support assembly 300i encompasses ECM 120. Retention element 308 can secure portions 310, 320 in the closed configuration. Using support assembly 300ii, ECM 120 can be inserted into lumen 305 of support assembly 300ii using a thread anchoring ECM 120 at one end and such that ECM 120 can be pulled through lumen 305 of support assembly 300iii n a closed configuration to compress ECM 120 and secure it within support assembly 300ii.

In some embodiments, a vacuum source can be applied to support assembly 300, such as to maintain uniform contact between an outer surface of ECM 120 and an inner surface of support assembly 300. One or more thermal and/or physical treatments can be applied concurrently with the vacuum source, such as to induce the formation of coaxial layers within ECM 120 as a result of tissue contraction and/or shearing.

In other embodiments, the vacuum source can be maintained for an extended period of time around support assembly 300 to modify the hydration status and/or structural, morphological, mechanical, biological, and/or degradation properties of the ECM 120.

In some embodiments, one, two, or more pins, needles, suture threads, filaments, and the like can be inserted/threaded into at least a portion of ECM 120, such as to create one, two, or more channels (e.g. lumens) therethrough.

In STEP 1020, support assembly 300 comprising ECM 120 is loaded into lyophilization device 606.

In STEP 1030, lyophilization device 606 is configured to freeze support assembly 300 comprising ECM 120. In some embodiments, lyophilization device 606 is configured to freeze assembly 300 at a temperature between −60° C. and −20° C. for no less than four hours. In some embodiments, lyophilization device 606 is configured to apply a vacuum source to assembly 300. In some embodiments, the vacuum source comprises 100 to 200 micrometers of Hg. In some embodiments, lyophilization device 606 is configured to dry assembly 300 at a temperature of between −8° C. and 0° C., increasing the temperature over time. In some embodiments, lyophilization device 606 is configured to increase the temperature to between 0° C. and 25° C., such as a temperature of 20° C. (e.g. room temperature). In some embodiments, the total cycle duration can be configured to comprise a duration of between 12 and 66 hours, such as a duration between 18 and 24 hours, such as approximately 24 hours.

In STEP 1040, support assembly 300 comprising ECM 120 is removed from lyophilization device 606.

In STEP 1050, support assembly 300 comprising ECM 120 is loaded into material device 611.

In STEP 1060, material device 611 is configured to engage ECM 120 and drill or otherwise create a lumen/s therethrough. In some embodiments, material device 611 is configured to create a channel(s) (e.g. lumen/s) comprising a relatively constant diameter through ECM 120, and in some embodiments such that the diameter comprises a variance of no more than 100%.

In STEP 1070, support assembly 300 comprising ECM 120 is removed from material device 611.

In STEP 1080, ECM 120 is removed from support assembly 300. In some embodiments, pins that were inserted into ECM 120, as described hereabove, are removed.

Upon the conclusion of STEP 1080, ECM 120 can comprise a conduit constructed and arranged as implant 20. Implant 20 can be thawed, lyophilized, and/or dehydrated prior to sterilization and/or packaging.

As described herein in reference to FIG. 5, Method 1000 can be configured to manufacture at least a portion of implant 20 described herein.

Figure 6:
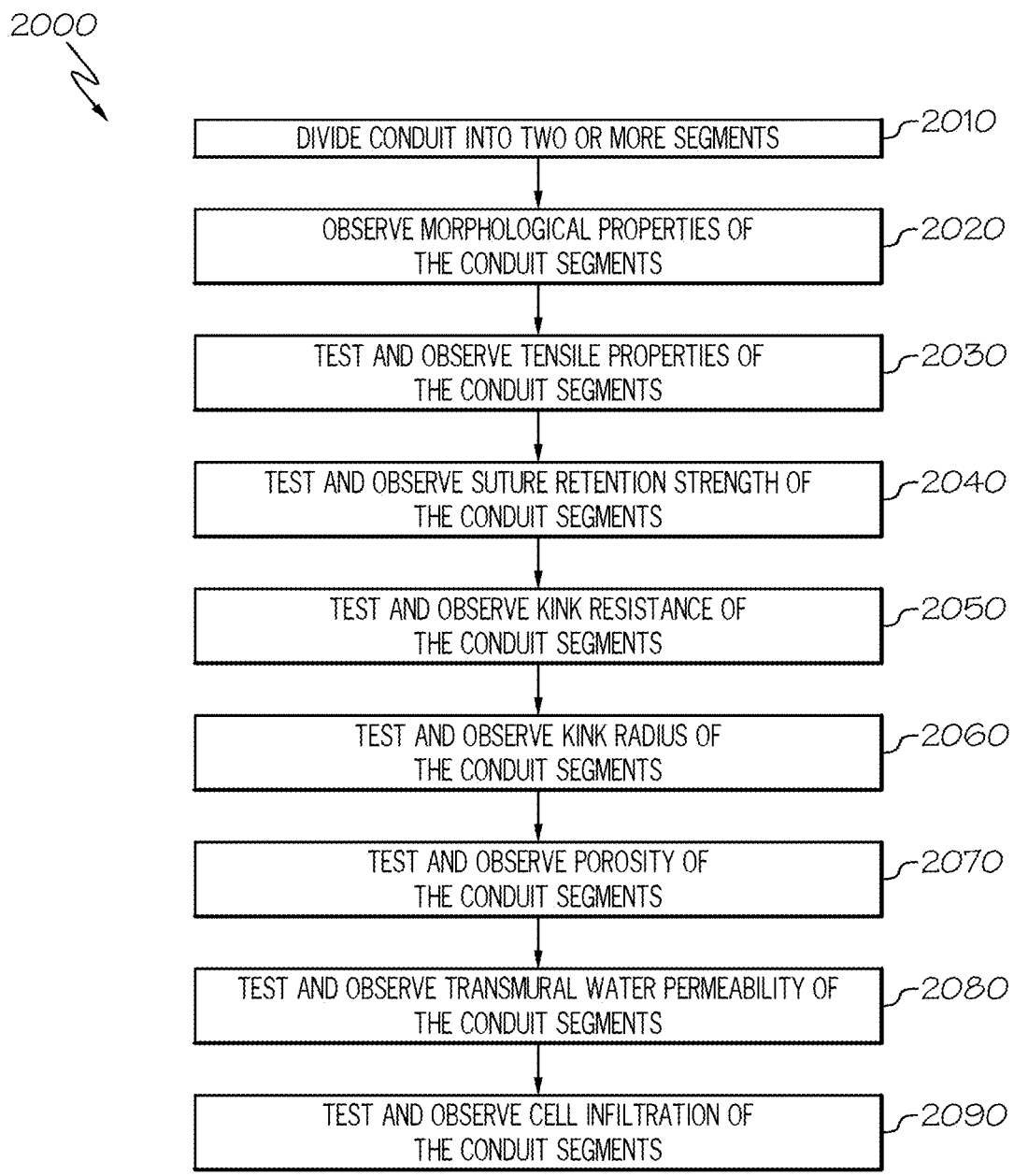
FIG. 6 illustrates a method for interrogating a conduit comprising an extracellular matrix, consistent with the present inventive concepts.

Referring now to FIG. 6, a method for interrogating a graft, conduit, graft-conduit combination comprising an extracellular matrix is illustrated, consistent with the present inventive concepts. Method 2000 can be configured to interrogate a conduit (e.g. implant 20) produced in method 1000 described herein in reference to FIG. 5. Method 2000 can be configured to assess at least one of the uniaxial tensile properties in the circumferential and/or longitudinal direction, suture retention strength, kink radius, or kink resistance of implant 20.

In some embodiments, method 2000 is further configured to assess the permeability of implant 20 using a transmural infusion of saline via a syringe pump and a pressure transducer. In some embodiments, method 2000 is further configured to assess the porosity and/or pore size of implant 20 via an analysis of scanning electron microscope (SEM) images and/or mercury porosimetry.

In some embodiments, method 2000 is further configured to assess cell infiltration capabilities of implant 20 via cell seeding, brief culture, and/or assessment of cellular distribution into implant 20.

In STEP 2010, implant 20 is cut, or otherwise divided, into two or more serial segments of equal or different lengths along the longitudinal direction of implant 20. In some embodiments, implant 20 is divided into proximal, medial, and distal segments. Each segment can comprise a length of between 1 mm and 150 mm.

In STEP 2020, the morphological properties of one or more segments of implant 20 are observed. The morphological properties can be observed via scanning electron microscopy and/or micro-CT scan.

In STEP 2030, the circumferential and/or longitudinal tensile properties of one or more segments of implant 20 are tested and observed.

To interrogate the circumferential uniaxial tensile properties of implant 20, two parallel bars are inserted through the lumen of each segment and the parallel bars are connected to tensile tester device 612. The segments can be immersed in 1×PBS at a temperature of approximately 37° C.

To interrogate the longitudinal uniaxial tensile properties of implant 20, a longitudinal slit is performed to open the tubular implant 20 into a rectangular shape, such that the long sides align with the longitudinal direction of implant 20 and the short sides with the circumferential direction of implant 20. The two short sides of the rectangular shape can be secured by clamps and connected to tensile tester device 612. The segments can be immersed in 1×PBS at a temperature of approximately 37° C.

Tensile tester device 612 can be configured to pull the segments at a constant crosshead speed of approximately 50 mm/min until a material failure is observed. The elastic tension modulus at 5% strain can be used to define the tension recorded while passing through the 5% strain level (tension/strain at 5% strain). The ultimate circumferential tensile strength is the maximum recorded tension during the test.

In STEP 2040, the suture retention strength of one or more segments of implant 20 are tested and observed. To interrogate the suture retention strength of implant 20, a 4-0 to 10-0 nylon monofilament suture is fastened approximately 2 mm from a free edge of each segment. The suture can be knotted into a loop comprising a diameter of approximately 3 cm. The segments can be immersed in a 1×PBS at a temperature of approximately 37° C. The suture is pulled uniaxially until failure along the longitudinal direction of each segment is observed. The suture retention strength can be defined as the peak load recorded. In some embodiments, implant 20 comprises a suture retention strength no less than 1.7N.

In STEP 2050, the kink resistance of one or more segments of implant 20 are tested and observed. To interrogate the kink resistance of implant 20 to a fixed radius of approximately 20 mm, each segment is wrapped around a plastic cylinder comprising a diameter of approximately 40 mm. The segments can be immersed in 1×PBS at a temperature of approximately 37° C.

In STEP 2060, the kink radius of one or more segments of implant 20 are tested and observed. To interrogate the kink radius of implant 20, each segment is wrapped around cylindrical forms with progressively smaller diameters to establish the smallest diameter/radius allowing less than 50% of luminal area to collapse due to kinking.

In STEP 2070, the porosity of one or more segments of implant 20 are tested and observed. The porosity can be observed via mercury porosimetry.

In STEP 2080, the transmural water permeability of one or more segments of implant 20 are tested and observed. To interrogate the transmural water permeability of implant 20, each segment is connected to a fluid infusion apparatus and the resultant pressure is measured via a transducer.

In STEP 2090, the cell infiltration of one or more segments of implant 20 are tested and observed. The segments can be seeded with cells and the resulting cell distribution, proliferation, and matrix deposition can be observed over time.

It is appreciated STEPs 2020-2090 can be performed in any order, and as such, method 2000 is not limited to the sequence as described herein. For example, STEP 2030 can be performed prior to STEPs 2020 and 2090. As another example, STEP 2090 can be performed prior to STEPs 2020 and 2030.

It is further appreciated STEPs 2020-2090 are optional, and as such, method 2000 can comprise a subset of the sequence as described herein. For example, STEPs 2020 and 2030 are performed whereas STEP 2090 is not. As another example, STEPs 2020 and 2090 are performed whereas STEP 2030 is not. As another example, STEP 2030 is performed whereas STEPs 2020 and 2090 are not.

As described herein in reference to FIG. 6, Method 2000 can be configured to interrogate at least a portion of implant 20 described herein.

Figure 7:
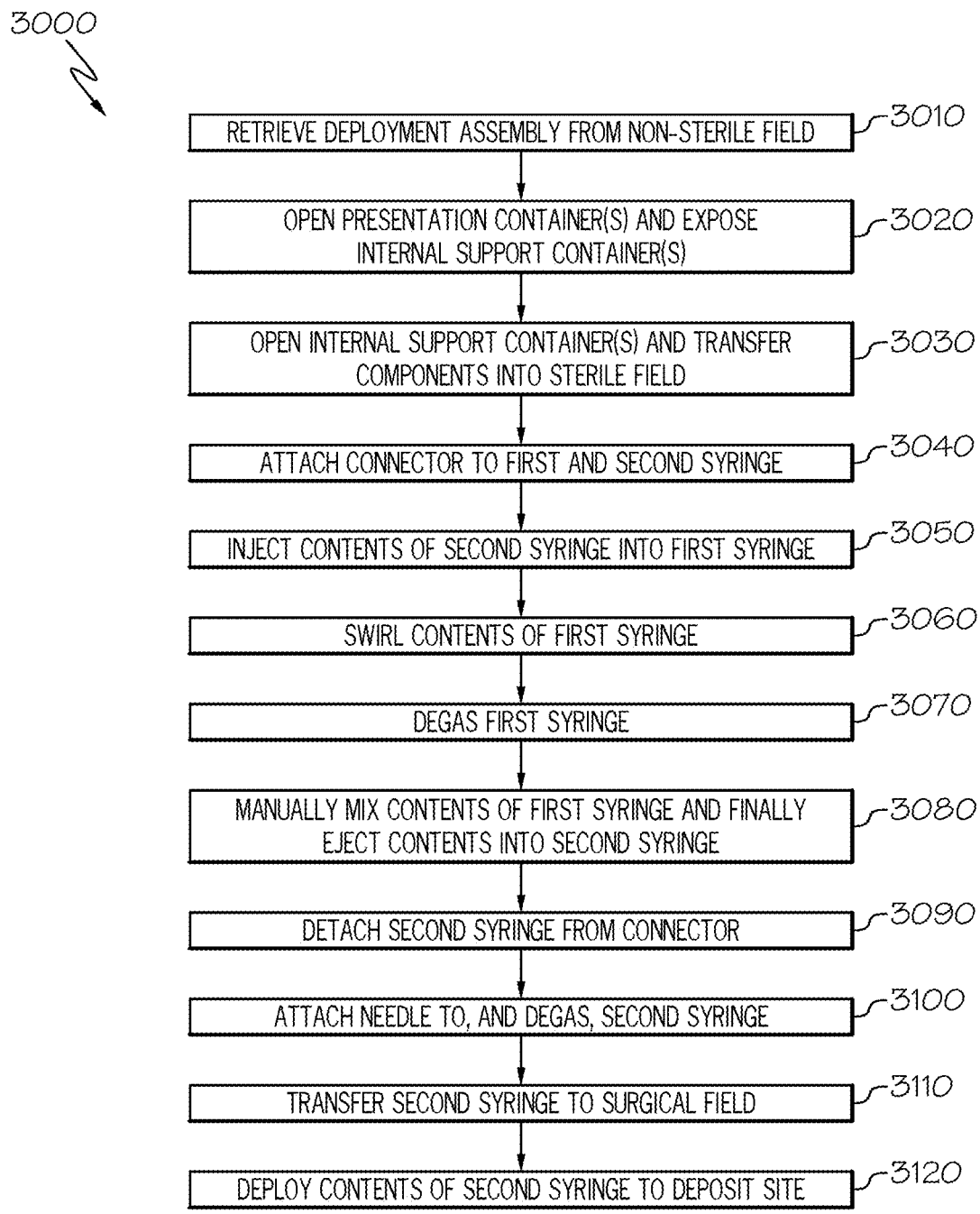
FIG. 7 illustrates a method for preparing and/or deploying a device comprising an extracellular matrix, consistent with the present inventive concepts.
Figure 8:
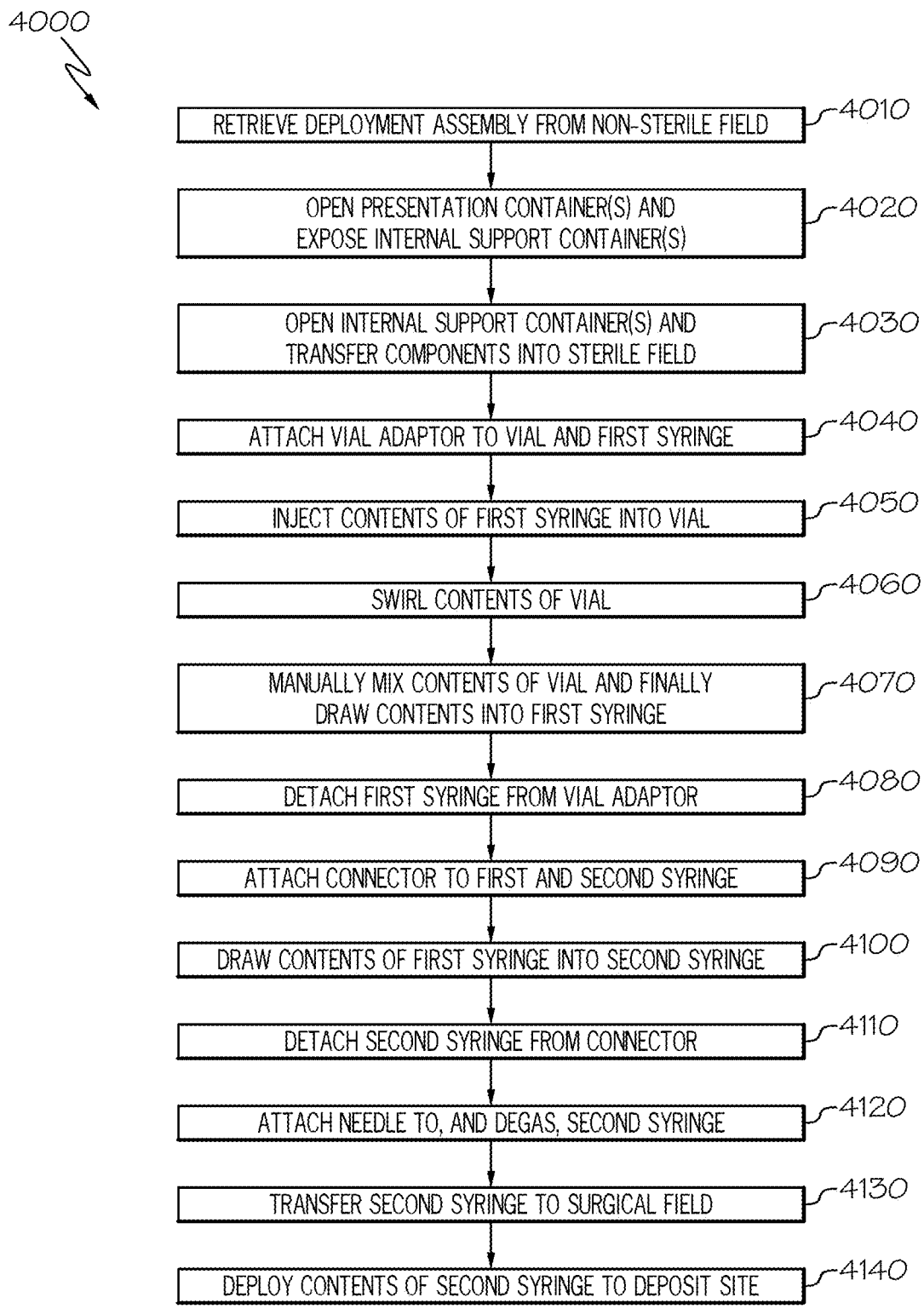
FIG. 8 illustrates a method for preparing and/or deploying a device comprising an extracellular matrix, consistent with the present inventive concepts
Figure 9:
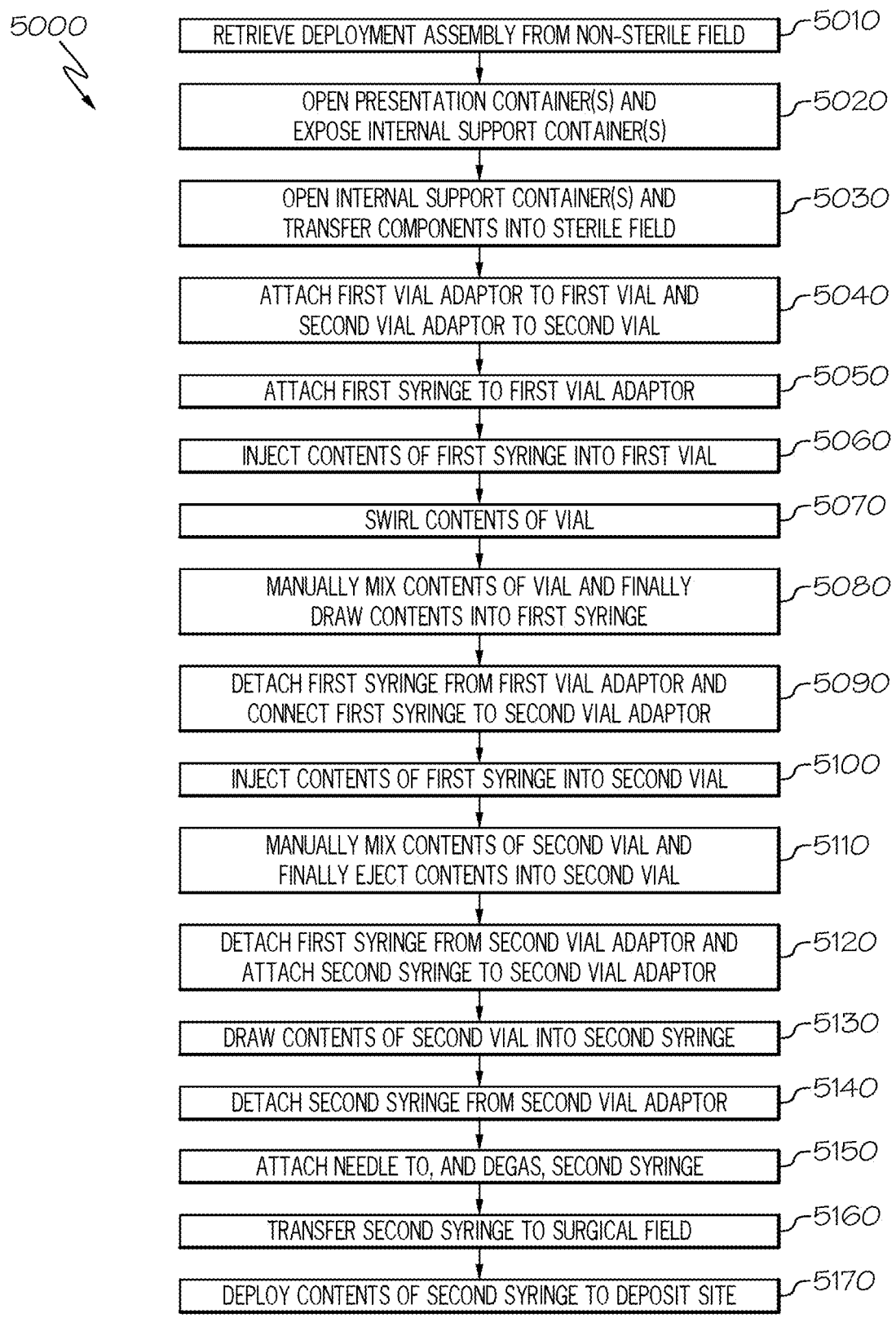
FIG. 9 illustrates a method for preparing and/or deploying a device comprising an extracellular matrix, consistent with the present inventive concepts

Referring now to FIGS. 7-9, methods for preparing and/or deploying a device comprising an extracellular matrix is illustrated, consistent with the present inventive concepts. Methods 3000, 4000, and 5000 can be configured to prepare and/or deploy device 100 comprising ECM 120 described herein, such as deployment assembly 200 comprising various components configured to prepare and/or deploy device 100 comprising ECM 120. Deployment assembly 200 can comprise the various components as described herein in reference to FIGS. 3A-P. Device 100 comprising ECM 120 can be deployed proximate a deposit site described herein in reference to FIG. 1.

Prior to, during, and/or after the deployment of device 100, one or more sterile operators (e.g. physician, surgeon, etc.) can visualize and/or access the deposit site via imaging device 30. In some embodiments, the sterile operator utilizes imaging device 30 to perform an image guided procedure to deploy device 100, such as when imaging device 30 comprises an ultrasound. Image guided deployment of device 100 can eliminate the need for an open surgical site to access the deposit site. In some embodiments, the sterile operator utilizes imaging device 30 to perform a minimally invasive procedure to deploy device 100, such as when imaging device 30 comprises an endoscope or robotic arm.

Prior to, during, and/or after the deployment of device 100, one or more sterile operators (e.g. physician, surgeon, etc.) can modify one, two, or more properties of the deposit site and/or tissue proximate the deposit site. In some embodiments, the sterile operator performs a clinical procedure, such as to repair (e.g. surgically repairs) one or more defects of the deposit site. In some embodiments, the sterile operator modifies tissue at the deposit site, such as to remove excess and/or injured tissue (e.g. remove neuromas from nerve tissue). In some embodiments, the sterile operator modifies tissue at the deposit site, such as to add and/or move tissue (e.g. via nerve graft or nerve transfer). In some embodiments, the sterile operator modifies (e.g. increase, decrease) the hydration level of the deposit site. In some embodiments, the sterile operator applies a thermal and/or light treatment to the deposit site. In some embodiments, the sterile operator applies a chemical treatment to the deposit site. In some embodiments, the sterile operator mechanically restrains tissue at the deposit site, such as to hold the tissue in a desire position, expose an area of the tissue, and/or otherwise manipulate the tissue to aid in the placement of device 100. In some embodiments, the sterile operator applies a mechanical treatment to the deposit site. In some embodiments, the sterile operator modifies one, two, or more environmental properties of the deposit site, such as pH, temperature, hydration level, tissue permeability, presence of blood, amount of protein, and level of drugs.

Deployment of device 100 prior to a modification of the deposit site can minimize manipulation of the deposit site and/or tissue following a clinical procedure. For example, device 100 can be deployed into either side of a cut nerve (e.g. nerve full or partial transection) prior to the removal of excess and/or injured tissue, and/or prior to the surgical repair of the cut nerve.

Deployment of device 100 before and/or after a modification of the deposit site can promote healing (e.g. cell growth) at the deposit site following a clinical procedure. For example, device 100 can be deployed in a space between two surgically connected nerve stumps, such as to promote cell growth between the two nerve stumps.

Deployment of device 100 without a modification of the deposit site can promote healing (e.g. cell growth) at the deposit site. For example, device 100 can be deployed into and/or onto an injured nerve that has maintained continuity and/or at least partial functionality following the injury (e.g. nerve crush).

As described herein in reference to FIGS. 7-9, Methods 3000, 4000, and/or 5000 can be configured to prepare and/or deploy at least a portion of device 100 described herein.

Referring now to FIG. 7, a method for preparing and/or deploying a device comprising an extracellular matrix is illustrated, consistent with the present inventive concepts. Method 3000 utilizes a deployment assembly 200 comprising a syringe 220 with ECM 120 therein, such as is shown in FIGS. 3F; 3G; 3O; and 3P.

For non-limiting illustrative purposes, Method 3000 will be described in reference to FIG. 3P. Deployment assembly 200 comprises two support containers 205a,b, two presentation containers 207a,b, two syringes 220a,b, one needle 240, and one connector 260. Container 205a comprises syringe 220a comprising ECM 120. Container 205b can comprise syringe 220b, needle 240, and connector 260. Container 205b further includes a separate plunger 212 configured to be attached to syringe 220a. Syringe 220b comprises a co-solution of neutralizing element 140 and reconstituting element 160. Connector 260 comprises a three-way stopcock valve with a filter attached to the central port. Containers 207a,b are constructed and arranged to comprise containers 205a,b, respectively.

In STEP 3010, deployment assembly 200 (e.g. containers 207a,b) are retrieved from a non-sterile field (e.g. storage) by a first, non-sterile operator (e.g. circulating nurse, etc.) and is transported to the room within which the clinical procedure is to be performed (e.g. treatment room, operating room).

In STEP 3020, the first operator opens containers 207a,b to expose containers 205a,b.

In STEP 3030, the first operator opens containers 205a,b in proximity to the sterile field where a second sterile operator (e.g. scrub nurse, surgeon, etc.) assists with the transfer of all internal components (e.g. syringes 220a,b, needle 240, plunger stem 212, and connector 260) to the sterile field using aseptic techniques.

In STEP 3040, the second operator attaches plunger 212 to syringe 220a, uncaps syringe 220a, uncaps syringe 220b, and attaches both syringes 220a,b with connector 260. Syringes 220a,b are now in fluid communication via connector 260.

In STEP 3050, the second operator injects reconstituting element 160 and neutralizing element 140 from syringe 220b into syringe 220a (e.g. through connector 260), such that ECM 120 and reconstituting element 160 and neutralizing element 140 interact within syringe 220a.

In STEP 3060, with syringe 220a still attached to syringe 220b via connector 260, the second operator swirls the contents (e.g. ECM 120 and reconstituting element 160 and neutralizing element 140) of syringe 220a for a period of time between 5 and 10 seconds.

In STEP 3070, the second operator degases syringe 220a. In some embodiments, the second operator opens the stopcock valve of connector 260 in a first direction to degas syringe 220a and subsequently returns the stopcock valve in the original position connecting directly syringes 220a,b.

In STEP 3080, the second operator manually mixes the contents (e.g. ECM 120, constituting element 160, and neutralizing element 140) within syringe 220a by withdrawing the contents into syringe 220b (e.g. through connector 260) and subsequently ejecting the contents out of syringe 220b back into syringe 220a repeatedly, such as between 10 and 200 times, such as approximately 100 times. The contents are finally ejected into syringe 220b via connector 260.

In STEP 3090, the second operator detaches syringe 220b from connector 260.

In STEP 3100, the second operator attaches needle 240 to syringe 220b. The second operator further removes the needle guard from needle 240, degases syringe 220b, and primes needle 240.

In STEP 3110, the second operator transfers syringe 220b with exposed needle 240 to a third, sterile operator (e.g. physician, surgeon, etc.) proximate to a surgical field.

In STEP 3120, the third operator deploys, or otherwise delivers, the contents (e.g. ECM 120 and reconstituting element 160 and neutralizing element 140, thereby comprising device 100) within syringe 220b at the deposit site. In some embodiments, the sterile operator deposits one, two, or more droplets of device 100 to the deposit site. In some embodiments, the sterile operator deposits one, two, or more bands of device 100 to the deposit site, such as bands along the length and/or around the circumference of the deposit site.

Figure 10:
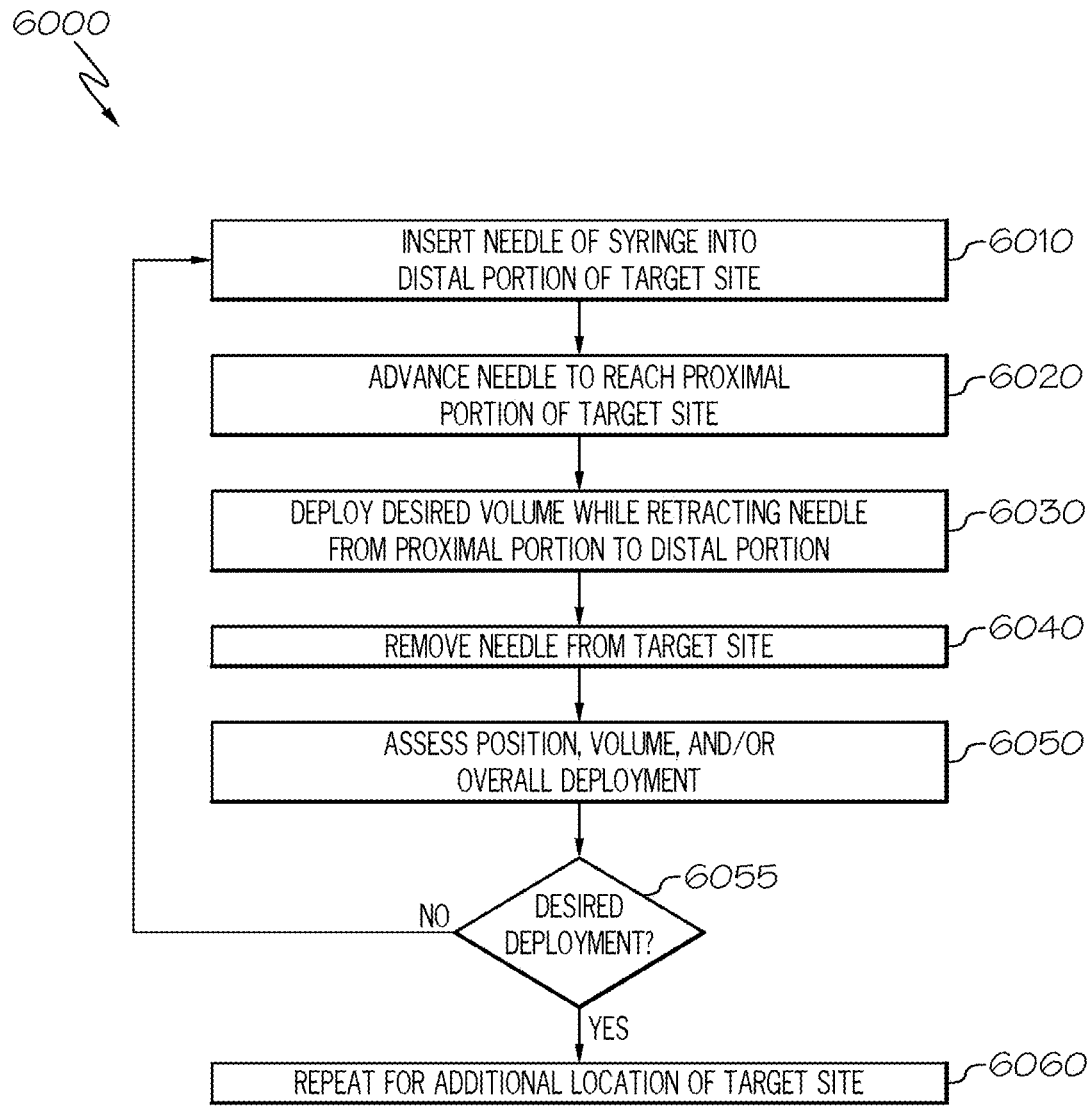
FIG. 10 illustrates a method for deploying a device comprising an extracellular matrix into a nerve, consistent with the present inventive concepts.
Figure 11:
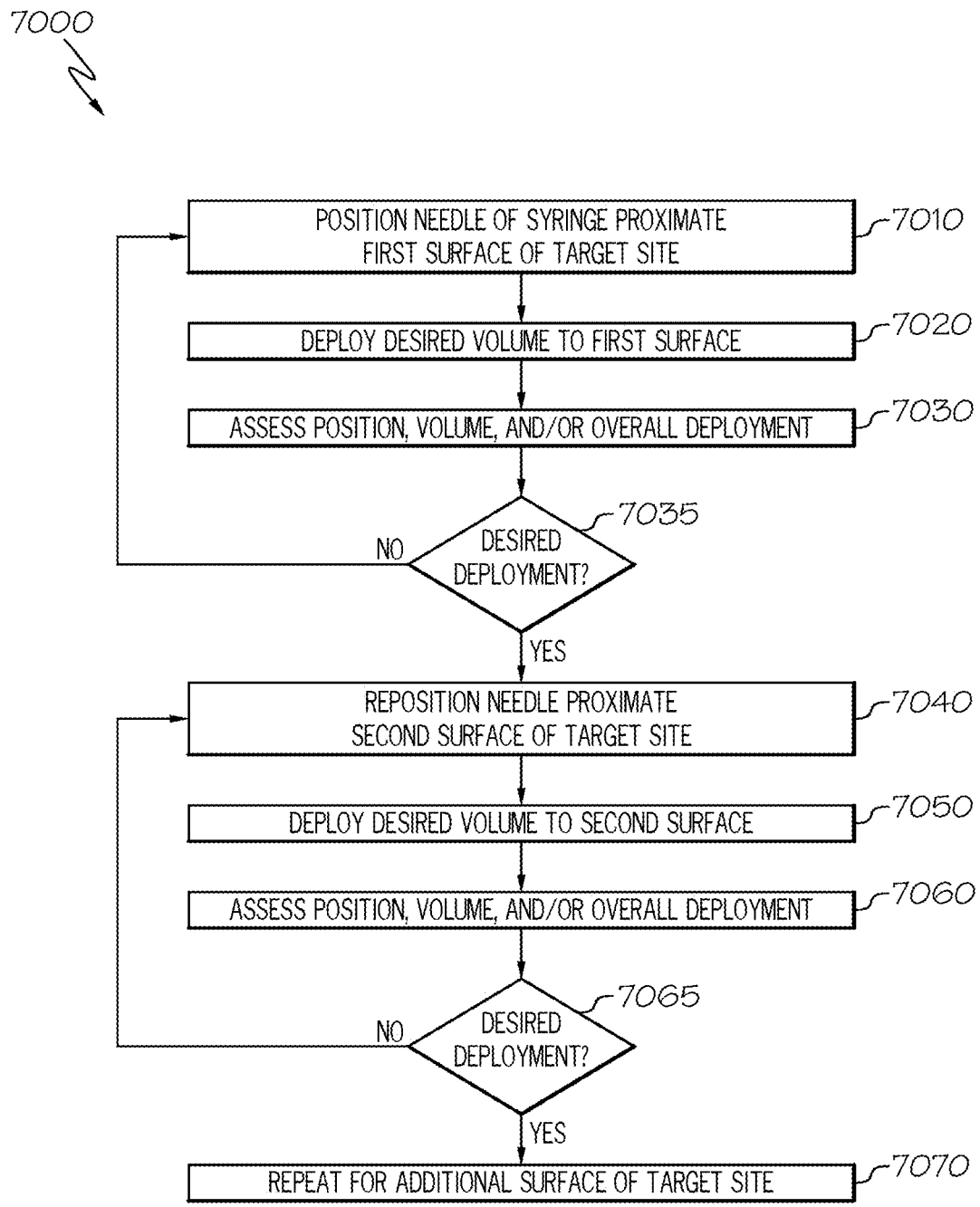
FIG. 11 illustrates a method for deploying a device comprising an extracellular matrix around a nerve, consistent with the present inventive concepts.
Figure 12:
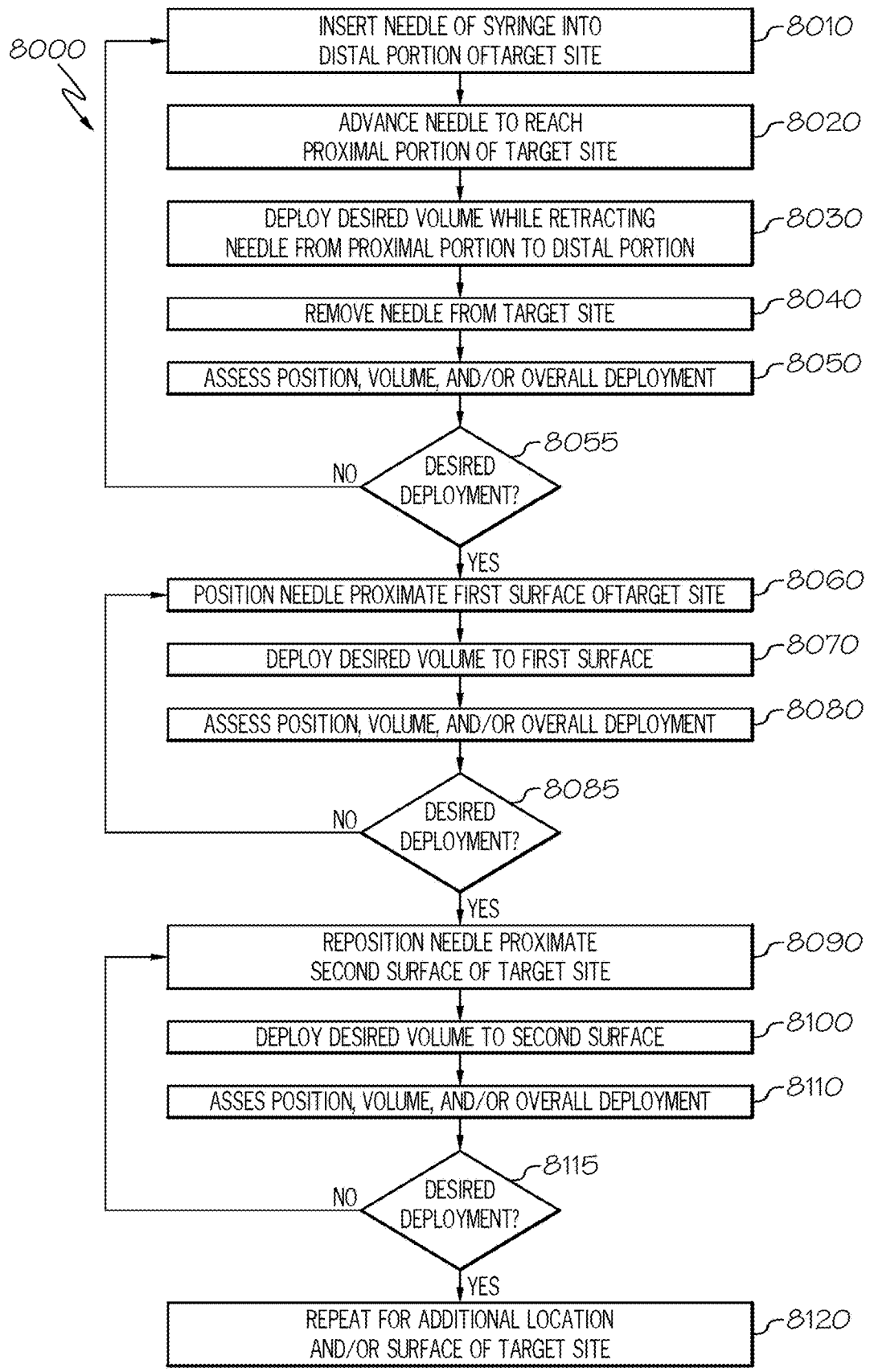
FIG. 12 illustrates a method for deploying a device comprising an extracellular matrix both into and around a nerve, consistent with the present inventive concepts.

Alternatively or additionally, the third operator can deploy device 100 according to methods 6000, 7000, and/or 8000 as described herein in reference to FIGS. 10-12, respectively.

Referring now to FIG. 8, another method for preparing and/or deploying a device comprising an extracellular matrix is illustrated, consistent with the present inventive concepts. Method 4000 utilizes a deployment assembly 200 comprising a container with ECM 120 therein (e.g. vial 210, etc.), such as is shown in FIGS. 3D, 3I, 3J.

For non-limiting illustrative purposes, Method 4000 will be described in reference to FIG. 3D. Deployment assembly 200 comprises three support containers 205a-c, one presentation container 207, one vial 210, two syringes 220a,b, one needle 240, one connector 260, and one vial adaptor 280. Container 205a comprises vial 210 comprising ECM 120. Container 205b comprises syringe 220a comprising co-solution of neutralizing element 140 and reconstituting element 160. Container 205c comprises syringe 220b, needle 240, connector 260, and vial adaptor 280. In some embodiments, syringe 220b, needle 240, connector 260, and vial adaptor 280 are further contained in sub-containers 203a-d. Container 207 is constructed and arranged to comprise containers 205a-c.

In STEP 4010, deployment assembly 200 (e.g. container 207) is retrieved from a non-sterile field (e.g. storage) by a first, non-sterile operator (e.g. circulating nurse, etc.) and is transported to the room within which the clinical procedure is to be performed (e.g. treatment room, operating room).

In STEP 4020, the first operator opens container 207 to expose containers 205a-c.

In STEP 4030, the first operator opens containers 205a-c in proximity to the sterile field where a second sterile operator (e.g. scrub nurse, surgeon, etc.) assists with the transfer of all internal components (e.g. vial 210 comprising ECM 120, syringe 220a comprising reconstituting element 160 and neutralizing element 140, needle 240, connector 260, deployment syringe 220b, and vial adaptor 280) to the sterile field using aseptic techniques.

In STEP 4040, the second operator opens vial 210 by removing the flip off tear off cap and attaches vial 210 to vial adapter 280. Prior to uncapping syringe 220b, the second operator uncaps syringe 220a and attaches it to vial 210 via vial adaptor 280. Vial 210 and syringe 220a are now in fluid communication via vial adapter 280.

In STEP 4050, the second operator injects reconstituting element 160 and neutralizing element 140 from syringe 220a into vial 210, such that ECM 120, reconstituting element 160, and neutralizing element 140 interreact within vial 210.

In STEP 4060, with syringe 220a still attached to vial 210 via adapter 280, the second operator swirls the contents (e.g. ECM 120, reconstituting element 160, and neutralizing element 140) of vial 210 for a period of time between 5 and 10 seconds.

In STEP 4070, the second operator manually mixes the contents (e.g. ECM 120, reconstituting element 160, and neutralizing element 140) within vial 210 by holding the vial 210 upside down and withdrawing the contents into syringe 220*a* (e.g. through vial adaptor 280) and subsequently ejecting the contents out of syringe 220*a* back into vial 210 repeatedly, such as between 10 and 200 times, such as approximately 100 times. The contents are finally drawn into syringe 220*a* via connector 280.

In STEP 4080, the second operator detaches syringe 220*a* from adaptor 280.

In STEP 4090, the second operator uncaps syringe 220*b*, and attaches connector 260 to both syringes 220*a,b*. Syringes 220*a,b* are now in fluid communication via connector 260.

In STEP 4100, the second operator draws the contents of syringe 220*a* into syringe 220*b*.

In STEP 4110, the second operator detaches syringe 220*b* from connector 260.

In STEP 4120, the second operator, attaches needle 240 to syringe 220*b*. The second operator further removes the needle guard from needle 240, degases syringe 220*b*, and primes needle 240.

In STEP 4130, the second operator transfers syringe 220*b* with exposed needle 240 to a third, sterile operator (e.g. physician, surgeon, etc.) proximate to a surgical field.

In STEP 4140, the third operator deploys, or otherwise delivers, the contents (e.g. ECM 120, reconstituting element 160, and neutralizing element 140, thereby comprising device 100) within syringe 220*b* at the deposit site. In some embodiments, the sterile operator deposits one, two, or more droplets of device 100 to the deposit site. In some embodiments, the sterile operator deposits one, two, or more bands of device 100 to the deposit site, such as bands along the length and/or around the circumference of the deposit site.

Alternatively or additionally, the third operator can deploy device 100 according to methods 6000, 7000, and/or 8000 as described herein in reference to FIGS. 10-12-, respectively.

Referring now to FIG. 9, another method for preparing and/or deploying a device comprising an extracellular matrix is illustrated, consistent with the present inventive concepts. Method 5000 utilizes a deployment assembly 200 comprising a container with ECM 120 therein (e.g., vial 210), such as is shown in FIGS. 3A-C; 3E-H; and 3K-N.

For non-limiting illustrative purposes, method 5000 will be described in reference to FIG. 3L. Deployment assembly 200 comprises one support container 205, one presentation container 207, two vials 210*a,b*, two syringes 220*a,b*, one needle 240, and two vial adaptors 280*a,b*. Container 205 comprises vials 210*a,b*, syringes 220*a,b*, needle 240, and vial adaptors 280*a,b*. Vial 210*a* comprises ECM 120 and vial 210*b* comprises neutralizing element 140. Syringe 220*a* comprises reconstituting element 160. In some embodiments, each vial 210*a,b*, each syringe 220*a,b*, needle 240, and each vial adaptor 280*a,b* is further contained in sub-containers 203*a-g*. Container 207 is constructed and arranged to comprise container 205.

In STEP 5010, deployment assembly 200 (e.g. container 207) is retrieved from a non-sterile field (e.g. storage) by a first, non-sterile operator (e.g. circulating nurse, etc.) and is transported to the room within which the clinical procedure is to be performed (e.g. treatment room, operating room).

In STEP 5020, the first operator opens containers 207 to expose container 205.

In STEP 5030, the first operator opens container 205 in proximity to the sterile field where a second sterile operator (e.g. scrub nurse, surgeon, etc.) assists with the transfer of all internal components (e.g. vials 210*a,b*, syringes 220*a,b*, vial adapters 280*a,b*, and needle 240) to the sterile field using aseptic techniques.

In STEP 5040, the second operator opens vials 210*a,b* by removing their flip off tear off cap, and connects vial 210*a* to vial adapter 280*a* and vial 210*b* to vial adapter 280*b*.

In STEP 5050, the second operator uncaps syringe 220*a* comprising reconstituting element 160 and attaches syringe 220*a* to vial 210*a* via vial adapter 280*a*. Vial 210*a* and syringe 220*a* are now in fluid communication via adapter 280*a*.

In STEP 5060, the second operator injects reconstituting element 160 from syringe 220*a* into vial 210*a*, such that ECM 120 and reconstituting element 160 interreact within vial 210*a*.

In STEP 5070, with syringe 220*a* still attached to vial 210*a* via adapter 280*a*, the second operator swirls the contents (e.g. ECM 120 and reconstituting element 160) of vial 210*a* for a period of time of between 5 and 10 seconds.

In STEP 5080, the second operator manually mixes the contents (e.g. ECM 120 and reconstituting element 160) within vial 210*a* by holding the vial 210*a* upside down and withdrawing the contents into syringe 220*a* (e.g. through adaptor 280*a*) and subsequently ejecting the contents out of syringe 220*a* back into vial 210*a* repeatedly, such as between 10 and 200 times, such as approximately 100 times. The contents are finally drawn into syringe 220*a* via adaptor 280*a*.

In STEP 5090, the second operator detaches syringe 220*a* from vial adaptor 280*a* and connects syringe 220*a* to vial adaptor 280*b*, which is connected to vial 210*b*.

In STEP 5100, the second operator injects the contents of syringe 220*a* (e.g. ECM 120 and reconstituting element 160) into vial 210*b*, such that ECM 120, reconstituting element 160, and neutralizing element 140 interreact within vial 210*b*.

In STEP 5110, the second operator manually mixes the contents (e.g. ECM 120, reconstituting element 160, and neutralizing element 140) within vial 210*b* by holding the vial 210*b* upside down and withdrawing the contents into syringe 220*a* (e.g. through adaptor 280*b*) and subsequently ejecting the contents out of syringe 220*a* back into vial 210*b* repeatedly, such as between 10 and 500 times, such as approximately 20 times. The contents are finally ejected into vial 210*b* via connector 280*b*.

In STEP 5120, the second operator detaches syringe 220*a* from adaptor 280*b* and connects syringe 220*b* to connector 280*b* so that they are in fluid communication.

In STEP 5130, the second operator draws the contents of vial 220*b* into syringe 220*b*.

In STEP 5140, the second operator detaches syringe 220*b* from adaptor 280*b*.

In STEP 5150, the second operator attaches needle 240 to syringe 220*b*. The second operator further removes the needle guard from needle 240, degases syringe 220*b*, and primes needle 240

In STEP 5160, the second operator transfers syringe 220*b* with exposed needle 240 to a third, sterile operator (e.g. physician, surgeon, etc.) proximate to a surgical field.

In STEP 5170, the third operator deploys, or otherwise delivers, the contents (e.g. ECM 120, reconstituting element 160, neutralizing element 140, thereby comprising device 100) within syringe 220*b* at the deposit site. In some embodiments, the sterile operator deposits one, two, or more droplets of device 100 to the deposit site. In some embodiments, the sterile operator deposits one, two, or more bands of device 100 to the deposit site, such as bands along the length and/or around the circumference of the deposit site.

Alternatively or additionally, the third operator can deploy device 100 according to methods 6000, 7000, and/or 8000 as described herein in reference to FIGS. 10-12-, respectively.

Referring now to FIG. 10, a method for deploying a device comprising an extracellular matrix into a nerve is illustrated, consistent with the present inventive concepts. Method 6000 can be configured to deploy device 100 comprising a fluid into a sub-epineural space of one, two, or more nerves at the deposit site. Method 6000 can be initiated within STEPs 3120, 4140, and 5170 as described herein in reference to FIGS. 7-9, respectively.

Device 100 can comprise a sub-epineural deployment volume customized to the nerve diameter. In some embodiments, the nerve comprises a 1 mm diameter (e.g. digital nerve, plantar nerve) and between 10 and 25 μL of device 100 is deployed sub-epineurally. In some embodiments, the nerve comprises a 2 mm diameter (e.g. radial nerve, ulnar nerve, median nerve, plantar nerve) and between 25 and 50 μL of device 100 is deployed sub-epineurally. In some embodiments, the nerve comprises a 3 mm diameter (e.g. radial nerve, ulnar nerve, median nerve, ankle nerve) and between 50 and 100 μL of device 100 is deployed sub-epineurally. In some embodiments, the nerve comprises a 4 mm diameter (e.g. radial nerve, ulnar nerve, median nerve, lower leg nerve) and between 100 and 150 μL of device 100 is deployed sub-epineurally. In some embodiments, the nerve comprises a 5 mm diameter (e.g. lower leg nerve, upper leg nerve) and between 150 and 200 μL of device 100 is deployed sub-epineurally. In some embodiments, the nerve comprises a 6 mm diameter (e.g. lower leg nerve, upper leg nerve) and between 150 and 200 μL of device 100 is deployed sub-epineurally. In some embodiments, the nerve comprises a 7 mm diameter (e.g. upper leg nerve) and between 200 and 250 μL of device 100 is deployed sub-epineurally. In some embodiments, the nerve comprises an 8 mm diameter (e.g. upper leg nerve) and between 250 and 300 μL of device 100 is deployed sub-epineural. In some embodiments, the nerve comprises a 9 mm diameter or larger (e.g. upper leg nerve) and between 250- and 350 μL of device 100 is deployed sub-epineurally. In some embodiments, an excess of device 100 is deployed sub-epineurally and allowed to flow back out, thereby covering the injection and/or surgical site. In some embodiments, excess device 100 is removed prior to closing the injection and/or surgical site. In some embodiments, excess device 100 is allowed to remain while closing the injection and/or surgical site.

As described herein in reference to method 6000, and for non-limiting illustrative purposes, the deposit site comprises one, two, or more injured nerves.

In STEP 6010, a sterile operator (e.g. physician, surgeon, etc.) inserts needle 240 into a distal portion of the deposit site.

In STEP 6020, the sterile operator further advances needle 240 to reach a proximal portion of the deposit site.

In STEP 6030, the sterile operator deploys a volume of device 100 from syringe 220 while retracting needle 240 from the proximal portion to the distal portion, such that device 100 is deployed to extend between the distal portion and proximal portion.

In STEP 6040, the sterile operator removes needle 240 from the deposit site.

In STEP 6050, the sterile operator assesses the position, volume, and/or overall deployment of device 100. In STEP 6055, if a desired deployment of device 100 to the deposit site has been achieved, the sterile operator can proceed to STEP 6060. If a desired deployment of device 100 to the deposit site has not been achieved, the sterile operator can repeat STEPs 6010-6050 until the desired deployment is achieved.

In STEP 6060, the sterile operator can repeat STEPs 6010-6050 to deploy device 100 into one, two, or more additional locations of the deposit site.

As described herein in reference to FIG. 10, Method 6000 can be configured to deploy at least a portion of device 100 described herein.

Referring now to FIG. 11, a method for deploying a device comprising an extracellular matrix around a nerve is illustrated, consistent with the present inventive concepts. Method 7000 can be configured to deploy device 100 comprising a fluid into a peri-epineural space of one, two, or more nerves at the deposit site. Method 7000 can be initiated within STEPs 3120, 4140, and 5170 as described herein in reference to FIGS. 7-9, respectively.

As described herein in reference to method 7000, and for non-limiting illustrative purposes, the deposit site comprises one, two, or more injured nerves.

In STEP 7010, a sterile operator (e.g. physician, surgeon, etc.) positions needle 240 proximate a first surface of the deposit site.

In STEP 7020, the sterile operator deploys a volume of device 100 from syringe 220, such that device 100 engages the first surface.

In STEP 7030, the sterile operator assesses the position, volume, and/or overall deployment of device 100. In STEP 7035, if a desired deployment of device 100 to the deposit site has been achieved, the sterile operator can proceed to STEP 7040. If a desired deployment of device 100 to the first surface has not been achieved, the sterile operator can repeat STEPs 7010-7030 until the desired deployment is achieved.

In STEP 7040, the sterile operator repositions needle 240 proximate a second surface of the deposit site.

In STEP 7050, the sterile operator expels a volume of device 100 from syringe 220, such that device 100 engages the second surface.

In STEP 7060, the sterile operator assesses the position, volume, and/or overall deployment of device 100. In STEP 7065, if a desired deployment of device 100 to the deposit site has been achieved, the sterile operator can proceed to STEP 7070. If a desired deployment of device 100 to the second surface has not been achieved, the sterile operator can repeat STEPs 7040-7060 until the desired deployment is achieved.

In STEP 7070, the sterile operator can repeat STEPs 7010-7060 to deploy device 100 proximate one, two, or more additional surfaces of the deposit site.

As described herein in reference to FIG. 11, Method 7000 can be configured to deploy at least a portion of device 100 described herein.

Referring now to FIG. 12, a method for deploying a device comprising an extracellular matrix both into and around a nerve is illustrated, consistent with the present inventive concepts. Method 8000 can be configured to deploy device 100 comprising a fluid into both a sub-epineural and a peri-epineural space of one, two, or more nerves at the deposit site. In some embodiments, method 8000 comprises a sub-epineural deployment volume as described herein in reference to FIG. 11. Method 8000 can be initiated within STEPs 3120, 4140, and 5170 as described herein in reference to FIGS. 7-9, respectively.

As described herein in reference to method 8000, and for non-limiting illustrative purposes, the deposit site comprises one, two, or more injured nerves.

In STEP 8010, a sterile operator (e.g. physician, surgeon, etc.) inserts needle 240 into a distal portion of the deposit site.

In STEP 8020, the sterile operator further advances needle 240 to reach a proximal portion of the deposit site.

In STEP 8030, the sterile operator expels a volume of device 100 from syringe 220 while retracting needle 240 from the proximal portion to the distal portion, such that device 100 is deployed to extend between the distal portion and proximal portion.

In STEP 8040, the sterile operator removes needle 240 from the deposit site.

In STEP 8050, the sterile operator assesses the position, volume, and/or overall deployment of device 100. In STEP 8055, if a desired deployment of device 100 to the deposit site has been achieved, the sterile operator can proceed to STEP 8060. If a desired deployment of device 100 to the deposit site has not been achieved, the sterile operator can repeat STEPs 8010-8050 until the desired deployment is achieved.

In STEP 8060, a sterile operator (e.g. physician, surgeon, etc.) positions needle 240 proximate a first surface of the deposit site.

In STEP 8070, the sterile operator expels a volume of device 100 from syringe 220, such that device 100 engages the first surface.

In STEP 8080, the sterile operator assesses the position, volume, and/or overall deployment of device 100. In STEP 8085, if a desired deployment of device 100 to the first surface has been achieved, the sterile operator can proceed to STEP 8090. If a desired deployment of device 100 to the first surface has not been achieved, the sterile operator can repeat STEPs 8060-8080 until the desired deployment is achieved.

In STEP 8090, the sterile operator repositions needle 240 proximate a second surface of the deposit site.

In STEP 8100, the sterile operator expels a volume of device 100 from syringe 220, such that device 100 engages the second surface.

In STEP 8110, the sterile operator assesses the position, volume, and/or overall deployment of device 100. In STEP 8115, if a desired deployment of device 100 to the deposit site has been achieved, the sterile operator can proceed to STEP 8120. If a desired deployment of device 100 to the second surface has not been achieved, the sterile operator can repeat STEPs 8090-8110 until the desired deployment is achieved.

In STEP 8120, the sterile operator can repeat STEPs 8010-8110 to deploy device 100 into one, two, or more additional locations and/or proximate one, two, or more additional surfaces of the deposit site.

As described herein in reference to FIG. 12, Method 8000 can be configured to deploy at least a portion of device 100 described herein.

Figure 36:
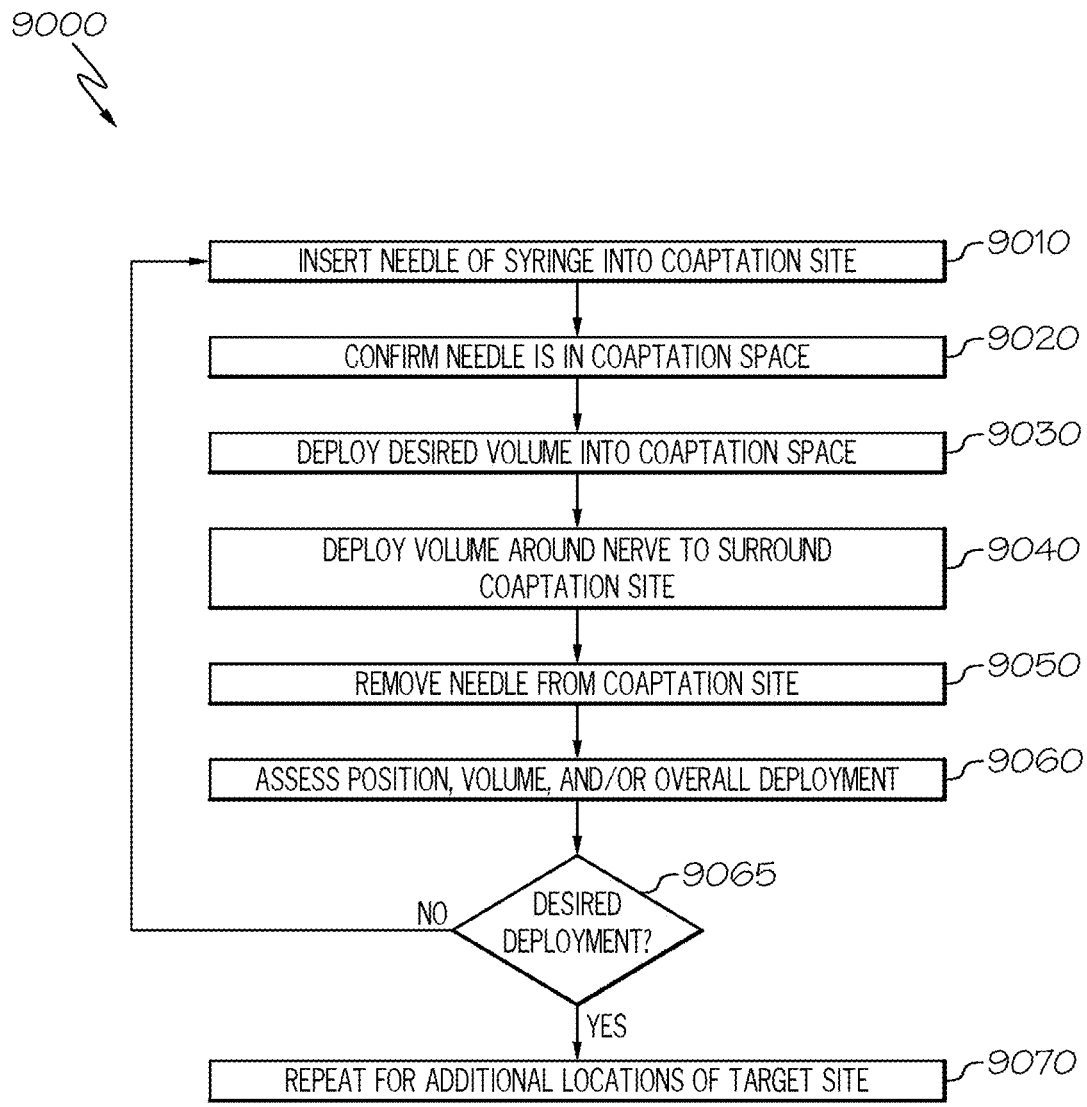
FIG. 36 illustrates a method for deploying a device comprising an extracellular matrix at and around a nerve coaptation site, consistent with the present inventive concepts.

Referring now to FIG. 36, a method for deploying a device comprising an extracellular matrix at and around a nerve coaptation site is illustrated, consistent with the present inventive concepts. Method 9000 can be configured to deploy device 100 comprising a fluid at and around a coaptation site of one, two, or more nerves at the deposit site. Method 9000 can be initiated within STEPs 3120, 4140, and 5170 as described herein in reference to FIGS. 7-9, respectively.

As described herein in reference to method 9000, and for non-limiting illustrative purposes, the deposit site comprises one, two, or more coapted nerves.

In STEP 9010, a sterile operator (e.g. physician, surgeon, etc.) inserts needle 240 into a plane of the coaptation site.

In STEP 9020, the sterile operator checks to ensure needle 240 is positioned within the coaptation space.

In STEP 9030, the sterile operator expels a volume of device 100 from syringe 220 into the coaptation space.

In STEP 9040, the sterile operator expels a volume of device 100 from syringe 220 around the coaptation site, such that device 100 sufficiently surrounds the coaptation site.

In STEP 9050, the sterile operator removes needle 240 from the coaptation site.

In STEP 9060, the sterile operator assesses the position, volume, and/or overall deployment of device 100. In STEP 9065, if a desired deployment of device 100 to the coaptation site has been achieved, the sterile operator can proceed to STEP 9070. If a desired deployment of device 100 to the coaptation site has not been achieved, the sterile operator can repeat STEPs 9010-9065 until the desired deployment is achieved.

In STEP 9070, the sterile operator can repeat STEPs 9010-9050 to deploy device 100 into one, two, or more additional locations of the deposit site.

Figure 13H:
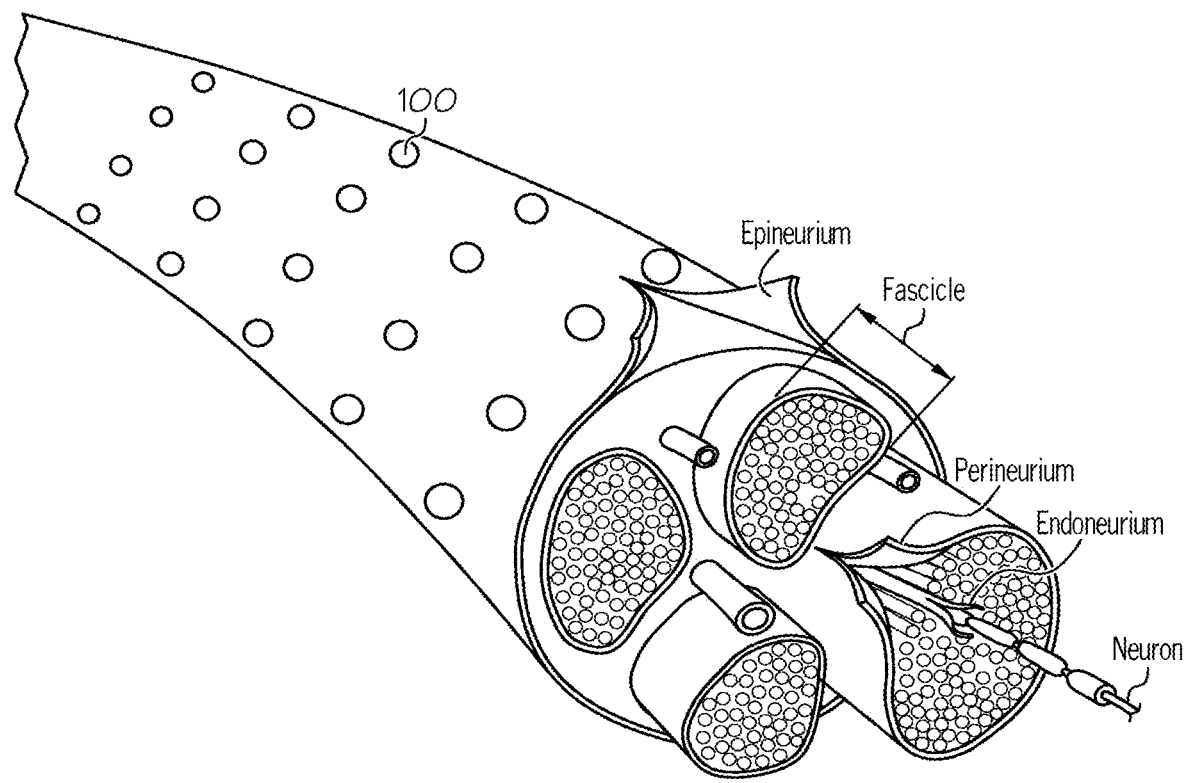
Figure 13I:
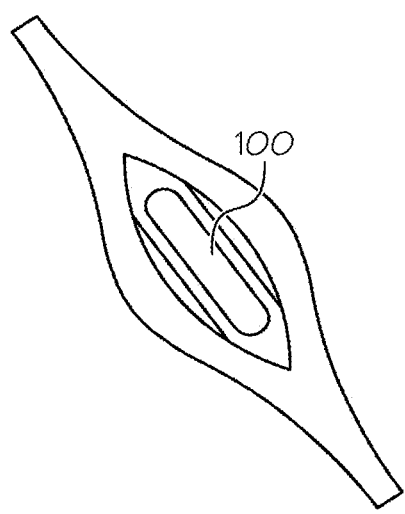
Figure 13J:
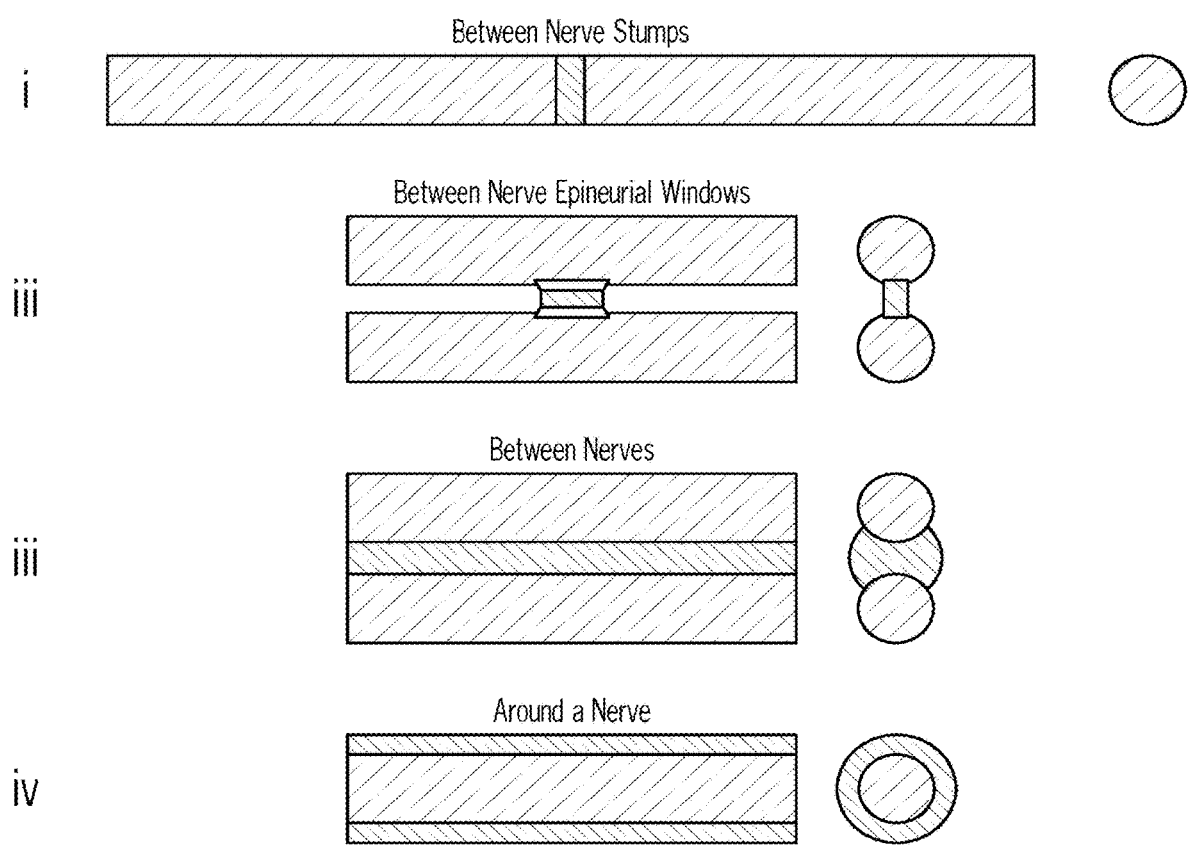

Referring to FIGS. 13A-I, cross-sectional views of a nerve comprising an extracellular matrix are illustrated, consistent with the present inventive concepts. As described herein, at least a portion of the nerve can receive device 100 (e.g. ECM 120). The nerve comprises mesoneurium and epineurium. The nerve further includes a plurality of fascicles comprising perineurium and endoneurium. The fascicles further include a plurality of axons. As shown in FIG. 13A, device 100 can be deployed intra-mesoneurium and/or peri-mesoneurium. As shown in FIG. 13B, device 100 can be deployed intra-epineurium. As shown in FIG. 13C, device 100 can be deployed sub-epineurium. As shown in FIG. 13D, device 100 can be deployed sub-endoneurium. As shown in FIG. 13E, device 100 can be deployed intra-epineurium and sub-endoneurium. As shown in FIG. 13F, device 100 can be deployed sub-epineurium at one, two, or more discrete locations. As shown in FIG. 13G, device 100 can by deployed intra-mesoneurium, peri-mesoneurium, and/or intra-epineurium at one, two, or more discrete locations. As shown in FIG. 13H, device 100 can be deployed intra-mesoneurium, peri-mesoneurium, and/or intra-epineurium at one, two, or more discrete locations along a length and/or circumference of the nerve. As shown in FIG. 13I, device 100 can be deployed along a length of an epineural window. As shown in FIG. 13Ji, device 100 can be deployed between two or more nerve stumps. As shown in FIG. 13Jii, device 100 can be deployed between two or more nerve epineural windows. As shown in FIG. 13Jiii, device 100 can be deployed along a length and between two or more nerves. As shown in FIG. 13Jiv, device 100 can be deployed about at least a portion of the outer surface of a nerve.

Figure 14D:
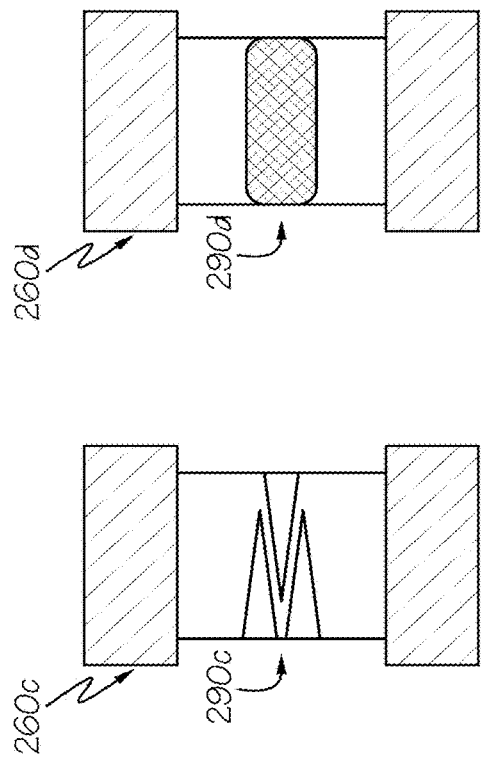
FIGS. 14A-G illustrate various connectors including a homogenizing element, consistent with the present inventive concepts.
Figure 14C:
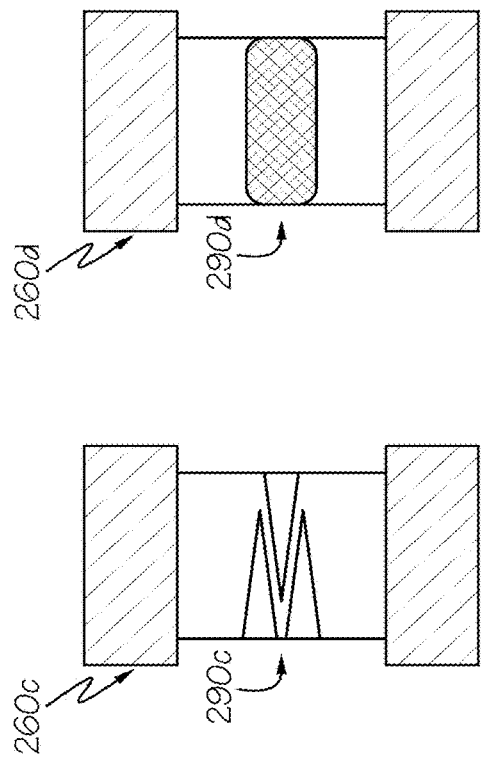
Figure 14B:
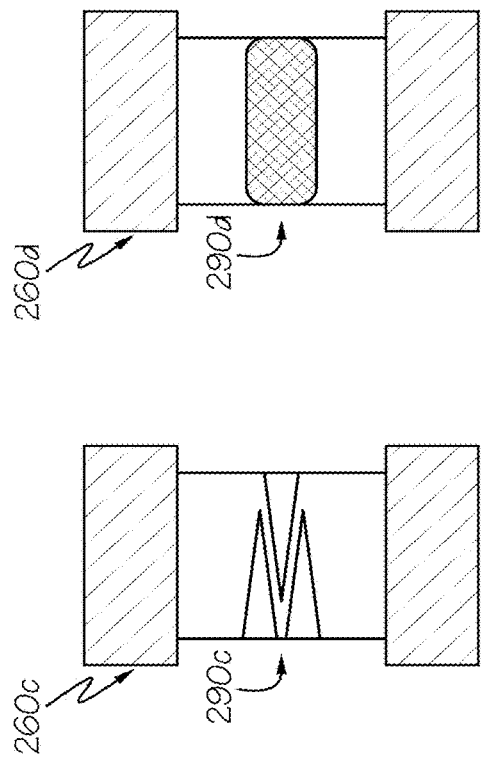
Figure 14A:
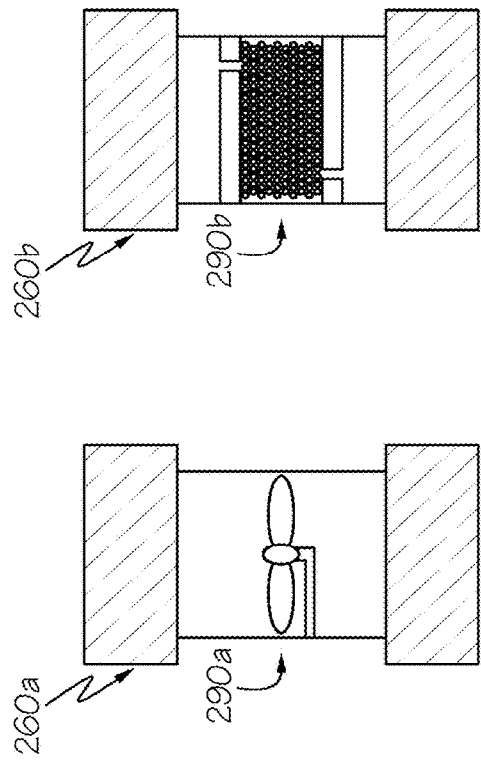
Figure 14G:
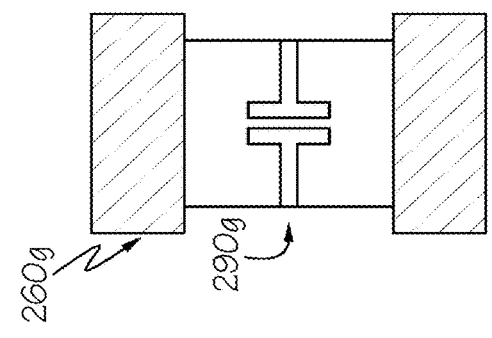
Figure 14F:
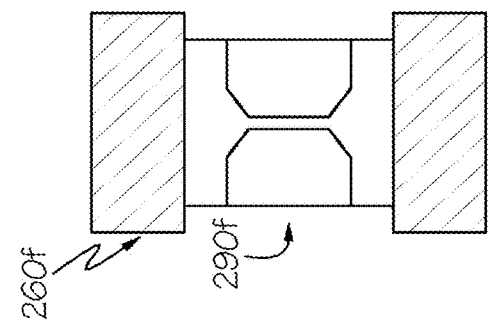
Figure 14E:
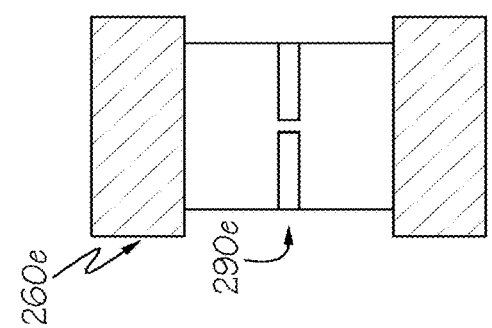

Referring to FIGS. 14A-G, various connectors including a homogenizing element are illustrated, consistent with the present inventive concepts. As described herein, connector 260 can be constructed and arranged to include homogenizer 290. It will be appreciated a single connector 260 can comprise one, two, or more homogenizers 290 constructed and arranged, in series or parallel, with similar and/or dissimilar elements. As shown in FIG. 14A, connector 260*a* comprises a homogenizer 290*a* constructed and arranged as a ducted propeller/turbine element. As shown in FIG. 14B, connector 260*b* comprises a homogenizer 290*b* constructed and arranged as a bead bath. As shown in FIG. 14C, connector 260c comprises a homogenizer 290c constructed and arranged as a tortuous/static element. As shown in FIG. 14D, connector 260d comprises a homogenizer 290d constructed and arranged as a grid/mesh element. As shown in FIG. 14E, connector 260e comprises a homogenizer 290e constructed and arranged as a small orifice. As shown in FIG. 14F, connector 260f comprises a homogenizer 290f constructed and arranged as a funnel with a small channel. As shown in FIG. 14G, connector 260g comprises a homogenizer 290g constructed and arranged as ultrasonic vibration plates.

Figure 15:
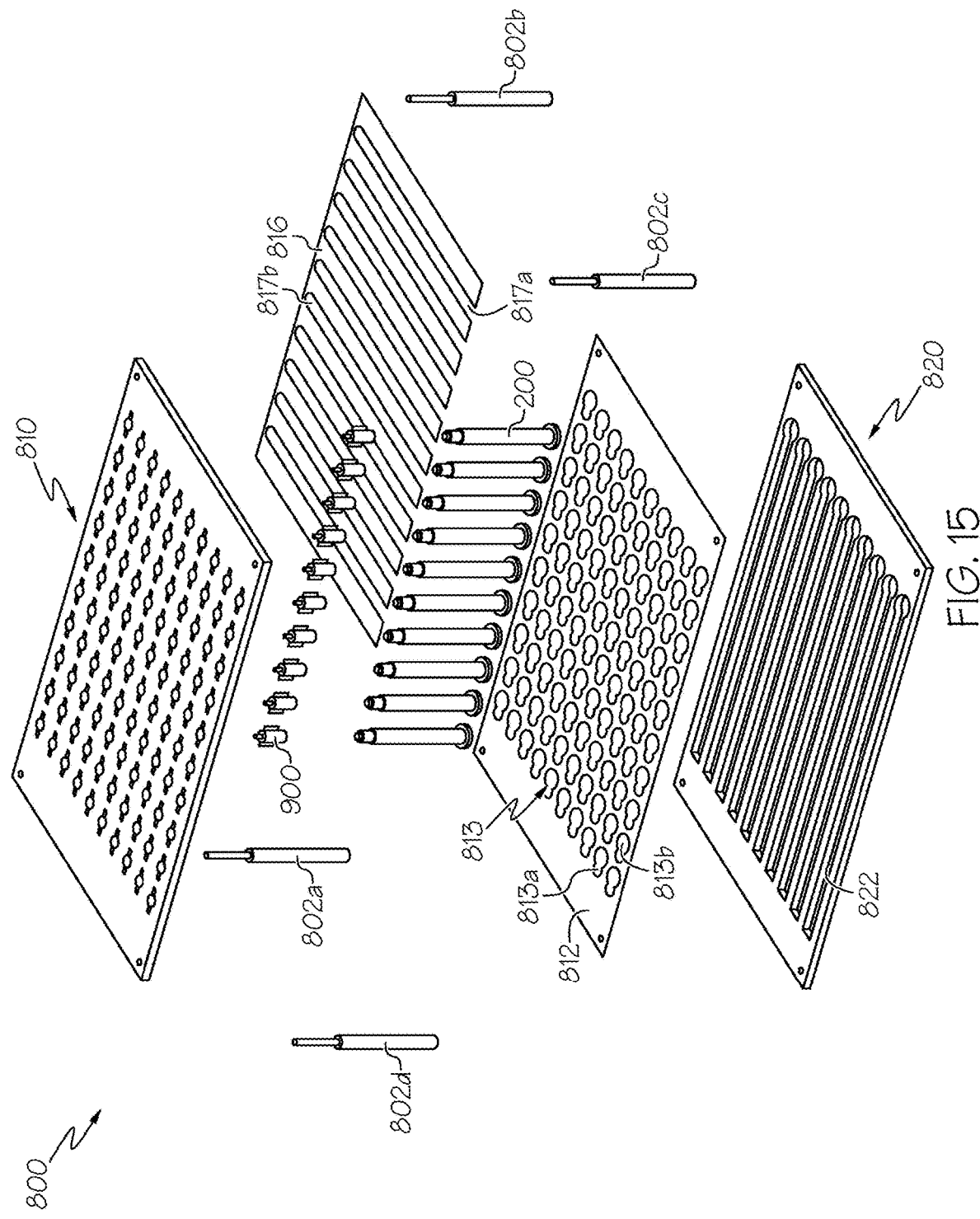

Referring to FIGS. 15, 15A, and 15B, an exploded view of a syringe holding apparatus, a side view of the syringe holding apparatus in an open configuration, and a side view of the syringe holding apparatus in a closed configuration are illustrated, respectively, consistent with the present inventive concepts. Syringe holding apparatus, apparatus 800, can be configured to hold one, two, or more syringes 220 in a vertical orientation during one or more manufacturing and/or transportation processes, such as to hold the syringes during processes like filling/aliquoting, lyophilization, capping and backfilling, packaging, and/or shipments. Apparatus 800 comprises an upper assembly 810 and a lower assembly 820. Apparatus 800 can receive one or more syringes 220 (e.g. one or more syringes 220 can be removably secured within apparatus 800). In some embodiments, syringe 200 is positioned within apparatus 800 such that the syringe distal portion (the hub or tip end of the syringe) is oriented toward upper assembly 810 and the syringe proximal portion (the plunger end of the syringe) is oriented toward lower assembly 820, as shown. Upper assembly 810 can be constructed and arranged to secure at least one cap assembly 900, to at least one corresponding syringe 220 held within apparatus 800. In some embodiments, cap assembly 900 comprises a female luer cap and a portion of syringe 220 (e.g. the tip of syringe 220) comprises a male luer connector. Lower assembly 820 can comprise one or more elongate recesses, slots 822, constructed and arranged to slidingly receive at least a proximal portion of each syringe 220, such as to slidingly receive the barrel flange of syringe 220. In some embodiments, lower assembly 820 comprises ten slots 822 each configured to received ten syringes 220, such that lower assembly 820 is capable of receiving 100 syringes 220. In this embodiments, upper assembly 810 can comprise a corresponding 100 cap assemblies 900 to be secured to the 100 syringes 220.

Upper assembly 810 and lower assembly 820 can be releasably connected via one or more struts, such as struts 802a-d shown. Each strut can include a spring-loaded retractable configuration (spring not shown) configured to enable apparatus 800 to transition from an open configuration to a closed configured (e.g. when upper assembly 810 translates towards lower assembly 820 to transition apparatus 800 from an open configuration to a closed configuration). In the open configuration, as shown in FIG. 15A, upper assembly 810 is configured to suspend and align cap assemblies 900 above syringes 220. In transitioning from the open configuration to the closed configuration, the closed configuration shown in FIG. 15B, upper assembly 810 is configured to descend towards lower assembly 820 to engage syringes 220, such that each cap assembly 900 engages the tip of each syringe 220. Apparatus 800 can transition between the open configuration to the closed configuration via a capping apparatus 950 as described in FIG. 21.

Apparatus 800 can further comprise one, two, or more trays configured to be positioned between upper assembly 810 and lower assembly 820. Apparatus 800 can include one or more trays comprising one or more holes, keyhole tray 812 shown, configured to be positioned proximate a first surface of lower assembly 820. Keyhole tray 812 comprises one or more openings 813 that include a circular portion 813a and a slot portion 813b (e.g. one or more keyhole openings). When positioned proximate a first surface of lower assembly 820, each opening 813 can be arranged to align with a portion of at least one slot 822 below. Opening 813 is constructed and arranged to restrict syringe 220 to a single degree freedom (i.e. translation of syringe 220 between circular portion 813a and slot portion 813b. Each opening 813 can receive a distal portion of syringe 220 via circular portion 813a. Syringe 220 can be further translated into slot portion 813b, such as to removably secure syringe 220 to tray 812. In some embodiments, keyhole tray 812 includes ten rows of ten openings 813, as shown, such that keyhole tray 812 can receive up to 100 syringes 220.

Apparatus 800 can comprise one or more trays comprising one or more elongate openings, comb tray 816 shown, configured to be positioned proximate a first surface of keyhole tray 812. In some embodiments, when apparatus 800 does not include a keyhole tray 812, comb tray 816 is positioned proximate a first surface of lower assembly 820. Comb tray 816 comprises one or more elongate openings, slots 817, that include an open, first end 817a and a closed, second end 817b. Slot 817 can slidingly receive a portion of syringe 220 via first end 817a. Each slot 817 can slidingly receive a portion of at least one syringe 220, such as at least five syringes 220, such as at least ten syringes 220. In some embodiments, comb tray 816 includes ten slots 817, as shown, such that comb tray 816 can receive up to 100 syringes 220.

Apparatus 800 can include a plurality of heat exchange elements 830, as shown in FIG. 15B. Heat exchange elements 830 can be configured to promote heat transfer between syringes 220, the external environment, and the surfaces of apparatus 800. In some embodiments, heat exchange elements 830 comprise stainless steel spheres of homogeneous or heterogeneous diameters of between 0.5 mm and 5 mm. Apparatus 800 can comprise sufficient heat exchange elements 830 to fully surround the fillable portion of each syringe 220 attached to apparatus 800.

Referring to FIGS. 16A-21, various cap assemblies for providing an air-tight seal to syringes are illustrated. As disclosed herein, the cap assemblies can be configured to provide an air-tight seal to (e.g. cap) syringes during a lyophilization process while the syringe is within the lyophilization chamber. An advantage of capping syringes within the lyophilization chamber is that the chamber can be filled with an inert gas (e.g. nitrogen) that enters the syringes, such that the syringes can be backfilled and sealed with the inert gas contained therein. The sealing of an inert gas within the syringes aid the sterilization process by reducing, or otherwise eliminating, the presence of oxygen that comes in contact with the contents of the syringe, and thereby reducing the potential for damage to the syringe contents during irradiation (attributed to the presence of oxygen). Additionally, the sealing of an inert gas within the syringes can improve the shelf-life of the contents of the syringe by reducing the potential of oxidation.

An alternative to capping the syringes within the lyophilization chamber is to insert the opened syringes into a glove box immediately after lyophilization is completed and the open syringe has been removed from the lyophilization chamber. The glove box can then be filled with an inert gas (e.g. nitrogen) and the syringe capping can occur inside the glove box.

Figure 16B:
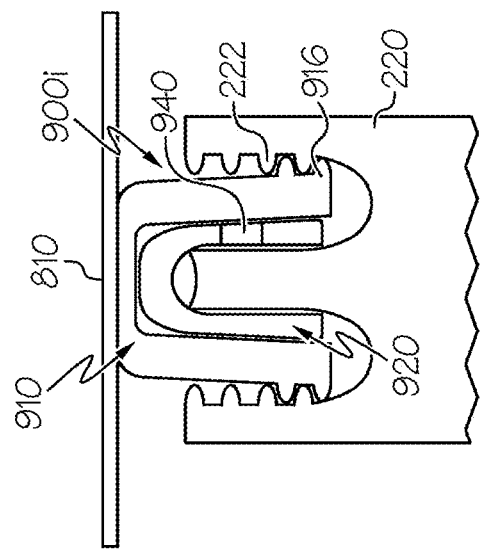
FIGS. 16A and 16B illustrate side views of an embodiment of a cap assembly proximate to and applied to a syringe, respectively, consistent with the present inventive concepts.
Figure 16A:
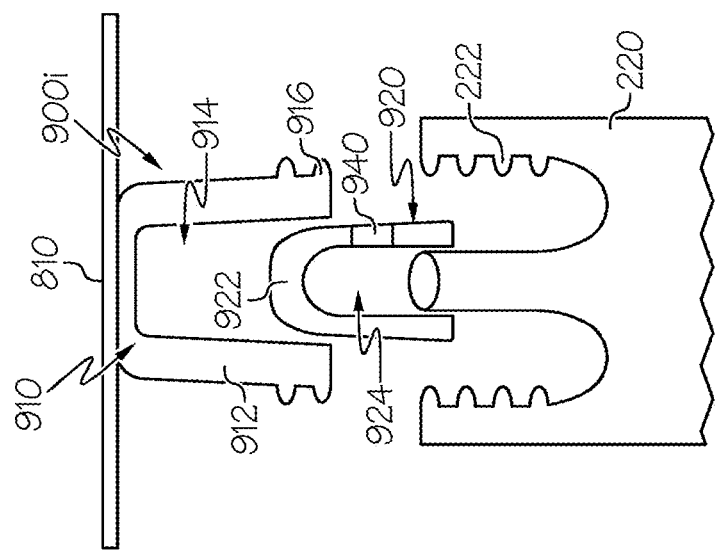

Referring to FIGS. 16A and 16B, side views of an embodiment of a cap assembly proximate to and applied to a syringe are illustrated, respectively, consistent with the present inventive concepts. Cap assembly 900*i*, as described herein, can be constructed and arranged to engage at least a portion of syringe 220, such as the tip of syringe 220. Cap assembly 900*i* can include a first portion 910 configured to receive a second portion 920. First portion 910 can be constructed as integral to (e.g. removably or fixedly attached to) upper assembly 810 of apparatus 800 described herein. First portion 910 can comprise a housing 912 with a cavity 914 therein. First portion 910 can further comprise projections 916 constructed on an outer surface of housing 912. Projections 916 can be configured to engage at least a portion of syringe 220, such as threads 222 of syringe 220 as shown. Second portion 920 can comprise a housing 922 with a cavity 924 therein and one two, or more bores 940 to allow vapor egress from syringe 220 during lyophilization.

During a lyophilization process, cap assembly 900*i* can be configured to transition between an open (illustrated in FIG. 16A) and closed configuration (illustrated in FIG. 16B), such as when first portion 910 slidingly receives (e.g. further receives) second portion 920 and projections 916 of first portion 910 engage threads 222 of syringe 220. In some embodiments, first portion 910 is mechanically lowered onto second portion 920, such as via capping apparatus 950 described herein. In other embodiments, first portion 910 is manually lowered onto second portion 920. In the open configuration, as shown in FIG. 16A, second portion 920 is partially inserted into cavity 914 of first portion 910. In this configuration, elements of the environment external to syringe 220 (e.g. environment surrounding syringe 220) can interact with the contents of the syringe through bore 940. In the closed configuration, as shown in FIG. 16B, first portion 910 further receives second portion 920 occluding bore 940, and projections 916 engage threads 222. In this configuration, elements of the environment external to syringe 220 (e.g. fluid surrounding syringe 220) cannot interact with the contents of the syringe.

Figure 17A:
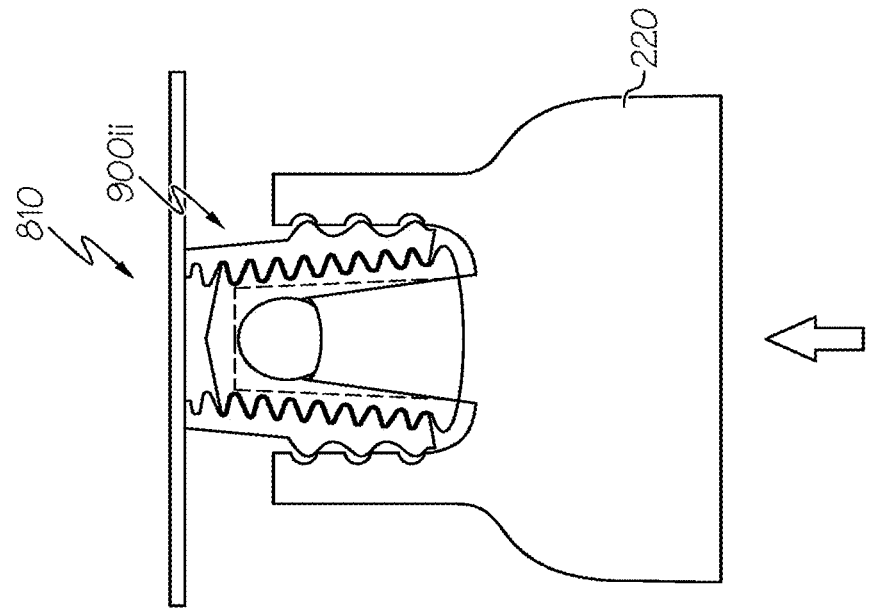
FIGS. 17A and 17B illustrate side views of another embodiment of a cap assembly proximate to and applied to a syringe, respectively, consistent with the present inventive concepts.
Figure 17B:
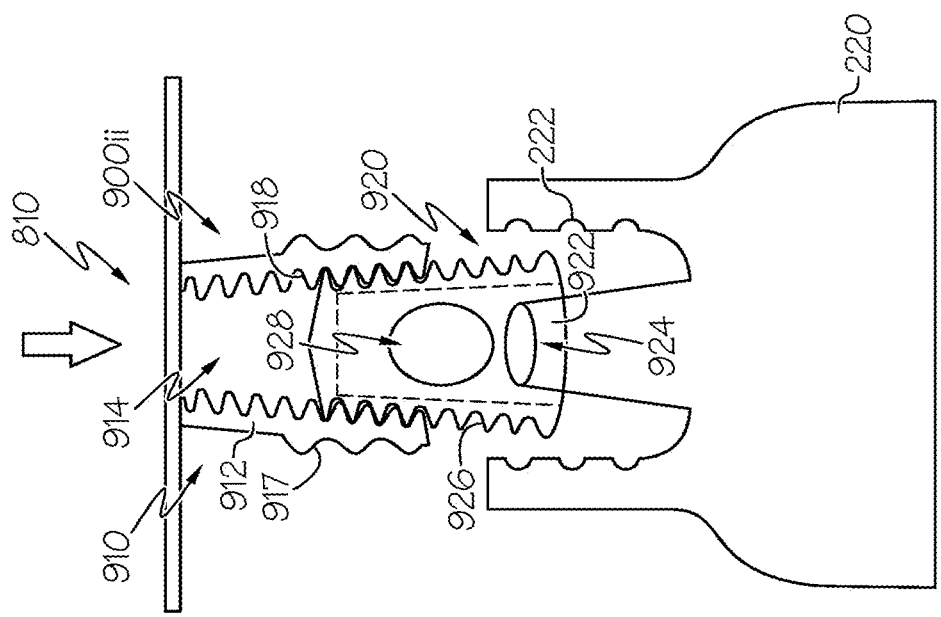

Referring specifically to FIGS. 17A and 17B, side views of another embodiment of a cap assembly proximate to and applied to a syringe are illustrated, respectively, consistent with the present inventive concepts. Cap assembly 900*ii*, as described herein, can be constructed and arranged to engage at least a portion of syringe 220, such as the tip of syringe 220. Cap assembly 900*ii* can include a first portion 910 configured to receive a second portion 920. First portion 910 can be constructed as integral to (e.g. removably or fixedly attached to) upper assembly 810 of apparatus 800 described herein. First portion 910 can comprise a housing 912 with a cavity 914 therein. First portion 910 can further comprise external threads 917 constructed on an outer surface of housing 912 and internal threads 918 constructed on an inner surface of housing 912, as shown. Threads 917 can be configured to engage at least a portion of syringe 220, such as threads 222 of syringe 220 as shown. Second portion 920 can comprise a housing 922 with a cavity 924 therein. Second portion 920 can further comprise external threads 926 constructed on an outer surface of housing 922. Second portion 920 can further comprise at least one fluid exchange element, vent 928 shown, configured to aid in the exchange of elements between syringe 220 and the external environment (e.g. when cap assembly 900*iii* s partially attached to syringe 220 but not yet fully closed). Internal threads 918 of first portion 910 can be configured to rotatably engage external threads 926 of second portion 920, such that first portion 910 covers or otherwise blocks vent 928 of second portion 920.

During a lyophilization process, cap assembly 900*ii* can be configured to transition between an open and closed configuration, such as when first portion 910 rotatably engages second portion 920 and/or syringe 220 to cover vent 928. In some embodiments, first portion 910 is mechanically lowered onto second portion 920 and/or syringe 220, such as via capping apparatus 950 described herein. In other embodiments, first portion 910 is manually lowered onto second portion 920 and/or syringe 220. In the open configuration, as shown in FIG. 17A, second portion 920 is partially inserted into cavity 914 of first portion 910. In this open configuration, elements of the environment external to syringe 220 (e.g. fluid surrounding syringe 220) can interact with the contents of the syringe via vent 928. In the closed configuration, as shown in FIG. 17B, first portion 910 rotatably engages second portion 920 via threads 918,926 to cover vent 928 and first portion 910 rotatable engages syringe 220. In this closed configuration, elements of the environment external to syringe 220 (e.g. fluid surrounding syringe 220) cannot interact with the contents of the syringe.

Figure 18C:
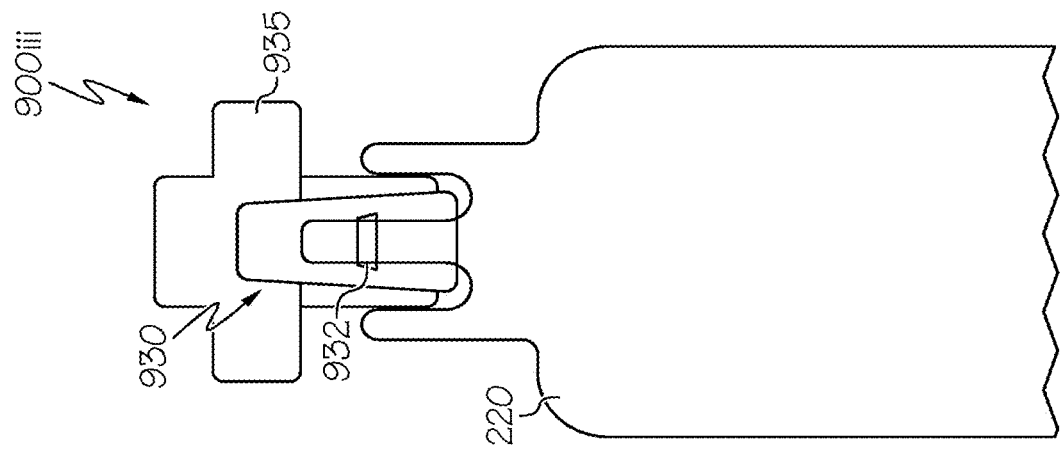
FIGS. 18A-C illustrate side views of another embodiment of a cap assembly proximate to and applied to a syringe, and a side view of a cap assembly applied to a syringe including a luer jacket, respectively, consistent with the present inventive concepts.
Figure 18B:
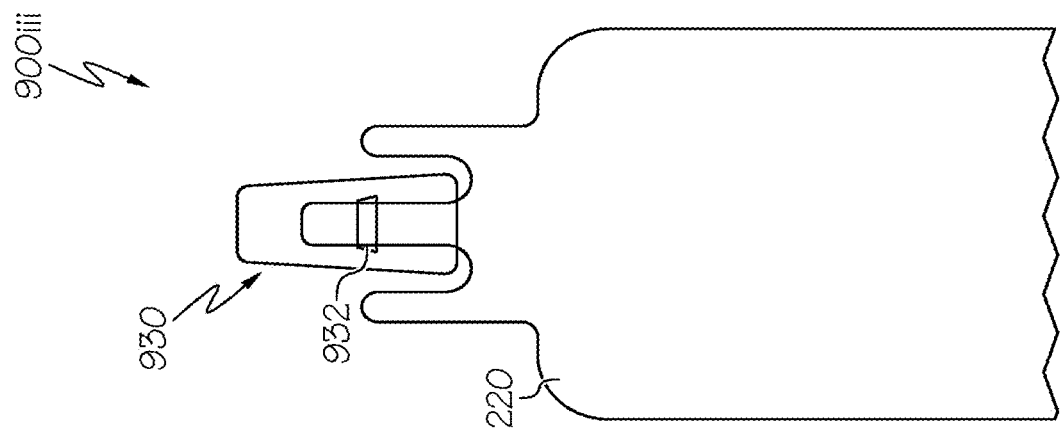
Figure 18A:
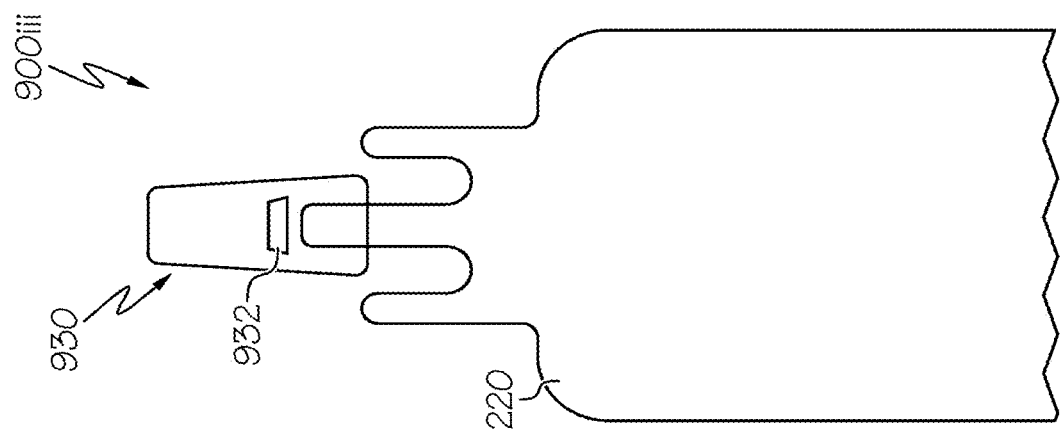

Referring specifically to FIGS. 18A-C, side views of another embodiment of a cap assembly proximate to and applied to a syringe, and a side view of a cap assembly applied to a syringe including a luer jacket are illustrated, respectively, consistent with the present inventive concepts. Cap assembly 900*iii*, as described herein, can be constructed and arranged to engage at least a portion of syringe 220, such as the tip of syringe 220. Cap assembly 900*iii* can include a stopper 930, such as a disposable rubber stopper. Stopper 930 can further comprise at least one fluid exchange element, vent 932 shown, configured to aid in the exchange of elements between syringe 220 and the external environment (e.g. when cap assembly 900*iiii* s partially attached to syringe 220 but not yet fully closed). During a lyophilization process, cap assembly 900*iii* can be configured to transition between an open and closed configuration, such as when stopper 930 is depressed or otherwise lowered onto syringe 220. In some embodiments, cap assembly 900*iiii* s mechanically lowered onto syringes 220, such as via capping apparatus 950 described herein. In other embodiments, cap assembly 900*iiii* s manually lowered onto syringes 220. In the open configuration, as shown in FIG. 18A, elements of the environment external to syringe 220 (e.g. fluid external to syringe 220) can interact with the contents of the syringe. In the closed configuration, as shown in FIG. 18B, elements of the environment external syringe 220 (e.g. fluid surrounding syringe 220) cannot interact with the contents of the syringe.

Cap assembly 900*iii* can further include a luer jacket 935. In some embodiments, at the conclusion of the lyophilization process, luer jacket 935 is applied to each stopper 930 and/or syringe 220, as shown in FIG. 18C. Luer jacket 935 can sliding engage at least a portion of stopper 930 and/or syringe 220, such as to create a fluid tight seal between syringe 220 and the external environment. In some embodiments, luer jacket 935 is mechanically lowered onto stopper 930 and/or syringe 220, such as via capping apparatus 950 described herein. In other embodiments, luer jacket 935 is manually lowered onto stopper 930 and/or syringe 220.

Figure 19:
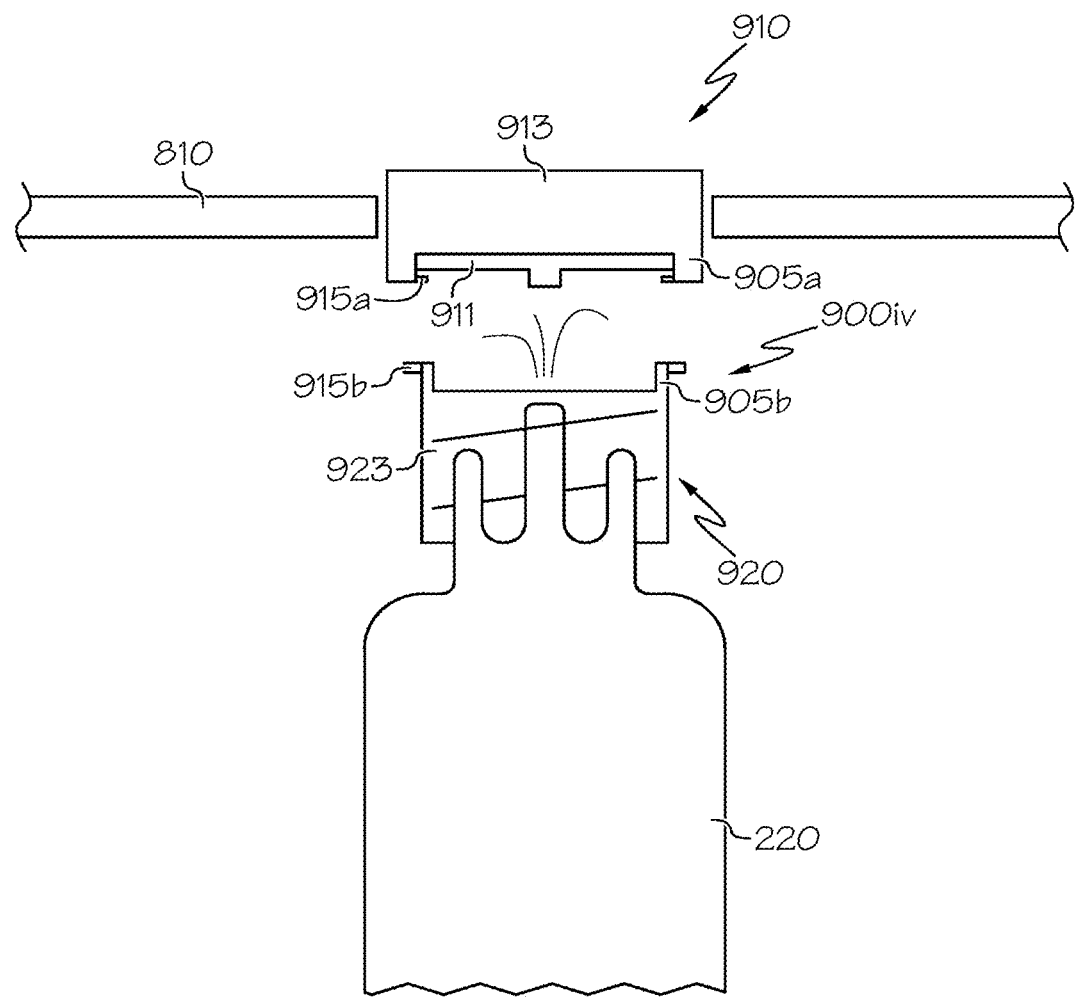
FIG. 19 illustrates a side view of another embodiment of a cap assembly proximate to a syringe, consistent with the present inventive concepts.

Referring specifically to FIG. 19, a side view of another embodiment of a cap assembly proximate to a syringe is illustrated, consistent with the present inventive concepts. Cap assembly 900*iv*, as described herein, can be constructed and arranged to engage at least a portion of syringe 220, such as the tip of syringe 220. Cap assembly 900iv can include a first portion 910 and a second portion 920 releasably interlocked via one or more projections 905a,b shown, respectively. First portion 910 and second portion 920 can further include one or more snap-fit elements, projections 915a,b shown, respectively, configured to releasably connect portions 910,920. First portion 910 can comprise a cap 913. Second portion 920 can comprise a luer lock tab 923. First portion 910 can be constructed as integral to (e.g. removably or fixedly attached to) upper assembly 810 of apparatus 800 described herein. A bottom surface of cap 913 can comprise a gasket 911. Second portion 920 can be secured to at least a portion of syringe 220, such as screwed to the tip of syringe 220. Tab 923 can comprise at least one fluid exchange element, vent 928 (not shown), configured to aid in the exchange of elements between syringe 220 and the external environment (e.g. when cap assembly 900iv is partially attached to syringe 220 but not yet fully closed).

During a lyophilization process, cap assembly 900iv can be configured to transition between an open and closed configuration, such as when first portion 910 is depressed or otherwise lowered onto second portion 920. First portion 910 and second portion 920 can be configured to interlock via projections 905a,b and gasket 911 provides a fluid tight seal. In some embodiments, first portion 910 is mechanically lowered onto second portion 920, such as via capping apparatus 950 described herein. In other embodiments, first portion 910 is manually lowered onto second portion 920. In the open configuration, as shown, elements of the environment external to syringe 220 (e.g. fluid surrounding syringe 220) can interact with the contents of the syringe. In the closed configuration, elements of the environment external to syringe 220 (e.g. fluid surrounding syringe 220) cannot interact with the contents of the syringe.

Figure 20A:
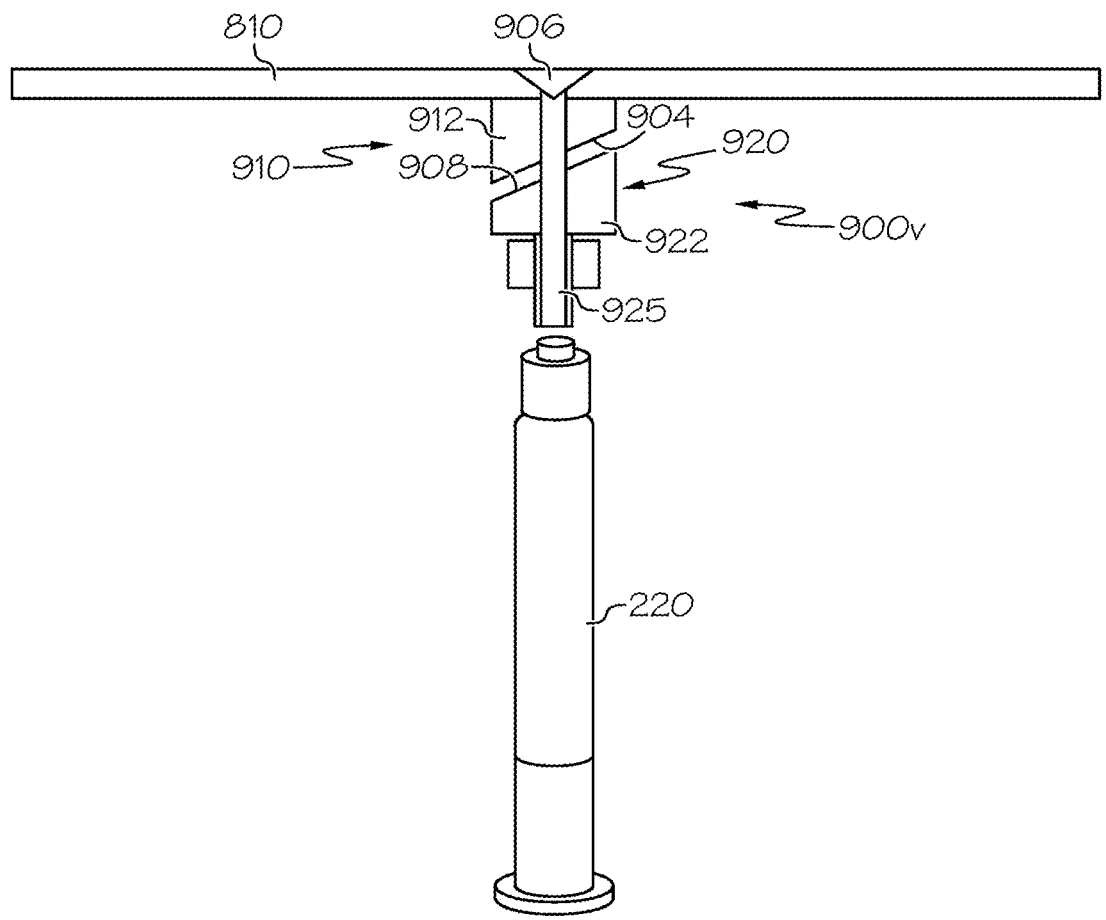
FIGS. 20A and 20B illustrate a side view and a magnified view of another embodiment of a cap assembly applied to a syringe, respectively, consistent with the present inventive concepts.
Figure 20B:
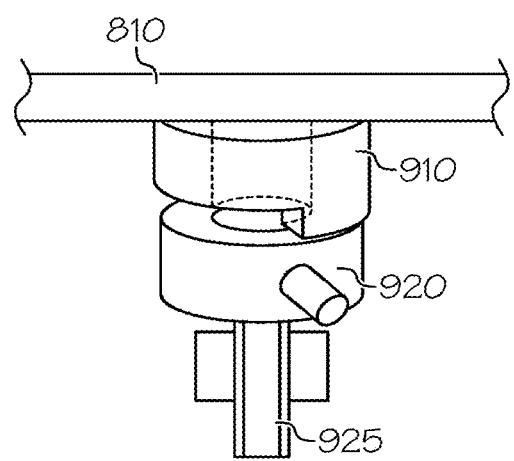

Referring specifically to FIGS. 20A and 20B, a side view and a magnified view of another embodiment of a cap assembly applied to a syringe are illustrated, respectively, consistent with the present inventive concepts. Cap assembly 900v, as described herein, can be constructed and arranged to engage at least a portion of syringe 220, such as the tip of syringe 220. Cap assembly 900v can include a first portion 910 and a second portion 920. First portion 910 can comprise a housing 912 with a lumen therethrough and a helical bottom surface 904. Second portion 920 can comprise a housing 922 with a lumen therethrough and a helical top surface 908. The mirroring bottom and top helical surfaces 904 and 908 can function as the "cam" and "follower" surfaces of a cylindrical cam, respectively. The cylindrical cam can leverage the opposing helical surfaces 904 and 908 on first portion 910 and second portion 920, respectively to frictionally engage such that first portion 910 and second portion 920 can rotate relative to one another (as shown in FIG. 20B) when a vertical down force is applied from upper assembly 810 to first portion 910 to second portion 920. Second portion 920 can further include a slotted socket to hold a female luer cap, cap 925, extending from a bottom surface of housing 922. In some embodiments, cap 925 is removably attached to second portion 920, such as via a temporary pressure fitting attachment mechanism inside the slotted socket.

Cap assembly 900v can further include a pin 906 that extends within the lumens of first portion 910 and second portion 920. Pin 906 can be constructed as integral to (e.g. removably or fixedly attached to) upper assembly 810 of apparatus 800 described herein. First portion 910 and second portion 920 can be configured to translate along pin 906, such that each portion 910, 920 can translate independently along at least a portion of pin 906. In some embodiments, pin 906 comprises a length that is greater than the combined length of portions 910, 920, such that pin 906 allows for a relative spacing between first portion 910 and second portion 920.

During a lyophilization process, cap assembly 900v can be configured to transition between an open and closed configuration, such as when cap 925 is depressed or otherwise lowered onto syringe 220 to provide a fluid tight seal. In some embodiments, cap assembly 900v is mechanically lowered onto syringes 220, such as via capping apparatus 950 described herein. In other embodiments, cap assembly 900v is manually lowered onto syringes 220. In the open configuration, as shown, elements of the environment external to syringe 220 (e.g. fluid surrounding syringe 220) can interact with the contents of the syringe. In the closed configuration, elements of the environment external syringe 220 (e.g. fluid surrounding syringe 220) cannot interact with the contents of the syringe.

Toward the end of a lyophilization process, upper assembly 810 can be configured to apply a vertical pressure to cap assembly 900v, such as when upper assembly 810 is lowered towards syringes 220. The vertical pressure can cause second portion 920 (e.g. cap 925) to engage at least a portion of syringe 220. Additionally, as upper assembly 810 applies pressure to first portion 910, pin 906 can extend into syringe 220, such that first portion 910 and second portion 920 translate towards each other along pin 906 to engage via angled surfaces 904, 908, respectively. Continued pressure can cause a rotation of portions 910, 920 via angled surfaces 904, 908, respectively. Rotation of portions 910, 920 can cause cap 925 to likewise rotate and screw onto syringe 220 to create a fluid tight seal.

Figure 21:
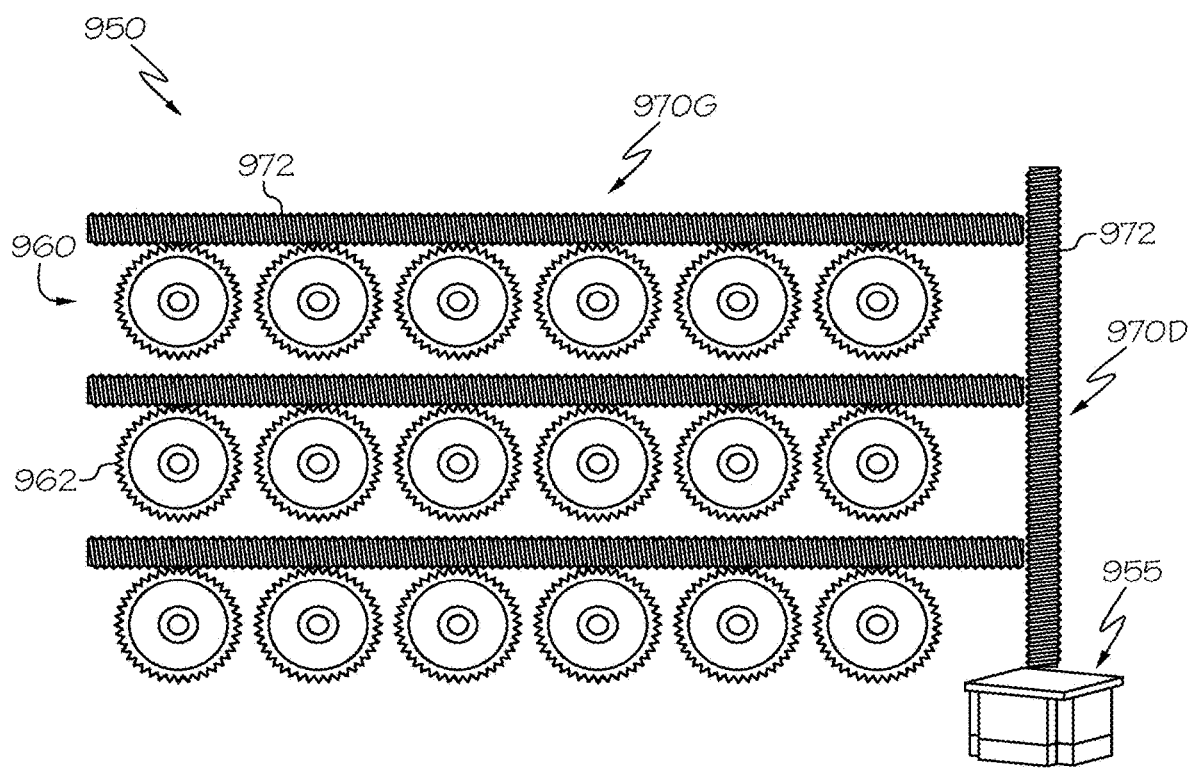
FIG. 21 illustrates a top view of an apparatus for applying a cap assembly to a syringe, consistent with the present inventive concepts.

Referring specifically to FIG. 21, a top view of an apparatus for applying a cap assembly to a syringe is illustrated, consistent with the present inventive concepts. Syringe holding apparatus 800 described herein can further include a capping apparatus 950. Capping apparatus 950 can be constructed and arranged to engage and/or manipulate one or more components of apparatus 800 (e.g. upper assembly 810) and/or cap assembly 900 described herein. Capping apparatus 950 can comprise a motorized assembly 955 comprising at least one of motor, battery, and/or controller (such as a motor driver card).

Capping apparatus 950 can further comprise one, two, or more rotatable gears 960 with a plurality of teeth 962 constructed about its circumference. Capping apparatus 950 can further comprise one, two, or more rotatable shafts 970, including at least one driver shaft 970D and at least one gear shaft 970G. Shafts 970D, 970G can further comprise at least one thread 972 constructed about its circumference. In some embodiments, gear shafts 970G comprise stainless steel shafts comprising a diameter of between 3 mm and 4 mm. In some embodiments, driver shaft 970D comprises a stainless steel shaft comprising a diameter of between 5 mm and 6 mm.

Driver shaft 970D can be positioned perpendicular to gear shaft 970G, and which can be fixedly attached via a gear 975 (not shown), such that a rotation of driver shaft 970D causes a corresponding rotation of gear shaft 970G via gear 975. Driver shaft 970D can be mechanically connected to motorized assembly 955. Gear shafts 970G can be arranged in a parallel orientation with a plurality of gears 960 positioned in between each gear shaft. For example, capping apparatus 950 can comprise ten gear shafts 970G with ten gears 960 positioned in between each gear shaft. Gear shaft 970G can be configured to manipulate (e.g. rotate) gears 960, such that the thread 972 of shafts 970G engages the teeth 962 of gear 960. Rotation of driver shaft 970D, as powered by motorized assembly 955, causes a corresponding rotation of gear shaft 970G, which further causes a rotation of gears 960.

In some embodiments, gears 960 can be configured to engage and manipulate at least a portion of cap assembly 900. For example, each gear 960 can be configured to engage and rotate a first portion 910 of cap assembly 900ii described herein in reference to FIGS. 17A,B. As another example, each gear 960 can be configured to engage and lower a first portion 910 of cap assembly 900iv described herein in reference to FIG. 19.

Toward the end of a lyophilization process, upper assembly 810 can be configured to apply a vertical pressure to cap assembly 900, such as when upper assembly 810 is lowered towards syringes 220. At least a portion of cap assembly 900 can align and/or come in contact with at least a portion of syringe 220. Motorized assembly 955 can be activated and can cause a rotation of driver shaft 970D, thereby causing a corresponding rotation of gear shaft 970G, which further causes a rotation of gears 960. Rotation of gears 960 can cause at least a portion of cap assembly 900 to further engage syringe 220. For example, each gear 960 can engage and rotate a first portion 910 of cap assembly 900ii described herein in reference to FIGS. 17A,B. As another example, each gear 960 can engage and lower a first portion 910 of cap assembly 900iv described herein in reference to FIG. 19.

Figure 22:
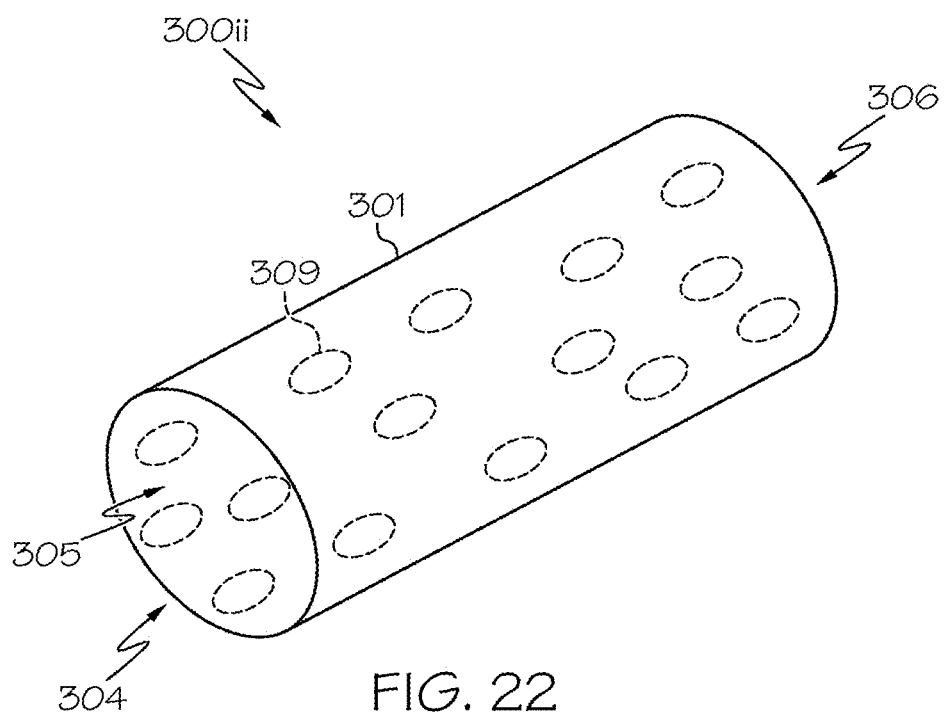
FIG. 22 illustrates a perspective view of a support assembly for manufacturing a nerve graft, nerve conduit, or nerve graft-conduit combination, consistent with the present inventive concepts.

Referring now to FIG. 22, a perspective view of a support assembly for manufacturing a nerve graft, nerve conduit, or nerve graft-conduit combination is illustrated, consistent with the present inventive concepts. Support assembly 300ii can comprise a housing 301 constructed and arranged as a cylindrical tube with a lumen 305 therethrough. Housing 301 comprises a proximal end 304 and a distal end 306. Support assembly 300ii can be configured to receive raw material 65, device 100, device 400, and/or ECM 120 (collectively "contents" herebelow).

Support assembly 300ii can comprise a plurality of pores 309. Each pore 309 can have diameter of between 0.1 micron and 500 microns. Pores 309 can be distributed uniformly along the longitudinal and/or circumferential directions of housing 301. In some embodiments, pores 309 are configured to allow for the passage of a fluid or vapor between support assembly 300ii (e.g. contents therein) and an external environment. In some embodiments, a vacuum source is applied to support assembly 300ii and pores 309 are configured to apply a uniform vacuum to the contents within support assembly 300ii. The vacuum source can be configured to maintain uniform contact between an outer surface of the contents and an inner surface of support assembly 300ii. One or more thermal and/or physical treatments can be applied concurrently with the vacuum source, such as to induce the formation of coaxial layers within the contents as a result of tissue contraction and/or shearing.

Support assembly 300ii can comprise a material selected from the group consisting of: expanded and non-expanded poly fluoro tetraethylene; polysulfones; cellulose acetate; polyamide; polyvinylidene fluoride; polysulfone; polyethersulfone; polyvinyl chloride; polyimide; polyacrylonitrile; polyethylene glycol; polyvinyl alcohol; poly(methacrylic acid); poly(arylene ether ketone); poly(ether imide); and polyaniline nanoparticles; stainless steel, such as 316L stainless steel; aluminum; cobalt alloy; titanium alloy; and combinations of these. In some embodiments, support assembly 300ii comprises a hydrophobic, expanded poly fluoro tetraethylene (ePTFE) tube comprising a porosity of between 50 and 60%, a wall thickness of between 0.3 and 0.8 mm, and/or a length of between 1 and 10 mm.

Support assembly 300ii can further comprise one, two, or more elements configured to impart structural modifications to the contents therein. For example, support assembly 300ii can be configured to impart a plurality of channels (e.g. lumens) to raw material 65, device 100, device 400, and/or ECM 120 via ablation and/or sublimation processes using an excimer laser.

Support assembly 300ii can be constructed and arranged to slidingly receive contents therein. For example, a nerve segment can be pulled into assembly 300 (e.g. lumen 305) using a suture ligation anchored at one end of the nerve segment. The suture ligation can be pulled through assembly 300 (e.g. lumen 305) until a desired portion of the nerve segment is positioned within the assembly.

Support assembly 300ii can be constructed and arranged as a compressive, porous, tubular structure configured to constrict or restrict the contents therein. Support assembly 300ii can be configured to promote the homogenous lyophilization of the contents therein. Support assembly 300ii can be configured to homogenize the diameter of the contents therein. Support assembly 300ii can be configured to reduce the size of the contents therein according to a diameter conversion factor. Support assembly 300ii can be configured to alter the length of the contents therein according to a conversion factor.

As described herein in reference to FIG. 22, support assembly 300ii and the related methods can be configured to manufacture at least a portion of implant 20, device 100, device 400, and/or ECM 120 as described herein.

Referring now to FIG. 23, a schematic view of cassette for securing one or more nerve segments is illustrated, consistent with the present inventive concepts. Nerve cassette 620 can comprise a housing 621 comprising one, two, or more channels 625 each configured to receive a nerve segment, such as raw material 65 described herein. Housing 621 can further comprise one or more dividers 623 configured to provide a barrier between adjacent channels 625. Housing 621 can comprise one or more fluid-permeable materials configured to allow for the passage of a fluid between cassette 620 (e.g. channels 623 therein) and an external environment.

Channels 625 can be configured to prevent or otherwise reduce bunching of the nerve segments. Each channel 625 can comprise a straight and/or spiral shape.

Once inserted into a channel 625, each nerve segment can be removably attached to housing 621 via one or more anchoring elements 627. In some embodiments, both ends of the nerve segment are secured via an anchoring element 627.

Referring now to FIG. 24, a perspective view of a medical device comprising a nerve graft-conduit is illustrated, consistent with the present inventive concepts. System 10 can further comprise medical device 400 shown. Device 400 comprises a nerve graft-conduit combination (e.g. artificial, natural, or combinations of these) configured to connect, or otherwise provide one, two, or more channels, between two or more anatomical elements (e.g. nerve stumps, nerve fascicles, etc.). Device 400 comprises a hybrid nerve graft-conduit combination derived, or otherwise produced, from one, two, or more raw material 65 as described herein. In some embodiments, raw material 65 comprises porcine peripheral nerve tissue. Device 400 is derived from raw material 65 according to Methods 11000-18000 as described herein in reference to FIGS. 26-33, respectively.

Device 400 can comprise at least a first end 401 and at least a second end 403, with at least one lumen 402 therebetween. First end 401 can be constructed and arranged to receive at least a portion of a first anatomical element (e.g. first nerve stump, first nerve fascicles, etc.) and second end 403 can be constructed and arranged to receive at least a portion of a second anatomical element (e.g. second nerve stump). Lumen 402 can be configured to receive, or otherwise comprise, a therapeutic device (e.g. device 100 of the present inventive concepts), such as to maintain the relative positioning of the therapeutic device between the two or more anatomical elements. Alternatively or additionally, first end 401 and/or second end 403 can be configured to receive, or otherwise comprise, a therapeutic device (e.g. device 100 of the present inventive concepts), such that the therapeutic device contacts at least a portion of the anatomical elements received by first end 401, second end 403.

Device 400 is configured to be deployed (e.g. injected, inserted, implanted, and the like) at one, two, or more "deposit sites", such as to provide a therapeutic benefit at one, two, or more "treatment sites". Each treatment site can comprise a location that is proximate to and/or remote from the associated deposit site. In some embodiments, a treatment site comprises a location that is relatively the same location as the associated deposit site. Device 400 can be deployed at the deposit site to promote, and/or otherwise support, tissue growth of a patient (e.g. support tissue growth and/or regeneration at locations proximate and/or remote from the deposit site). In some embodiments, device 400 is remodeled over time into native tissue of the patient. As used herein, the deposit site can comprise one, two, or more locations on and/or within the patient.

The deposit site can comprise a location similar to those as described herein in reference to device 100. In some embodiments, the deposit site comprises a location (e.g. one, two, three, or more locations) within the central nervous system, such as a site located within the brain and/or spinal cord. In some embodiments, the deposit site comprises a location within the peripheral nervous system, such as a site located outside the brain and spinal cord, including any location along the peripheral nervous system spanning from the dorsal and/or ventral root ganglia to motor, sensory, or autonomic endings (e.g. end-muscle plate, Pacinian corpuscle, Ruffini endings). In some embodiments, the deposit site comprises a location within and/or proximate a partial or full nerve transection, such as a transected and repaired nerve (e.g. epineural and/or fascicular repair, such as neurorrhaphy). For example, device 400 can be deployed to provide an interface between two or more nerve stumps. The two or more nerve stumps can be coapted together, such as via a suture or fibrin glue configured to eliminate or otherwise reduce a gap length between the nerve stumps. Alternatively, the two or more nerve stumps are not coapted together and a calculated gap length is maintained between the nerve stumps. The calculated gap length can be configured to promote nerve cone sprouting and alignment from a proximal nerve stump having a greater degree of freedom to properly align toward a distal nerve stump. In some embodiments, the deposit site comprises a location within and/or proximate a nerve injury repaired with a nerve transfer technique, such as an end-to-end transfer, side-to-side transfer, end-to-side transfer, or supercharged end-to-side transfer. In some embodiments, the deposit site comprises a location within and/or proximate a truncated nerve following an amputation. For example, device 400 can be deployed at the site of one or more nerves affected by an amputation.

Figure 25:
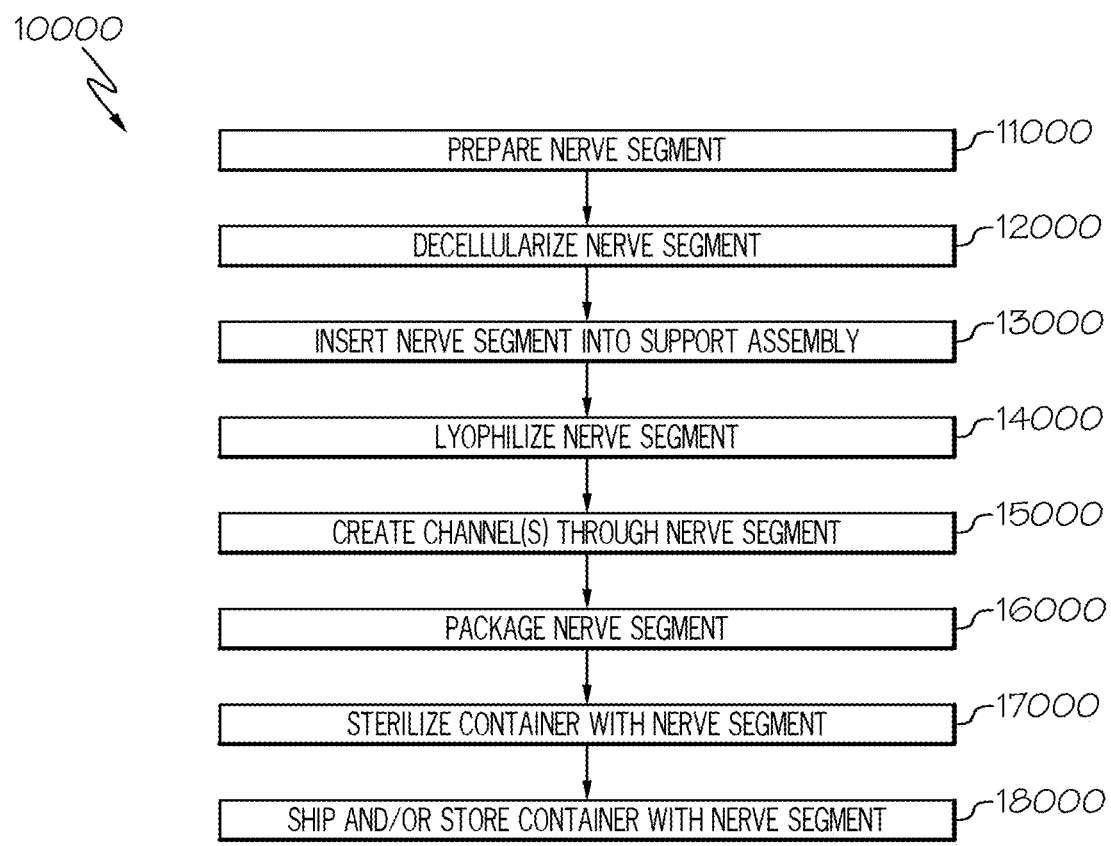
FIG. 25 illustrates a method for producing a nerve graft-conduit combination from tissue, consistent with the present inventive concepts.

Referring now to FIG. 25, a method for producing a nerve graft-conduit combination from tissue is illustrated, consistent with the present inventive concepts. Method 10000 comprises a sequence of sub-methods, Methods 11000, 12000, 13000, 14000, 15000, 16000, 17000, and 18000 as described herein in reference to FIGS. 26-33, respectively. Method 11000 comprises a method for harvesting and/or preparing tissue for further manipulation. Method 12000 comprises a method for decellularizing the tissue harvested and/or prepared in Method 11000. Method 13000 comprises a method for jacketing the decellularized tissue produced in Method 12000. Method 14000 comprises a method for lyophilizing the jacketed tissue produced in Method 13000. Method 15000 comprises a method for creating one or more channels (e.g. lumens) through the lyophilized tissue produced in Method 14000. Method 16000 comprises a method for packaging the nerve graft-conduit produced in Method 15000. Method 17000 comprises a method for sterilizing the container comprising the nerve graft-conduit produced in Method 16000. Method 18000 comprises a method for shipping and/or storing the container comprising the nerve graft-conduit combination produced in Method 17000.

Figure 26:
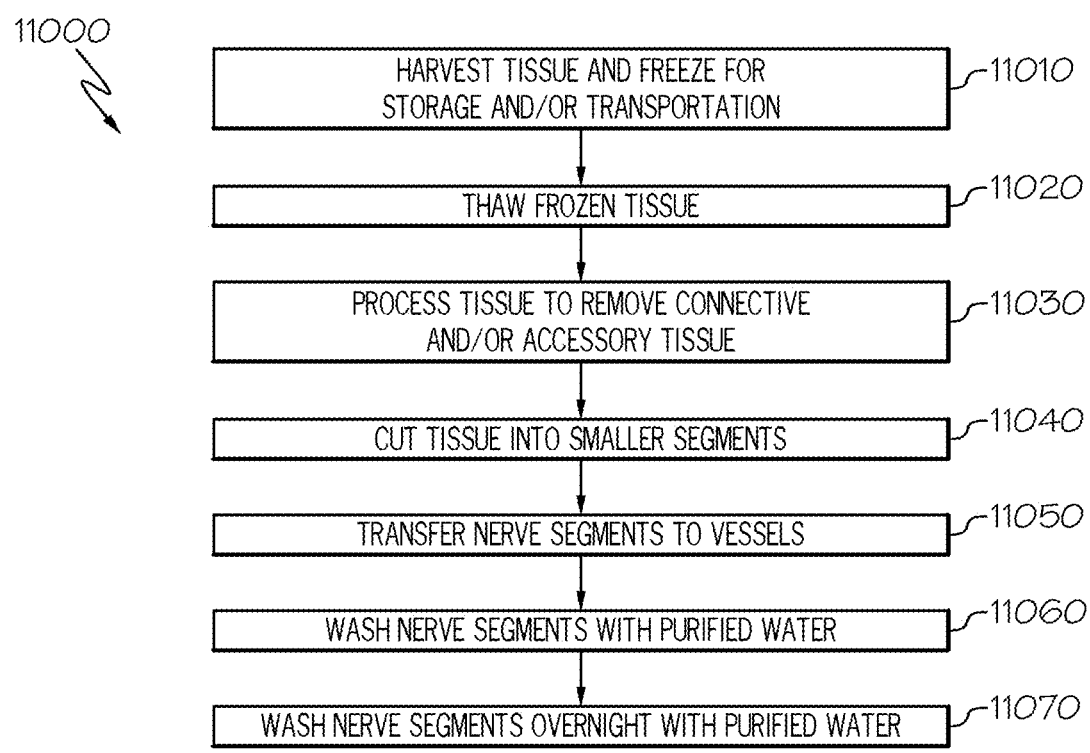
FIG. 26 illustrates a method for harvesting and/or preparing nerve tissue for further manipulation, consistent with the present inventive concepts.

Referring now to FIG. 26, a method for harvesting and/or preparing nerve tissue for further manipulation is illustrated, consistent with the present inventive concepts. Method 11000 can be configured to harvest and/or prepare raw material 65 from tissue source 60 described herein.

In STEP 11010, raw material 65 is harvested from a tissue source (e.g. tissue source 60). Additionally, raw material 65 can be processed to remove connective and/or accessory tissue (e.g. remove non-nerve tissue). For short-term storage (e.g. for a duration less than six hours), cleaned raw material 65 can be at least partially immersed in buffer solution 701. In some embodiments, raw material 65 can be stored in chamber 601 at a temperature between approximately 2° C. and 8° C. For long-term storage and/or transportation (e.g. for a duration more than six hours), raw material 65 can be rapidly frozen in buffer solution 701. In some embodiments, raw material 65 is rapidly frozen via cooling agent 702. Raw material 65 can be stored and/or transported in chamber 601 at a temperature of approximately −80° C. (or lower temperatures such as those afforded by dry ice or liquid nitrogen storage). In some embodiments, raw material 65 is stored in chamber 601 at a temperature of approximately −80° C. for a maximum of six months.

In STEP 11020, frozen raw material 65 is thawed in chamber 601 at a temperature of between 2° C. and 8° C. In some embodiments, raw material 65 is thawed in chamber 601 for at least 48 hours, such as at least 72 hours.

In STEP 11030, raw material 65 is further processed (e.g. cleaned) to remove additional connective and/or accessory tissue (e.g. remove non-nerve tissue). Raw material 65 can be processed at a temperature of between 2° C. and 25° C.

In some embodiments, raw material 65 comprises a portion of nerve tissue comprising one, two, or more side branches. The side branches can be removed and processed as described herein.

In STEP 11040, cleaned raw material 65 is cut, or otherwise divided, into smaller segments. Cleaned raw material 65 can be cut into segments comprising a length of between 0.5 cm and 20 cm, such as between 1 cm and 10 cm. Cleaned raw material 65 can comprise segments comprising a diameter of between 0.5 mm and 10 mm, such as between 1 mm and 5 mm.

In STEP 11050, raw material 65 is transferred to one, two, or more vessels 602. Cleaned raw material 65 can be transferred at a temperature of between 2° C. and 25° C. In some embodiments, each vessel 602 comprises no more than 25 g of cleaned raw material 65 and a mixing device 603 contains no more than six vessels 602.

In STEP 11060, cleaned raw material 65 is washed with purified water 703. Cleaned raw material 65 can be washed at a temperature of between 2° C. and 8° C. Cleaned raw material 65 is washed with purified water 703 at least two times, such as at least three times, such as at least four times. Cleaned raw material 65 and purified water 703 can comprise a ratio between 1:20 and 1:50, such as 1:30. In some embodiments, vessel 602 is placed into mixing device 603 comprising purified water 703, such as a mixing device comprising at least 3000 mL of purified water 703. Mixing device 603 is placed on top of heating device 604 configured to stir purified water 703 at a speed between 10 rpm and 1000 rpm, such as 100±10 rpm, for at least 10 minutes, thereby washing cleaned raw material 65 within vessel 602. Purified water 703 is decanted from mixing device 603 and replaced with fresh purified water 703. Mixing device 603 is placed back on top of heating device 604 configured to stir purified water 703 at a speed between 10 rpm and 1000 rpm, such as 100±10 rpm, for at least 10 minutes, thereby washing raw material 65 within vessel 602 a second time. Purified water 703 is decanted from mixing device 603.

In STEP 11070, cleaned raw material 65 is washed overnight with purified water 703. Cleaned raw material 65 can be washed at a temperature of between 2° C. and 8° C. Cleaned raw material 65 and purified water 703 can comprise a ratio between 1:20 and 1:50, such as 1:30. In some embodiments, vessel 602 is placed into mixing device 603 comprising purified water 703, such as a mixing device comprising at least 3000 mL of purified water 703. Mixing device 603 is stored in chamber 601 at a temperature of approximately 5° C. for between 12 hours and 24 hours, such as 16 hours. During this time, mixing device 603 is placed on top of heating device 604 configured to stir purified water 703 at a speed between 10 rpm and 1000 rpm, such as 100±10 rpm, thereby washing cleaned raw material 65 within vessel 602.

Figure 27:
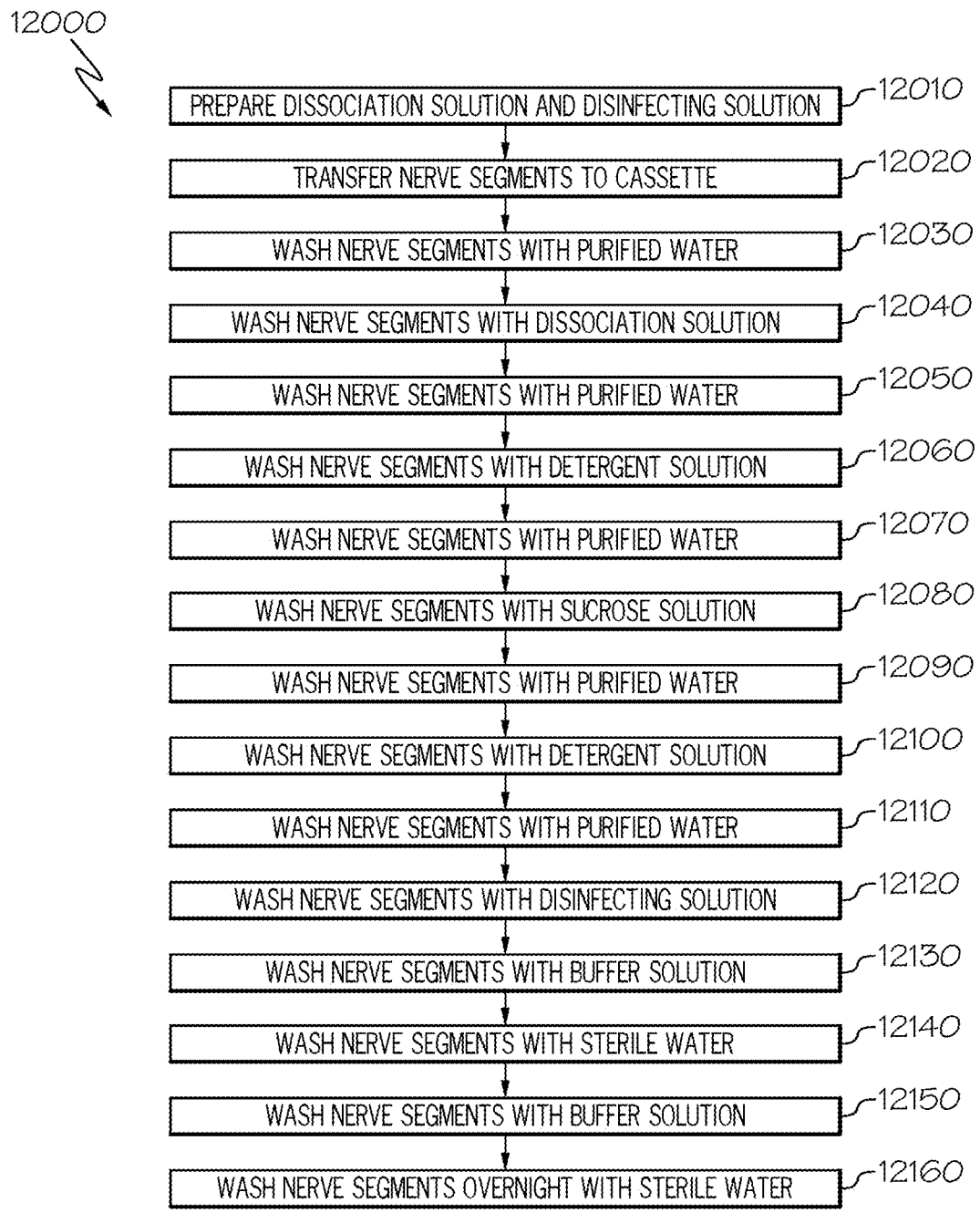
FIG. 27 illustrates a method for decellularizing a nerve segment, consistent with the present inventive concepts.

Referring now to FIG. 27, a method for decellularizing a nerve segment is illustrated, consistent with the present inventive concepts. Method 12000 can be configured to decellularize cleaned raw material 65 harvested and/or prepared in Method 11000 described herein in reference to FIG. 26.

In STEP 12010, dissociation solution 704 and disinfecting solution 705 are prepared. Dissociation solution 704 and disinfecting solution 705 can be prepared at a temperature of between 2° C. and 25° C.

IN STEP 12020, cleaned raw material 65 from STEP 12010 is removed from vessel 602 and transferred to one or more cassettes 620. One or more portions of raw material 65 can be anchored to cassette 620, such as to secure raw material 65 to and/or within cassette 620.

IN STEP 12030, cleaned raw material 65 is washed with purified water 703. In some embodiments, purified water 703 is pre-chilled in chamber 601 to a temperature of between 2° C. and 8° C. Cleaned raw material 65 is washed with purified water 703 at least two times. Cleaned raw material 65 and purified water 703 can comprise a ratio between 1:20 and 1:50, such as 1:30. Purified water 703 is added to mixing device 603. In some embodiments, at least 3000 mL of purified water 703 is added to mixing device 603. Mixing device 603 is stored in chamber 601 at a temperature of approximately 5° C. Mixing device 603 is placed on top of heating device 604 configured to stir purified water 703 at 100±10 rpm, for at least 10 minutes, thereby washing cleaned raw material 65 within vessel 602. Purified water 703 is decanted from mixing device 603 and replaced with fresh purified water 703. Mixing device 603 is placed back on top of heating device 604 configured to stir purified water 703 at a speed between 10 rpm and 1000 rpm, such as 100±10 rpm, for at least 10 minutes, thereby washing cleaned raw material 65 within vessel 602 a second time. Purified water 703 is decanted from mixing device 603.

In STEP 12040, cleaned raw material 65 is washed with dissociation solution 704. Dissociation solution 704 can comprise a temperature of between 2° C. and 37° C., such as 35±2° C. Cleaned raw material 65 and dissociation solution 704 can comprise a ratio between 1:20 and 1:50, such as 1:30. Dissociation solution 704 is added to mixing device 603. In some embodiments, at least 3000 mL of dissociation solution 704 is added to mixing device 603. Mixing device 603 is placed on top of heating device 604 configured to stir dissociation solution 704 at a speed between 10 rpm and 1000 rpm, such as 100±10 rpm, thereby washing cleaned raw material 65 within vessel 602. Cleaned raw material 65 is washed in chamber 601 at a temperature of between 2° C. and 37° C., such as 35±2° C., for between 30 minutes and 180 minutes, such as 60±5 minutes. In some embodiments, a lipid layer forms on the surface of dissociation solution 704 and is removed using instrument 605. Dissociation solution 704 is decanted from mixing device 603.

In STEP 12050, cleaned raw material 65 is washed with purified water 703. In some embodiments, purified water 703 is pre-chilled in chamber 601 to a temperature of between 2° C. and 8° C. Cleaned raw material 65 is washed with purified water 703 at least six times. Cleaned raw material 65 and purified water 703 can comprise a ratio between 1:20 and 1:50, such as 1:30. Purified water 703 is added to mixing device 603. In some embodiments, at least 3000 mL of purified water 703 is added to mixing device 603. Mixing device 603 is stored in chamber 601 at a temperature of approximately 5° C. Mixing device 603 is placed on top of heating device 604 configured to stir purified water 703 at a speed between 10 rpm and 1000 rpm, such as 100±10 rpm, for at least 5 minutes, thereby washing cleaned raw material 65 within vessel 602. Purified water 703 is decanted from mixing device 603 and replaced with fresh purified water 703. This process is repeated at least five additional times, thereby washing cleaned raw material 65 within vessel 602 at least six times.

In STEP 12060, cleaned raw material 65 is washed with detergent solution 706. In some embodiments, detergent solution 706 is pre-chilled in chamber 601 to a temperature of between 2° C. and 8° C. Cleaned raw material 65 and detergent solution 706 can comprise a ratio between 1:20 and 1:50, such as 1:30. Detergent solution 706 is added to mixing device 603. In some embodiments, at least 3000 mL of detergent solution 706 is added to mixing device 603. Mixing device 603 is stored in chamber 601 at a temperature of between 2° C. and 8° C., such as approximately 4° C. Mixing device 603 is placed on top of heating device 604 configured to stir detergent solution 706 at a speed between 10 rpm and 1000 rpm, such as 100±10 rpm, for between 30 minutes and 180 minutes, such as 60±5 minutes, thereby washing cleaned raw material 65 within vessel 602. Detergent solution 706 is decanted from mixing device 603.

In STEP 12070, cleaned raw material 65 is washed with purified water 703. In some embodiments, purified water 703 is pre-chilled in chamber 601 to a temperature of between 2° C. and 8° C., such as approximately 4° C. Cleaned raw material 65 is washed with purified water 703 at least six times. Cleaned raw material 65 and purified water 703 can comprise a ratio between 1:20 and 1:50, such as 1:30. Purified water 703 is added to mixing device 603. In some embodiments, at least 3000 mL of purified water 703 is added to mixing device 603. Mixing device 603 is stored in chamber 601 at a temperature of between 2° C. and 8° C., such as approximately 4° C. Mixing device 603 is placed on top of heating device 604 configured to stir purified water 703 at a speed between 10 rpm and 1000 rpm, such as 100±10 rpm, for at least 5 minutes, thereby washing cleaned raw material 65 within vessel 602. Purified water 703 is decanted from mixing device 603 and replaced with fresh purified water 703. This process is repeated at least five additional times, thereby washing cleaned raw material 65 within vessel 602 at least six times.

In STEP 12080, cleaned raw material 65 is washed with sucrose solution 707. In some embodiments, sucrose solution 707 is pre-chilled in chamber 601 to a temperature of between 2° C. and 8° C., such as approximately 4° C. Cleaned raw material 65 and sucrose solution 707 can comprise a ratio between 1:20 and 1:50, such as 1:30. Sucrose solution 707 is added to mixing device 603. In some embodiments, at least 3000 mL of sucrose solution 707 is added to mixing device 603. Mixing device 603 is stored in chamber 601 at a temperature of between 2° C. and 8° C., such as approximately 4° C. Mixing device 603 is placed on top of heating device 604 configured to stir sucrose solution 707 at a speed between 10 rpm and 1000 rpm, such as 100±10 rpm, for between 5 minutes and 60 minutes, such as 15±5 minutes, thereby washing cleaned raw material 65 within vessel 602. Sucrose solution 707 is decanted from mixing device 603.

In STEP 12090, cleaned raw material 65 is washed with purified water 703. In some embodiments, purified water 703 is pre-chilled in chamber 601 to a temperature of between 2° C. and 8° C., such as approximately 4° C. Cleaned raw material 65 is washed with purified water 703 at least six times. Cleaned raw material 65 and purified water 703 can comprise a ratio between 1:20 and 1:50, such as 1:30. Purified water 703 is added to mixing device 603. In some embodiments, at least 3000 mL of purified water 703 is added to mixing device 603. Mixing device 603 is stored in chamber 601 at a temperature of between 2° C. and 8° C., such as approximately 4° C. Mixing device 603 is placed on top of heating device 604 configured to stir purified water 703 at a speed between 10 rpm and 1000 rpm, such as 100±10 rpm, for at least 5 minutes, thereby washing cleaned raw material 65 within vessel 602. Purified water 703 is decanted from mixing device 603 and replaced with fresh purified water 703. This process is repeated at least five additional times, thereby washing cleaned raw material 65 within vessel 602 at least six times.

In STEP 12100, cleaned raw material 65 is washed with detergent solution 706. In some embodiments, detergent solution 706 is pre-chilled in chamber 601 to a temperature of between 2° C. and 8° C., such as approximately 4° C. Cleaned raw material 65 and detergent solution 706 can comprise a ratio between 1:20 and 1:50, such as 1:30. Detergent solution 706 is added to mixing device 603. In some embodiments, at least 3000 mL of detergent solution 706 is added to mixing device 603. Mixing device 603 is stored in chamber 601 at a temperature of between 2° C. and 8° C., such as approximately 4° C. Mixing device 603 is placed on top of heating device 604 configured to stir detergent solution 706 at a speed between 10 rpm and 1000 rpm, such as 100±10 rpm, for between 30 minutes and 180 minutes, such as 60±5 minutes, thereby washing cleaned raw material 65 within vessel 602. Detergent solution 706 is decanted from mixing device 603.

In STEP 12110, cleaned raw material 65 is washed with purified water 703. In some embodiments, purified water 703 is pre-chilled in chamber 601 to a temperature of between 2° C. and 8° C., such as approximately 4° C. Cleaned raw material 65 is washed with purified water 703 at least six times. Cleaned raw material 65 and purified water 703 can comprise a ratio between 1:20 and 1:50, such as 1:30. Purified water 703 is added to mixing device 603. In some embodiments, at least 3000 mL of purified water 703 is added to mixing device 603. Mixing device 603 is stored in chamber 601 at a temperature of between 2° C. and 8° C., such as approximately 4° C. Mixing device 603 is placed on top of heating device 604 configured to stir purified water 703 at a speed between 10 rpm and 1000 rpm, such as 100±10 rpm, for at least 5 minutes, thereby washing cleaned raw material 65 within vessel 602. Purified water 703 is decanted from mixing device 603 and replaced with fresh purified water 703. This process is repeated at least five additional times, thereby washing cleaned raw material 65 within vessel 602 at least six times.

In STEP 12120, cleaned raw material 65 is washed with disinfecting solution 705. In some embodiments, disinfecting solution 705 is pre-chilled in chamber 601 to a temperature of between 2° C. and 8° C., such as approximately 4° C. Cleaned raw material 65 and disinfecting solution 705 can comprise a ratio between 1:20 and 1:50, such as 1:30. Disinfecting solution 705 is added to mixing device 603. In some embodiments, at least 3000 mL of disinfecting solution 705 is added to mixing device 603. Mixing device 603 is stored in chamber 601 at a temperature of between 2° C. and 8° C., such as approximately 4° C. Mixing device 603 is placed on top of heating device 604 configured to stir disinfecting solution 705 at a speed between 10 rpm and 1000 rpm, such as 100±10 rpm, for between 30 minutes and 240 minutes, such as 120±5 minutes, thereby washing cleaned raw material 65 within vessel 602. Disinfecting solution 705 is decanted from mixing device 603.

In STEP 12130, cleaned raw material 65 is washed with buffer solution 701. In some embodiments, buffer solution 701 is pre-chilled in chamber 601 to a temperature of between 2° C. and 8° C., such as approximately 4° C. Raw material 65 and buffer solution 701 can comprise a ratio between 1:20 and 1:50, such as 1:30. Buffer solution 701 is added to mixing device 603. In some embodiments, at least 3000 mL of buffer solution 701 is added to mixing device 603. Mixing device 603 is stored in chamber 601 at a temperature of between 2° C. and 8° C., such as approximately 4° C. Mixing device 603 is placed on top of heating device 604 configured to stir buffer solution 701 at speed between 10 rpm and 1000 rpm, such as 100±10 rpm, for between 5 minutes and 60 minutes, such as 15±5 minutes, thereby washing cleaned raw material 65 within vessel 602. Buffer solution 701 is decanted from mixing device 603.

In STEP 12140, cleaned raw material 65 is washed with sterile water 708. In some embodiments, sterile water 708 is pre-chilled in chamber 601 to a temperature of between 2° C. and 8° C., such as approximately 4° C. Cleaned raw material 65 is washed with sterile water 708 at least two times. Cleaned raw material 65 and sterile water 708 can comprise a ratio between 1:20 and 1:50, such as 1:30. Sterile water 708 is added to mixing device 603. In some embodiments, at least 3000 mL of sterile water 708 is added to mixing device 603. Mixing device 603 is stored in chamber 601 at a temperature of between 2° C. and 8° C., such as approximately 4° C. Mixing device 603 is placed on top of heating device 604 configured to stir sterile water solution at a speed between 10 rpm and 1000 rpm, such as 100±10 rpm, for between 5 minutes and 60 minutes, such as 15±5 minutes, thereby washing cleaned raw material 65 within vessel 602. Sterile water 708 is decanted from mixing device 603 and replaced with fresh sterile water solution. Mixing device 603 is placed back on top of heating device 604 configured to stir sterile water 708 at a speed between 10 rpm and 1000 rpm, such as 100±10 rpm, for between 5 minutes and 60 minutes, such as 15±5 minutes, thereby washing cleaned raw material 65 within vessel 602 a second time. Sterile water 708 is decanted from mixing device 603.

In STEP 12150, cleaned raw material 65 is washed with buffer solution. In some embodiments, buffer solution 701 is pre-chilled in chamber 601 to a temperature of between 2° C. and 8° C., such as approximately 4° C. Cleaned raw material 65 and buffer solution 701 can comprise a ratio between 1:20 and 1:50, such as 1:30. Buffer solution 701 is added to mixing device 603. In some embodiments, at least 3000 mL of buffer solution 701 is added to mixing device 603. Mixing device 603 is stored in chamber 601 at a temperature of between 2° C. and 8° C., such as approximately 4° C. Mixing device 603 is placed on top of heating device 604 configured to stir buffer solution 701 at a speed between 10 rpm and 1000 rpm, such as 100±10 rpm, for between 5 minutes and 60 minutes, such as 15±5 minutes, thereby washing cleaned raw material 65 within vessel 602. Buffer solution 701 is decanted from mixing device 603.

In STEP 12160, cleaned raw material 65 is washed overnight with sterile water. In some embodiments, sterile water 708 is pre-chilled in chamber 601 to a temperature of between 2° C. and 8° C., such as approximately 4° C. Cleaned raw material 65 and sterile water 708 can comprise a ratio between 1:20 and 1:50, such as 1:30. Sterile water 708 is added to mixing device 603. In some embodiments, at least 3000 mL of sterile water 708 is added to mixing device 603. Mixing device 603 is stored in chamber 601 at a temperature of between 2° C. and 8° C., such as approximately 4° C., for between 12 hours and 24 hours, such as 16±2 hours. During this time, mixing device 603 is placed on top of heating device 604 configured to stir purified water 703 at a speed between 10 rpm and 1000 rpm, such as 100±10 rpm, thereby washing cleaned raw material 65 within vessel 602. Sterile water 708 is decanted from mixing device 603.

Upon the conclusion of Method 1200, cleaned raw material 65 comprises a decellularized segmented nerve tissue (referred to as "nerve segment" herein).

Figure 28:
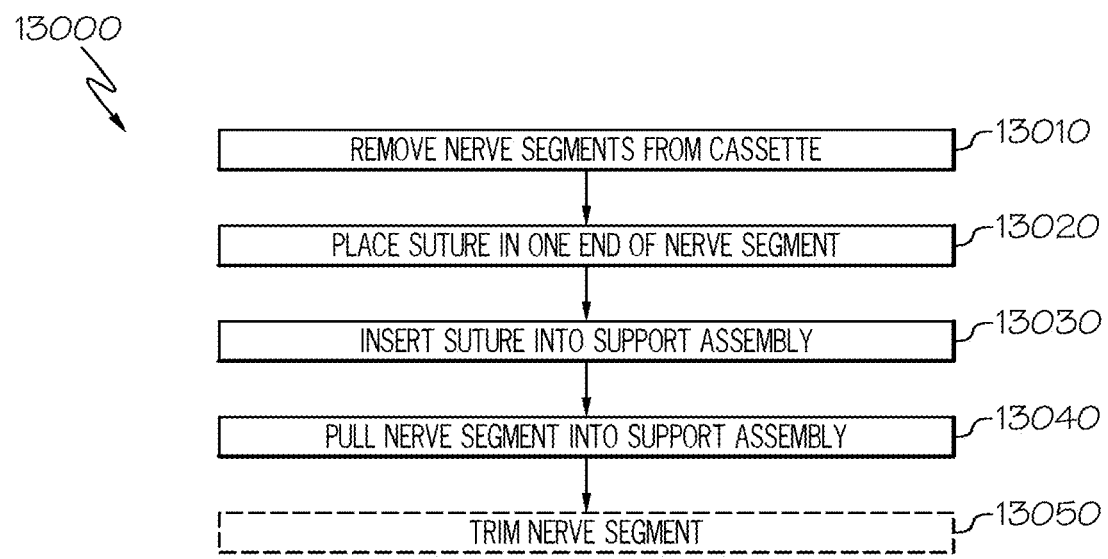
FIG. 28 illustrates a method for inserting a nerve segment into a support assembly, consistent with the present inventive concepts.

Referring now to FIG. 28, a method for inserting a nerve segment into a support assembly is illustrated, consistent with the present inventive concepts. Method 13000 can be configured to insert a nerve segment produced in Method 12000 described herein in reference to FIG. 27.

In STEP 13010, the nerve segment is removed from cassette 620.

In STEP 13020, a suture ligation is created and secured through a first end of the nerve segment. In some embodiments, a silk suture with a noose is created and secured through the first end of the nerve segment.

In STEP 13030, the suture is inserted into lumen 305 of support assembly 300*ii* via proximal end 304.

In STEP 13040, the suture is pulled through support assembly 300*ii* such that the nerve segment is advanced into lumen 305. In some embodiments, the suture is pulled through support assembly 300*ii* until the first end of the nerve segment is proximate distal end 306 of support assembly 300*ii*.

In STEP 13050, comprising an optional step, any portion of the nerve segment that is not contained within support assembly 300*ii* can be removed (e.g. cut, or otherwise detached) and discarded. In some embodiments, support assembly 300*ii* comprises a length of approximately 1 cm and any portion of the nerve segment that extends beyond support assembly 300*ii* is removed or otherwise detached (e.g. the nerve segment is cut to comprise a length of approximately 1 cm).

Figure 29:
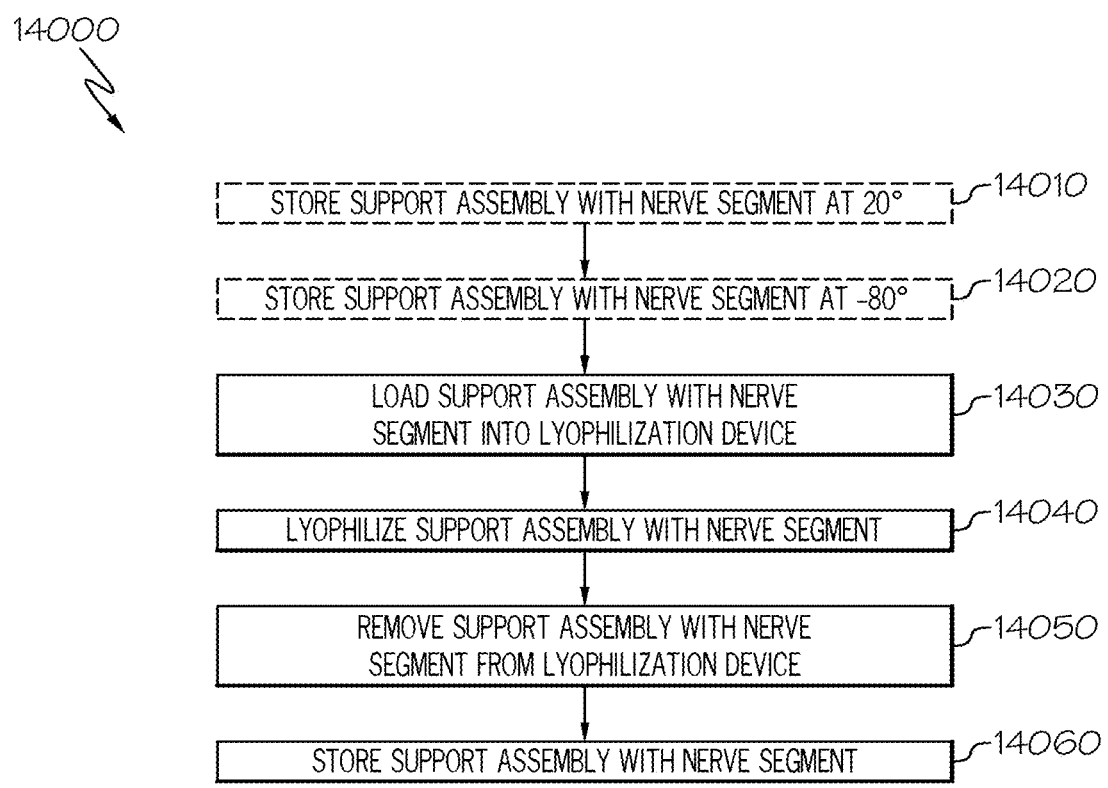
FIG. 29 illustrates a method for lyophilizing a nerve segment contained within a support assembly, consistent with the present inventive concepts.
Figure 30:
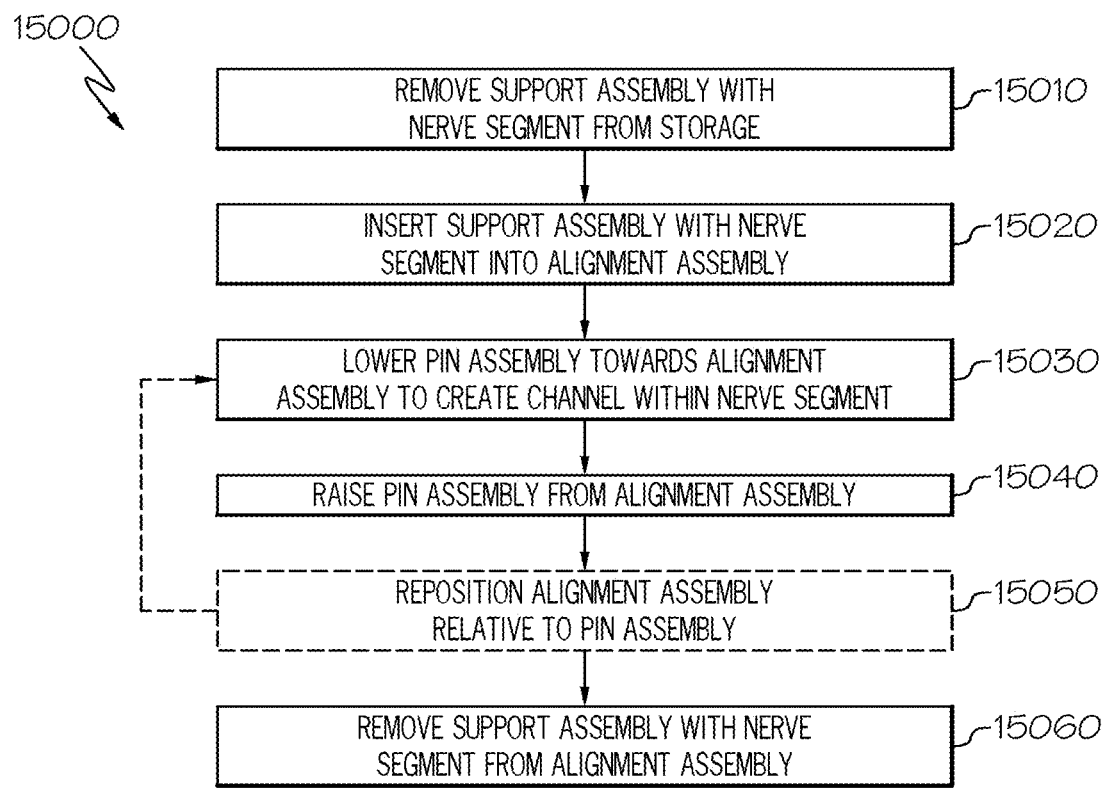

Referring now to FIG. 29, a method for lyophilizing a nerve segment contained within a support assembly is illustrated, consistent with the present inventive concepts. Method 14000 can be configured to lyophilize a nerve segment contained within a support assembly produced in Method 13000 described herein in reference to FIG. 28.

In STEP 14010, comprising an optional step, support assemblies 300*ii* comprising nerve segments can be transferred to, and stored within, chamber 601 comprising a temperature of 20° C. In some embodiments, support assemblies 300*ii* comprising nerve segments are stored in chamber 601 overnight.

In STEP 14020, comprising an optional step, support assemblies 300*ii* comprising nerve segments can be transferred to, and stored within, chamber 601 comprising a temperature of −80° C. In some embodiments, support assemblies 300*ii* comprising nerve segments are stored in chamber 601 for a few hours.

In STEP 14030, one, two, or more support assemblies 300*ii* comprising nerve segments are loaded into lyophilization device 606. In some embodiments, support assemblies 300*ii* comprising nerve segments are loaded into a preconditioned lyophilization device 606.

In STEP 14040, support assemblies 300*ii* comprising nerve segments are lyophilized via lyophilization device 606. In some embodiments, support assemblies 300*ii* comprising nerve segments are lyophilized for 72 hours.

In STEP 14050, support assemblies 300*ii* comprising nerve segments are removed from lyophilization device 606.

In STEP 14060, support assemblies 300*ii* comprising nerve segments are transferred to, and stored within, chamber 601 comprising a temperature between 2° C. and 8° C.

Upon the conclusion of Method 14000, the nerve segments comprise lyophilized nerve segments (referred to as "lyophilized nerve segment" herein).

Figure 30:
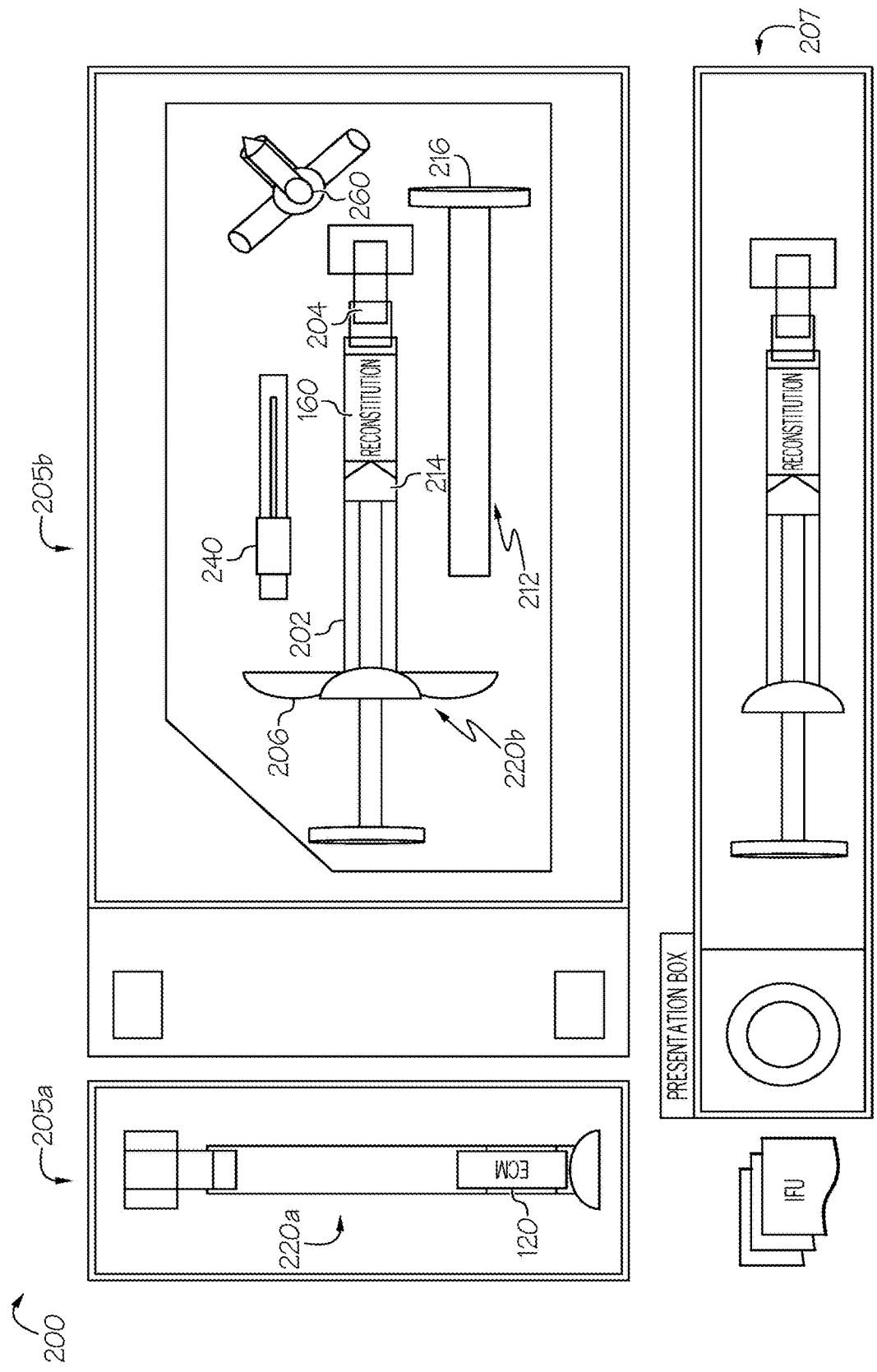
FIG. 30 illustrates a method for creating channels through a nerve segment, consistent with the present inventive concepts.

Referring now to FIG. 30, a method for creating channels through a nerve segment is illustrated, consistent with the present inventive concepts. Method 15000 can be configured to create one, two, or more channels (e.g. lumens) through lyophilized nerve segments produced in Method 14000 described herein in reference to FIG. 29.

In STEP 15010, support assemblies 300*ii* comprising lyophilized nerve segments are removed from chamber 601.

In STEP 15020, one of proximal end 304 and distal end 306 of support assembly 300*ii* comprising the lyophilized nerve segment is inserted and secured within alignment assembly 613. Alignment assembly 613 can be positioned below pin assembly 614 comprising a pin therein.

In STEP 15030, pin assembly 614 is lowered towards alignment assembly 613 comprising support assembly 300*ii* such that the pin penetrates at least a portion of the lyophilized nerve segment. The pin can be configured to create a channel extending through at least a portion of the lyophilized nerve segment. In some embodiments, the pin creates a channel that extends the full length of the lyophilized nerve.

In STEP 15040, pin assembly 614 is raised away from alignment assembly 613 such that the pin is removed from the lyophilized nerve segment.

In STEP 15050, comprising an optional step, pin assembly 614 can be repositioned above alignment assembly 613 comprising support assembly 300*ii*. STEP 15030 can be repeated to create an additional channel extending through at least a portion of the lyophilized nerve segment.

STEPs 15030 through 15050 can be repeated until the lyophilized nerve segment comprises a desired number of channels.

In STEP 15060, support assembly 300*ii* comprising the lyophilized nerve segment is released and removed from alignment assembly 613.

Upon the conclusion of Method 15000, the lyophilized nerve segment comprises a nerve graft-conduit combination (referred to as "device 400" herein).

Figure 31:
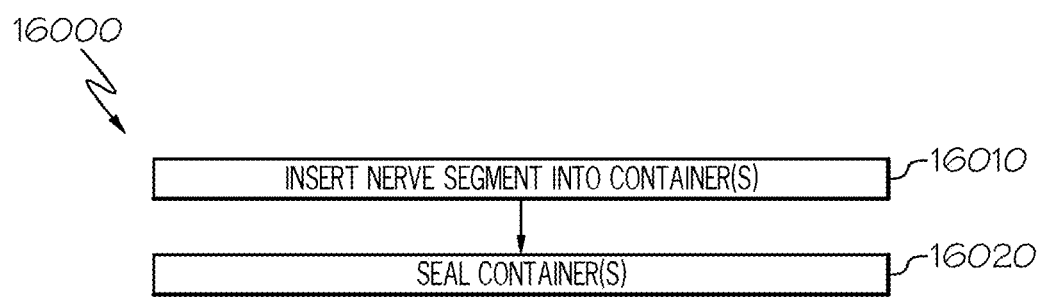
FIG. 31 illustrates a method for packaging a nerve graft-conduit, consistent with the present inventive concepts.

Referring now to FIG. 31, a method for packaging a nerve graft-conduit combination is illustrated, consistent with the present inventive concepts. Method 16000 can be configured to package device 400 produced in Method 15000 described herein in reference to FIG. 30. Device 400 can be packaged for bulk storage and/or sterilization. Method 16000 is configured to be performed within an environment suitable for aseptic processing, such that that materials, devices, and components utilized in Method 16000 are transferred to and/or contained within an environment suitable for aseptic processing. For example, Method 16000 is performed utilizing a sterile work area and/or sterile handling, such as to prevent or otherwise reduce contamination from microorganisms (e.g. bacteria, fungi, virus, etc.).

In STEP 16010, insert device 400 into one or more containers.

In STEP 16020, seal the containers.

Figure 32:
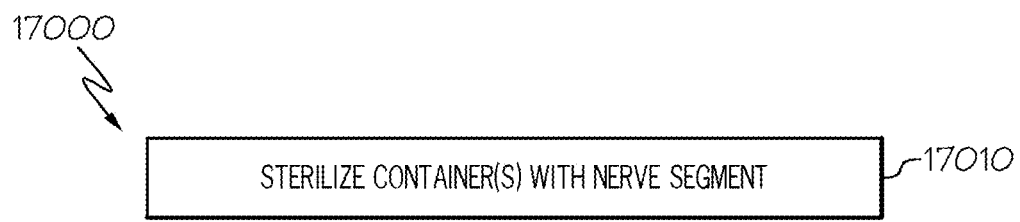
FIG. 32 illustrates a method for an irradiation based sterilization of a container comprising a nerve graft-conduit, consistent with the present inventive concepts.

Referring now to FIG. 32, a method for an irradiation based sterilization of a container comprising a nerve graft-conduit is illustrated, consistent with the present inventive concepts. Method 17000 can be configured to sterilize the packaged device 400 produced in Method 16000 described herein in reference to FIG. 31.

In STEP 17010, the containers comprising device 400 are sterilized.

The containers comprising device 400 can be sterilized via gamma irradiation, such that the containers are exposed to gamma radiation (e.g. Cobalt 60).

The containers comprising device 400 can be sterilized via electron-beam irradiation ("e-beam irradiation" herein), such that the containers are exposed to a stream of electrons.

Figure 33:
FIG. 33 illustrates a method for shipping and/or storing a container comprising a nerve graft-conduit, consistent with the present inventive concepts.

Referring now to FIG. 33, a method for shipping and/or storing a container comprising a nerve graft-conduit combination is illustrated, consistent with the present inventive concepts. Method 18000 can be configured to ship and/or store the sterilized device 400 produced in Method 17000 described herein in reference to FIG. 32.

In STEP 18010, the containers comprising device 400 are stored.

The containers comprising device 400 can be stored at a temperature of between 2° C. and 8° C., such as at a temperature of approximately 5° C.

Figure 34:
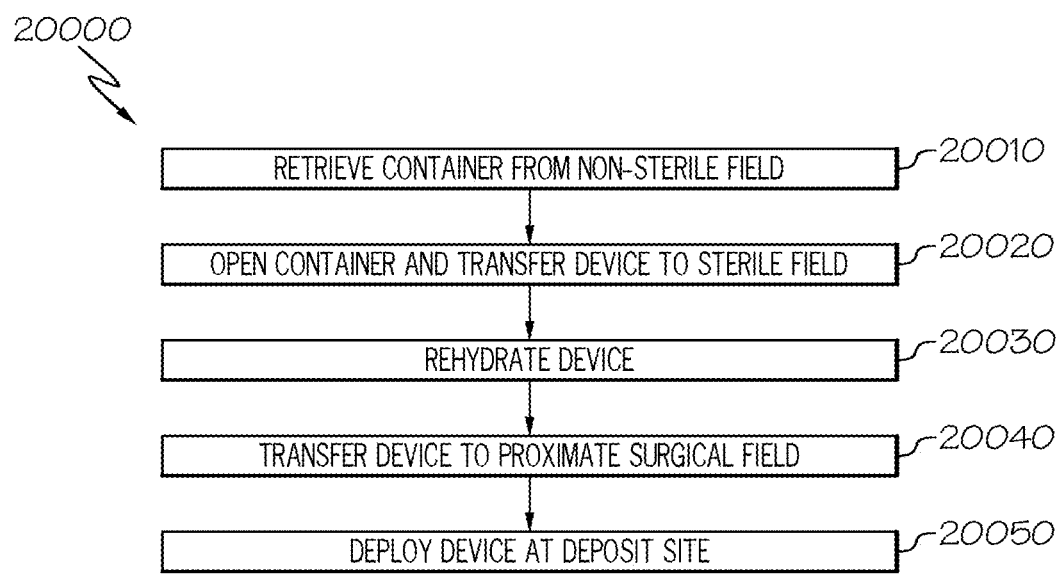
FIG. 34 illustrates a method for deploying a device comprising a nerve graft-conduit, consistent with the present inventive concepts.

Referring now to FIG. 34, a method for deploying a device comprising a nerve graft-conduit combination is illustrated, consistent with the present inventive concepts. Method 20000 can be configured to deploy device 400 comprising a nerve graft-conduit combination described herein.

As described herein in reference to Method 20000, and for non-limiting proposes, the deposit site comprises one, two, or more injured nerves.

In STEP 20010, the container comprising device 400 is retrieved from a non-sterile field (e.g. storage) by a first, non-sterile operator (e.g. circulating nurse, etc.) and is transported to the room within which the clinical procedure is to be performed (e.g. treatment room, operating room).

In STEP 20020, the first operator opens the container in proximity to the sterile field where a second sterile operator (e.g. scrub nurse, surgeon, etc.) assists with the transfer of all internal components (e.g. device 400) to the sterile field using aseptic techniques.

In STEP 20030, the second operator rehydrates device 400. In some embodiments, device 400 is immersed in 1×PBS for a duration of between 1 and 10 minutes. Upon rehydration, device 400 is configured to increase in size logarithmically.

In STEP 20040, the second operator transfers the rehydrated device 400 to a third, sterile operator (e.g. physician, surgeon, etc.) proximate to a surgical field.

In STEP 20050, the third operator deploys, or otherwise delivers, device 400 at the deposit site. In some embodiments, the third operator alters the size of device 400 to a desired length prior to deploying device 400 at the deposit site, such as by trimming or otherwise reducing the length of device 400.

Figure 35A:
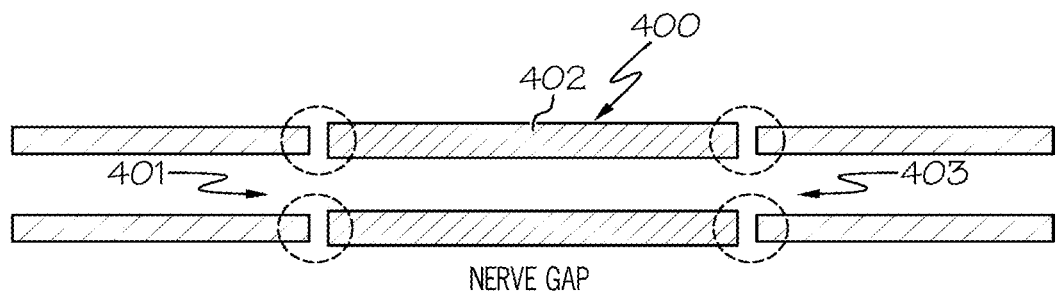
FIG. 35A illustrates a perspective view of a nerve graft-conduit combination deployed proximate a nerve gap, consistent with the present inventive concepts.

In some embodiments, and as shown in FIG. 35A, the deposit site comprises a never gap and device 400 is configured to connect two nerve stumps. The third operator can create two proximal and two distal sutures (e.g. 9-0 nylon monofilament suture) to secure device 400 to the nerve stumps.

Figure 35B:
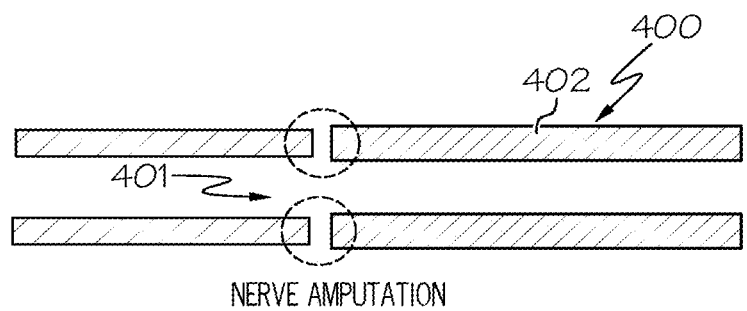
FIG. 35B illustrates a perspective view of a nerve graft-conduit combination deployed proximate an amputated nerve, consistent with the present inventive concepts.

In some embodiments, and as shown in FIG. 35B, the deposit site comprises an amputated nerve and device 400 is attached to an end portion amputated nerve. The third operator can create two proximal sutures (e.g. 9-0 nylon monofilament suture) to secure device 400 to the amputated nerve.

Figure 35C:
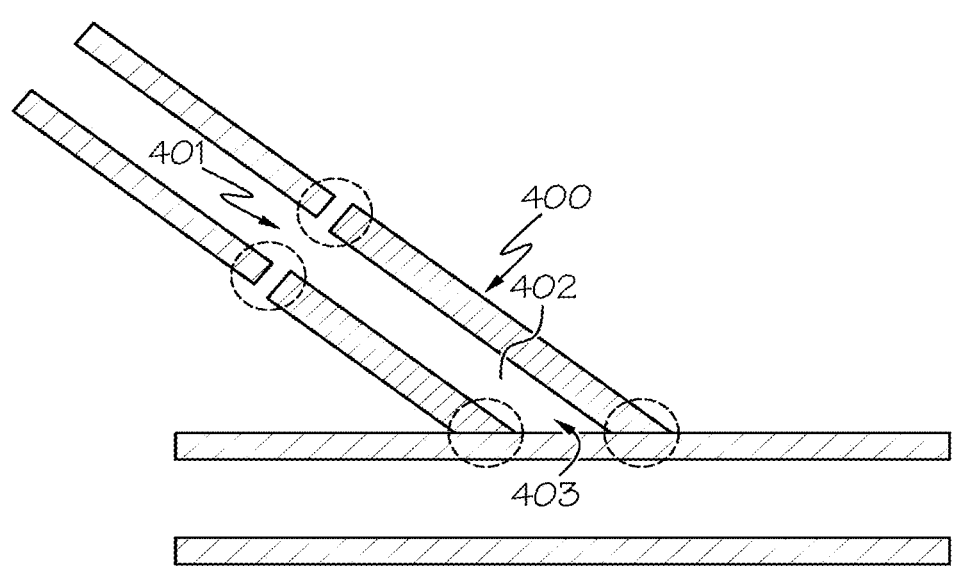
FIG. 35C illustrates a perspective view of a nerve graft-conduit combination deployed proximate a nerve transfer, consistent with the present inventive concepts.

In some embodiments, and as shown in FIG. 35C, the deposit site comprises a nerve transfer and device 400 is configured to connect a healthy nerve to an injured nerve. The third operator can create two proximal and two distal sutures (e.g. 9-0 nylon monofilament suture) to secure device 400 to the healthy nerve and the injured nerve.

The above-described embodiments should be understood to serve only as illustrative examples; further embodiments are envisaged. Any feature described herein in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the present inventive concepts, which are defined in the accompanying claims.

What is claimed is:

1. A method of making a conduit comprising:
   a. inserting an extracellular matrix into a support assembly;
   b. lyophilizing the extracellular matrix while within the support assembly; and
   c. selectively removing portions of the lyophilized extracellular matrix to create one or more lumens within the extracellular matrix, wherein the extracellular matrix is derived from raw material comprised of nerve tissue segment that has been decellularized and wherein the support assembly is constructed and arranged as a compressive tubular structure configured to modify the extracellular matrix.

2. The method of claim 1, wherein the support assembly is constructed and arranged to slidingly receive extracellular matrix therein, until a desired portion of the extracellular matrix is positioned within the support assembly.

3. The method of claim 1, wherein the extracellular matrix is inserted into the support assembly by pulling or otherwise advancing the extracellular matrix into the lumen of the support assembly.

4. The method of claim 1, wherein the internal diameter of the support assembly is smaller than the outer diameter of the extracellular matrix, such that the extracellular matrix is uniformly radially compressed when within the support assembly.

5. The method of claim 1, wherein the support assembly modifies the extracellular matrix to impart a uniform cylindrical shape.

6. The method of claim 1, wherein the support assembly is comprised of pores.

7. The method of claim 6, wherein the pores are distributed uniformly along the longitudinal and circumferential directions of the support assembly such that the pores are configured to allow for the passage of a fluid or vapor between the support assembly and the extracellular matrix and an external environment.

8. The method of claim 6, wherein the pores are configured to apply a uniform vacuum to the extracellular matrix within the support assembly such that the uniform vacuum maintains uniform contact between the extracellular matrix and the inner surface of the support assembly.

9. The method of claim 8, wherein one or more thermal and physical treatments can be applied concurrently with the uniform vacuum to induce the formation of coaxial layers within the extracellular matrix.

10. The method of claim 8, whereby at least one component which forms channels in the extracellular matrix is inserted into the extracellular matrix before lyophilization wherein the component is selected from the group consisting of pins, needles, suture threads, and filaments.

11. The method of claim 1, wherein one or more material removal devices and displacement devices are used to create one or more lumens in the extracellular matrix after lyophilization, the material removal or displacement device being configured to perform a function selected from the group consisting of a drill, grinding, rout, plane, bore, cut, and combinations thereof.

12. The method of claim 1, whereby a pin assembly is used to create one or more lumens within the extracellular matrix.

13. The method of claim 1, wherein a plurality of channels or lumens are created within the extracellular matrix via ablation and/or sublimation by using a laser.

14. The method of claim 1, wherein lyophilizing the extracellular matrix within the support assembly comprises a cycle, said cycle comprises:
   freezing the support assembly at a temperature between −60° C. and −20° C. for no less than four hours,
   drying the support assembly at a temperature between −8° C. and 0° C., and increasing the temperature of the support assembly over time to a temperature between 0° C. and 25° C.

15. The method of claim 8, wherein the cycle has a duration between 12 hours and 66 hours.

16. The method of claim 1, wherein the one or more lumens only extends through a portion of the extracellular matrix.

\* \* \* \* \*